US011505776B2

(12) United States Patent
Veraitch et al.

(10) Patent No.: US 11,505,776 B2
(45) Date of Patent: Nov. 22, 2022

(54) CONNECTOR

(71) Applicant: Oribiotech LTD, London (GB)

(72) Inventors: Farlan Veraitch, London (GB);
William Raimes, London (GB);
Richard Smith, Cambridgeshire (GB);
Neil Anthony Litten, Berkshire (GB)

(73) Assignee: Oribiotech LTD, London (GB)

( * ) Notice: Subject to any disclaimer, the term of this patent is extended or adjusted under 35 U.S.C. 154(b) by 0 days.

(21) Appl. No.: 17/459,945

(22) Filed: Aug. 27, 2021

(65) Prior Publication Data
US 2021/0388305 A1    Dec. 16, 2021

Related U.S. Application Data

(63) Continuation-in-part of application No. PCT/GB2020/053229, filed on Dec. 16, 2020.

(30) Foreign Application Priority Data

Dec. 17, 2019  (GB) ..................................... 1918663
Jul. 2, 2020    (GB) ..................................... 2010167

(51) Int. Cl.
*A61J 1/20*    (2006.01)
*A61J 1/00*    (2006.01)
(Continued)

(52) U.S. Cl.
CPC .............. *C12M 33/04* (2013.01); *A61J 1/00* (2013.01); *A61J 1/2003* (2015.05); *A61J 1/2013* (2015.05);
(Continued)

(58) Field of Classification Search
CPC .... A61J 1/00; A61J 1/20; A61J 1/2003; A61J 1/2013; A61J 1/2051; A61J 1/2055;
(Continued)

(56) References Cited

U.S. PATENT DOCUMENTS 2,627,857 A *  2/1953  Marcelli ............. A61M 5/1782
                                                    604/407
4,576,211 A *  3/1986  Valentini ............... A61J 1/2096
                                                    141/329
(Continued)

FOREIGN PATENT DOCUMENTS

CN         202822121 U    3/2013
CN         202822123 U    3/2013
(Continued)

OTHER PUBLICATIONS

International Search Report for International Application No. PCT/GB2020/053229, dated Jun. 4, 2021, 4 pages.
(Continued)

*Primary Examiner* — Adam Marcetich
(74) *Attorney, Agent, or Firm* — TraskBritt

(57) ABSTRACT

There is provided a connector, for introducing or extracting a material to or from at least one receptacle, comprising a housing extending between a distal end and a proximal end, the housing comprising, at least at one end, a pierceable seal; a hollow needle mounted, at least partially, within the housing between the distal end and the proximal end of the housing, a first end of the hollow needle being connected or connectable to a first corresponding receptacle, and a second end of the hollow needle facing the pierceable seal at an end of the housing; and an actuating mechanism acting on the housing or the hollow needle to enable the hollow needle to pierce the pierceable seal thereby forming a communication through the pierceable seal, such that material is able to transfer through the connector.

13 Claims, 52 Drawing Sheets

(51) Int. Cl.
- *C12M 1/26* (2006.01)
- *C12M 1/12* (2006.01)
- *C12M 1/00* (2006.01)
- *C12M 3/00* (2006.01)

(52) U.S. Cl.
CPC ............ *C12M 23/06* (2013.01); *C12M 23/28* (2013.01); *C12M 23/34* (2013.01); *C12M 23/48* (2013.01); *C12M 47/02* (2013.01); *C12M 47/04* (2013.01)

(58) Field of Classification Search
CPC ...... A61J 1/2065; A61J 1/2089; A61J 1/2096; A61M 2039/1066; A61M 2039/1077
See application file for complete search history.

(56) References Cited

U.S. PATENT DOCUMENTS

| | | | |
|---|---|---|---|
| 4,872,494 A * | 10/1989 | Coccia | A61J 1/2096 141/383 |
| 4,936,841 A * | 6/1990 | Aoki | A61J 1/2089 604/413 |
| 5,445,631 A * | 8/1995 | Uchida | A61J 1/2089 604/412 |
| 5,456,678 A * | 10/1995 | Nicoletti | A61M 39/04 600/577 |
| 5,492,147 A | 2/1996 | Challender et al. | |
| 6,394,992 B1 | 5/2002 | Sjoholm | |
| 6,558,365 B2 | 5/2003 | Zinger et al. | |
| 7,297,140 B2 | 11/2007 | Orlu et al. | |
| 7,540,863 B2 | 6/2009 | Haindl | |
| 7,618,407 B2 | 11/2009 | Demay et al. | |
| 8,051,884 B2 | 11/2011 | Reuter | |
| 8,323,237 B2 | 12/2012 | Radmer et al. | |
| 8,636,689 B2 | 1/2014 | Halili, Jr. et al. | |
| 8,900,212 B2 | 12/2014 | Kubo | |
| 9,254,242 B2 | 2/2016 | Mueller et al. | |
| 9,839,581 B2 | 12/2017 | Qiu et al. | |
| 10,206,854 B2 | 2/2019 | Wu et al. | |
| 10,391,245 B2 | 8/2019 | Cronenberg et al. | |
| 2002/0068896 A1* | 6/2002 | Robinson | A61J 1/2089 604/82 |
| 2002/0123736 A1* | 9/2002 | Fowles | A61J 1/2089 604/413 |
| 2002/0128628 A1* | 9/2002 | Fathallah | A61M 5/1409 604/411 |
| 2003/0028156 A1 | 2/2003 | Juliar | |
| 2003/0055376 A1* | 3/2003 | Delay | A61J 1/2089 604/82 |
| 2003/0144633 A1 | 7/2003 | Kirchhofer | |
| 2003/0199847 A1* | 10/2003 | Akerlund | A61J 1/2089 604/411 |
| 2004/0199139 A1* | 10/2004 | Fowles | A61J 1/1406 604/414 |
| 2005/0203481 A1* | 9/2005 | Orlu | A61J 1/2089 604/411 |
| 2006/0089601 A1 | 4/2006 | Dionigi | |
| 2010/0121305 A1* | 5/2010 | Rogers | A61M 39/26 604/403 |
| 2010/0298768 A1* | 11/2010 | Halili, Jr. | A61J 1/2096 604/87 |
| 2011/0074148 A1* | 3/2011 | Imai | A61J 1/2096 285/308 |
| 2011/0168294 A1 | 7/2011 | Jakobsen et al. | |
| 2012/0053555 A1* | 3/2012 | Ariagno | A61J 1/2089 604/413 |
| 2012/0150125 A1* | 6/2012 | Karlsson | A61M 5/326 604/198 |
| 2012/0179128 A1* | 7/2012 | Takemoto | A61M 5/162 604/414 |
| 2014/0031761 A1* | 1/2014 | Young | B65B 3/003 604/191 |
| 2014/0034185 A1 | 2/2014 | Mueller et al. | |
| 2014/0311624 A1 | 10/2014 | Eilertsen et al. | |
| 2015/0057613 A1 | 2/2015 | Clemente et al. | |
| 2016/0296704 A1 | 10/2016 | Gibson | |
| 2017/0028132 A1 | 2/2017 | Cronenberg et al. | |
| 2018/0116908 A1 | 5/2018 | Spallek et al. | |
| 2018/0200449 A1* | 7/2018 | Cronenberg | A61J 1/2089 |
| 2018/0221573 A1 | 8/2018 | Hanson et al. | |
| 2019/0110953 A1 | 4/2019 | Deck | |
| 2019/0365605 A1* | 12/2019 | Ebrahim | B01L 3/5635 |
| 2021/0178082 A1* | 6/2021 | Franke | A61M 5/20 |
| 2021/0379297 A1* | 12/2021 | Bengtsson | A61M 5/3271 |

FOREIGN PATENT DOCUMENTS

| | | |
|---|---|---|
| DE | 4122476 A1 | 1/1993 |
| EP | 0335378 B1 | 10/1993 |
| EP | 1093784 B1 | 5/2008 |
| EP | 1287804 B1 | 2/2012 |
| EP | 2332510 B1 | 2/2013 |
| EP | 2512399 B1 | 4/2015 |
| EP | 2931208 B1 | 1/2017 |
| EP | 3125974 B1 | 1/2018 |
| FR | 2788431 B1 | 7/2000 |
| GB | 1419061 A | 12/1975 |
| IN | 228346 B | 3/2009 |
| WO | 98/32411 A1 | 7/1997 |
| WO | 2002/053086 A1 | 7/2002 |
| WO | 2018/101531 A1 | 6/2018 |
| WO | 2019/033004 A1 | 2/2019 |
| WO | 2019/175688 A1 | 9/2019 |

OTHER PUBLICATIONS

International Written Opinion for International Application No. PCT/GB2020/053229, dated Jun. 4, 2021, 6 pages.

United Kingdom Search Report for United Kingdom Application No. GB1918663.4, dated Apr. 29, 2020, 5 pages.

United Kingdom Search Report for United Kingdom Application No. GB2010167.1, dated Dec. 22, 2020, 4 pages.

* cited by examiner

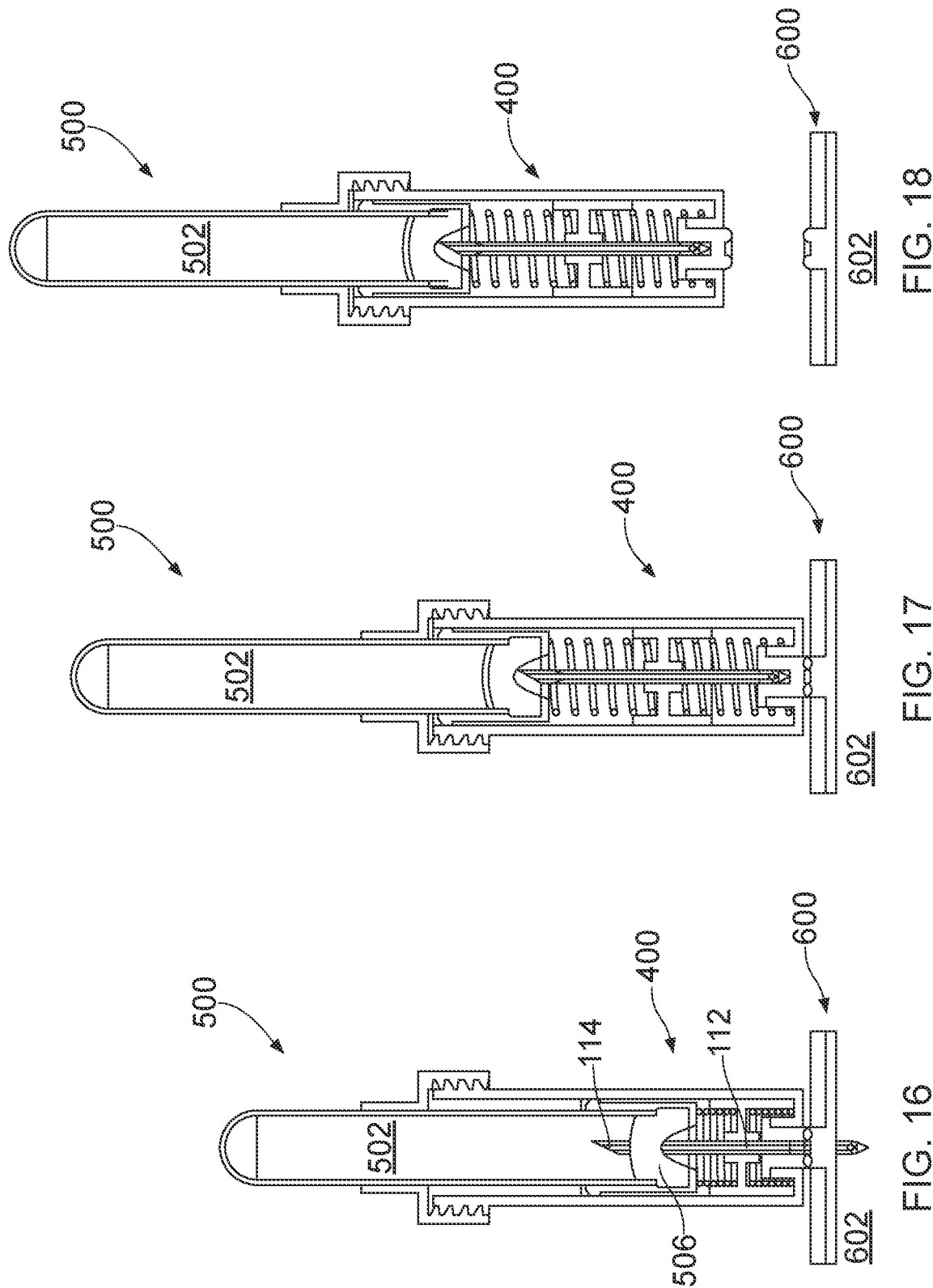

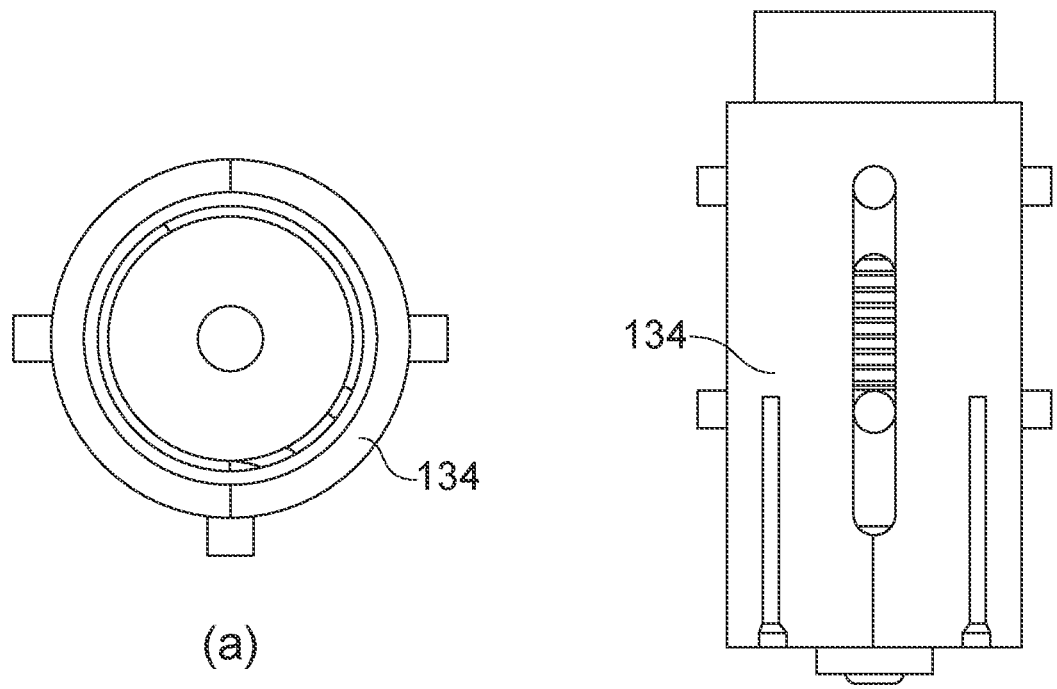
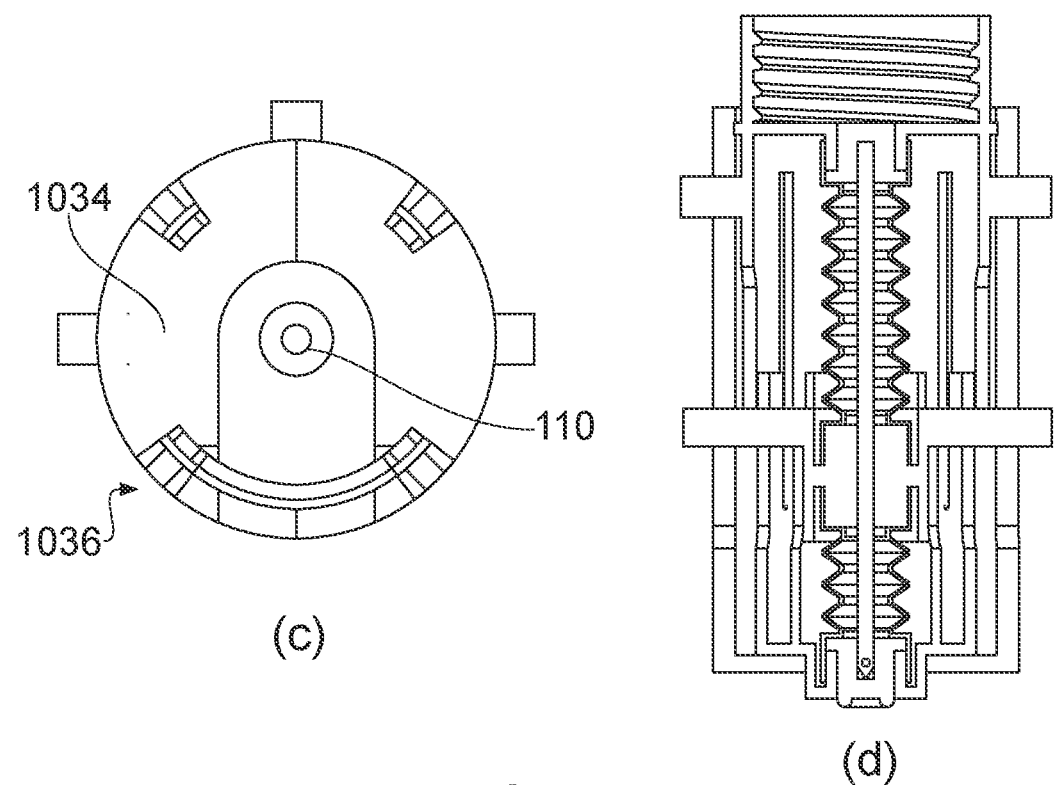
FIG. 46

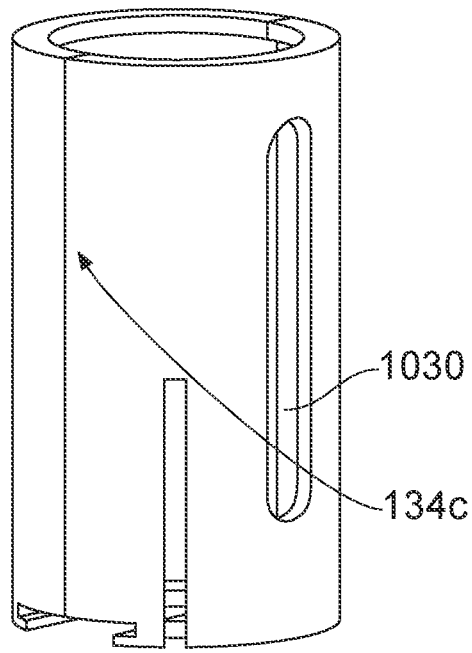
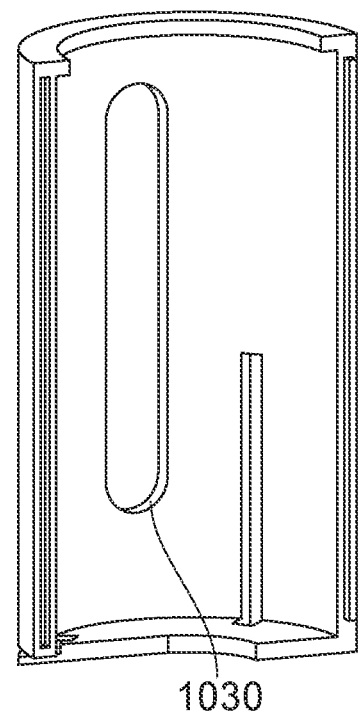
FIG. 52
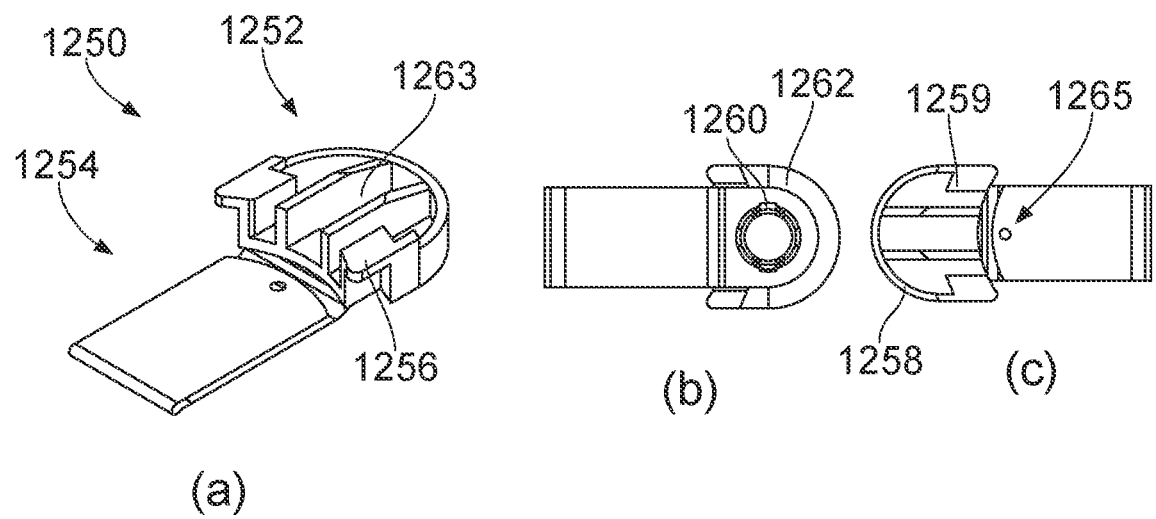
FIG. 53

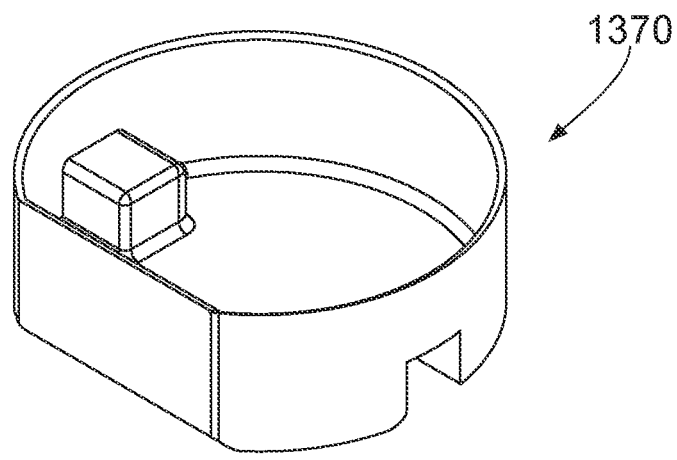
(a)
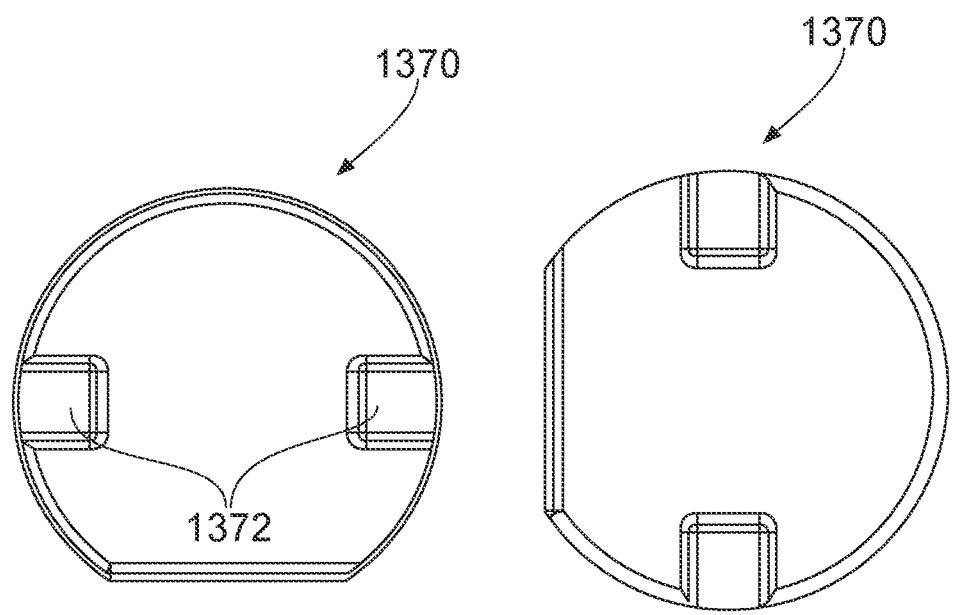
(b)     (c)
FIG. 78

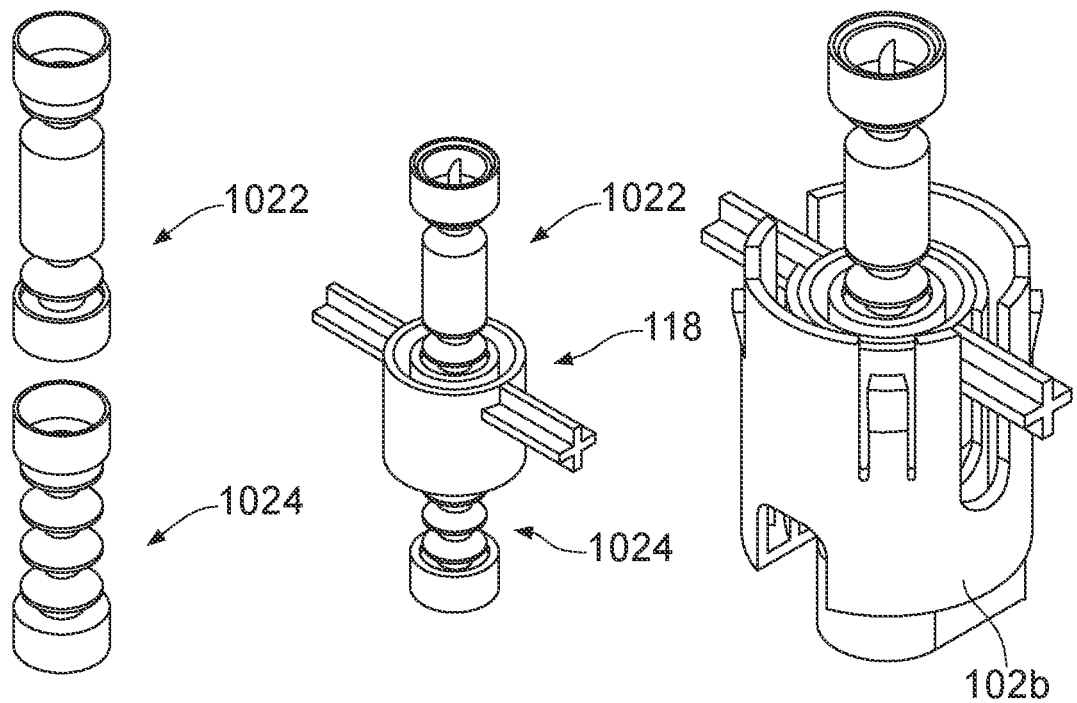
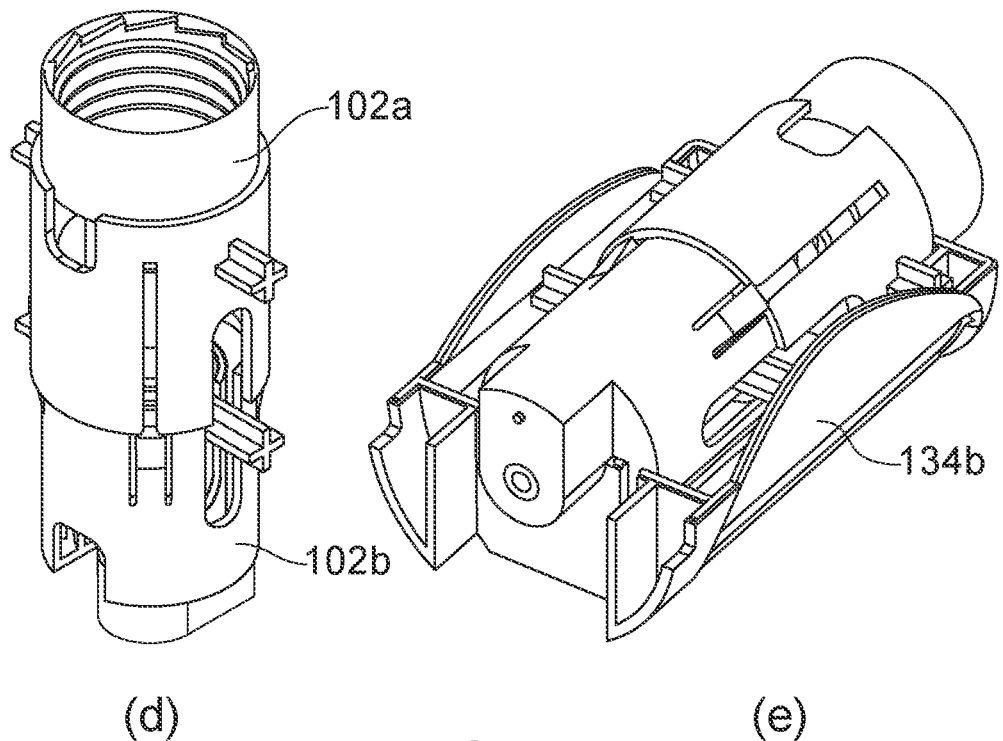
FIG. 79

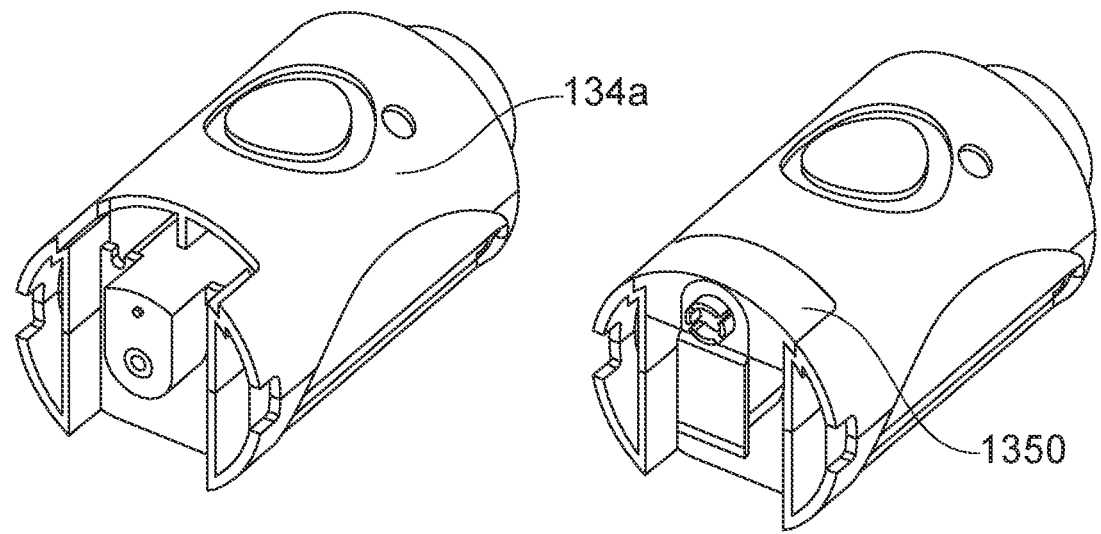
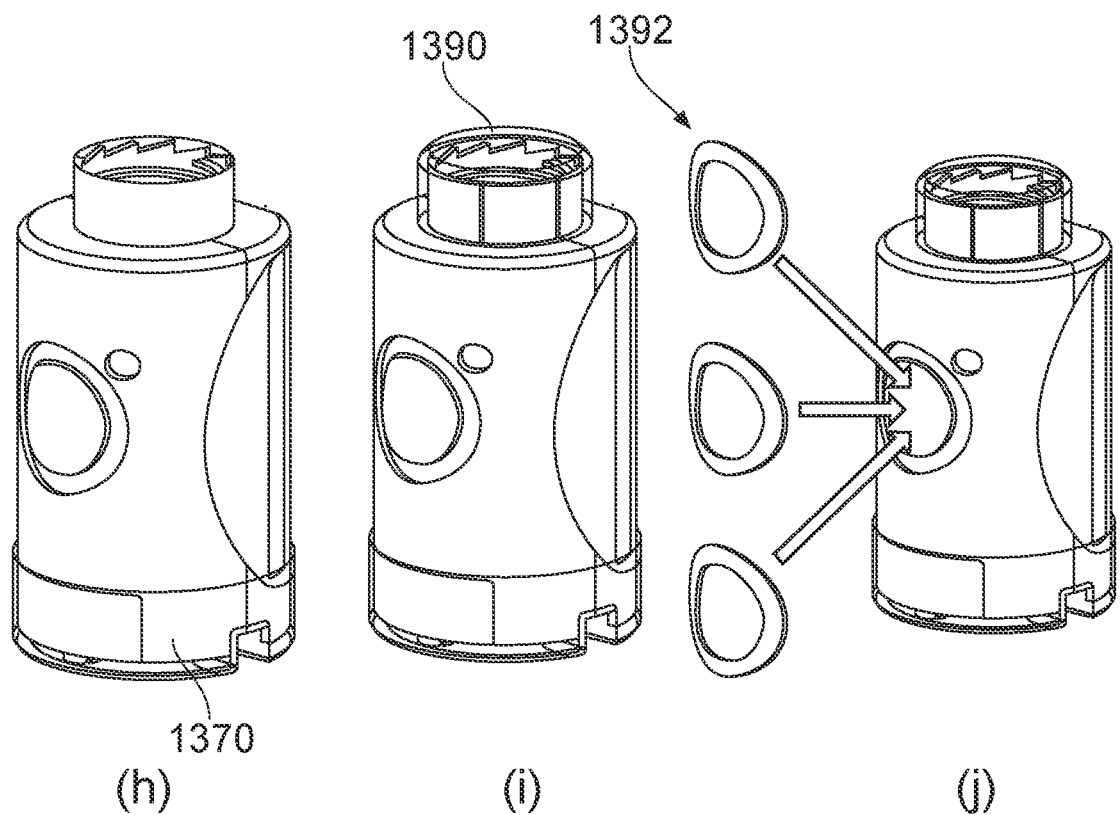
FIG. 79

CONNECTOR

CROSS-REFERENCE TO RELATED APPLICATIONS

Pursuant to 35 U.S.C. § 111(a), this application is a continuation-in-part of International Patent Application PCT/GB2020/053229, filed Dec. 16, 2020, which claims the benefit of Great Britain Patent Application Serial No. 2010167.1, filed Jul. 2, 2020, which claims the benefit of Great Britain Patent Application Serial No. 1918663.4, filed Dec. 17, 2019, the disclosure of each of which is hereby incorporated herein in its entirety by this reference.

TECHNICAL FIELD

The disclosure relates to a connector, for example, an aseptic connector. More particularly, the disclosure relates to a connector for introducing or extracting a material to or from at least one receptacle. The connector described herein may form part of a cell and/or gene therapy manufacture apparatus or process.

BACKGROUND

Cell and gene therapy manufacturing processes are often complex and include manual or semi-automated steps across several devices. Equipment systems used in various steps, or unit operations, of cell-based therapeutic products (CTP) manufacturing may include devices for various functions. These various functions may be, for example, cell collection, cell isolation, cell selection, cell expansion, cell washing, volume reduction, cell storage or transportation. The unit operations can vary immensely based on the manufacturing model (i.e., autologous versus allogenic), cell type, intended purpose, among other factors. In addition, cells are "living" entities sensitive to even the simplest manipulations, for example, such as differences in a cell transferring procedure. The role of cell manufacturing equipment in ensuring scalability and reproducibility is an important factor for cell and gene therapy manufacturing.

In addition, cell-based therapeutic products (CTP) have gained significant momentum thus there is a need for improved cell manufacturing equipment for various cell manufacturing procedures. These manufacturing procedures may include, for example, stem cell enrichment, generation of chimeric antigen receptor (CAR) T cells, and various cell manufacturing processes such as collection, purification, gene modification, incubation, recovery, washing, infusion into a patient, or freezing.

The culture or processing of cells typically requires the use of a device to hold the cells, for example in an appropriate culture medium when culturing the cells. The known devices include shaker flasks, roller bottles, T-flasks, bags and the like. Such devices are typically required to be connected to other devices, such as containers, interfaces or the like, so that various media may be introduced to, or removed from, the device holding the cells.

As such, there is a need for connecting one device to another device during cell and gene therapy manufacturing processes to enable fluid communication between the devices. Moreover, it is often desirable to provide a sterile, or aseptic, connection between the various devices, such that a sterile, or aseptic, fluid connection can be achieved. However, known connectors suffer from several drawbacks.

In some known connectors, specifically aseptic connectors, a first device or container having a first volume of fluid may be connected to a second device or container having a second volume of fluid through a genderless connector, a male-female connector, a threaded connector or the like. Usually, a first portion of the connector is connected to the first device and a second portion of the connector is connected to the second device. The first and second portions of the connector each include opposing removable adhesive strips that face toward one another and provide aseptically sealed ends of the first device and the second device. In use, the connection between the first and second portions of the connector is made, and the opposing adhesive strips adhere to one another. The user then removes the adhered strips, thus removing the adhered aseptic strips from the connection. In this way, an aseptic fluid pathway is provided between the first and second devices.

However, such aseptic connectors have many drawbacks. The major disadvantage of such aseptic connectors is that the first device or container and second device or container cannot be disconnected and/or reconnected aseptically. Instead, when the first and second portions of the connector are disconnected, a non-sterile environment is created. Thus, it is necessary to dispose of such connectors, or to sterilize such connectors, both of which are costly to the user. Moreover, the adhesive strips in such aseptic connectors are unsuitable where they may come into contact with liquids or are subjected to pressure, i.e., a pressure greater than atmospheric pressure. Furthermore, such adhesive strips are unsuitable for automated processes, and also require a cumbersome assembly on the part of the user.

Therefore, it is an object of the present disclosure to address some of the disadvantages associated with known connectors, particularly aseptic connectors.

BRIEF SUMMARY

According to one aspect of the disclosure, there is provided a connector, for introducing or extracting a material to or from at least one receptacle, comprising:
  a housing extending between a distal end and a proximal end, the housing comprising, at least at one end, a pierceable seal; and
  a hollow needle mounted, at least partially, within the housing between the distal end and the proximal end of the housing, a first end of the hollow needle being connected or connectable to a first receptacle, and a second end of the hollow needle facing the pierceable seal at an end of the housing;
  an actuating mechanism acting on the housing or the hollow needle to enable the hollow needle to pierce the pierceable seal, thereby forming a communication through the pierceable seal, such that material is able to transfer through the connector.

Aptly, in some embodiments, the connector comprises a housing that extends longitudinally between a distal end and a proximal end.

In some embodiments, the distal end of the housing of the connector comprises a pierceable seal. In some embodiments, the proximal end of the housing of the connector comprises a pierceable seal. In specific embodiments, both the distal end of the housing and the proximal end of the housing, of the connector, include a pierceable seal.

In some embodiments, the first end of the hollow needle may be connected to a first receptacle. In some embodiments, the first end of the hollow needle may be connectable to a first receptacle.

In some embodiments, the first end of the hollow needle is in communication with, or is able to be in communication with, a first receptacle.

In some embodiments the first receptacle comprises material. The first receptacle may be any vessel able to hold a material.

The material may be a solid. The material may be a fluid. The material may be a gas.

In some embodiments, the first end of the hollow needle may be pre-connected to a first receptacle. For example, the connector may be a part of a receptacle.

In some embodiments, the hollow needle is in direct communication with the first receptacle.

In another aspect of the present disclosure, there is also provided a receptacle comprising a connector as herein described. In some embodiments, the connector may be a part of a bioreactor.

In some embodiments, the connector may be configured and arranged to be connected to a first receptacle.

Aptly, the hollow needle is configured to be able to protrude through, or pierce, the pierceable seal. For example, the hollow needle may be pointed at one, or both ends. In some embodiments, the hollow needle comprises a pointed end. In specific embodiments, the hollow needle is pointed at both ends. In specific embodiments, the hollow needle is double ended. In specific embodiments, a first end or a second end comprises a pencil-point closed end and a port adjacent the pencil-point closed end i.e., a Whitacre end. That is, the port may provide fluid ingress and/or egress into or out of the hollow bore of the hollow needle. In specific embodiments, a first end of a second end comprises an open end. In specific embodiments, the open end comprises a beveled open end or a chamfered open end. That is, the open end, such as a beveled open end or a chamfered open end, may provide fluid ingress and/or egress into or out of the hollow bore of the hollow needle.

In particular embodiments, a longitudinally extending slot is provided within the hollow needle, extending from the open end toward the opposing end, such as toward the collar. This provides the advantage that the drainage of fluid, for example liquid or material, from a fluidly connected receptacle is aided by virtue of the longitudinally extending slot.

In specific embodiments, the hollow needle is an 18 gauge (18 G) needle. In other embodiments, the hollow needle is a 14 Gauge (14 G), a 15 Gauge (15 G), a 20 Gauge (20 G), a 21 Gauge (21 G), a 22 Gauge (22 G), a 23 Gauge (23 G), a 25 Gauge (25 G), or a 27 Gauge (27 G) needle. Preferably, the hollow needle comprises stainless steel.

For ease of describing the disclosure herein, the distal end of the connector refers to an upper, first, end of the connector, distal to a second receptacle. For ease of describing the disclosure herein, the proximal end of the connector refers to a lower, second, end of the connector, proximal to a second receptacle. These terms for describing the ends of the housing of the connector, or other parts of the connector are not meant to be limiting, but merely to assist in describing the disclosure.

Advantageously, the present disclosure provides an easy to use a connector to connect a first receptacle with a second receptacle. Advantageously, this may be connecting a first receptacle, for example, containing fluid or solid with a second receptacle, for example, containing fluid or solid. Further advantageously, the present disclosure provides a connector that is suitable for automation, for example, suitable for use in an automated cell and/or gene therapy manufacturing process.

Advantageously, the connector enables an easy communication between one of more receptacles, for the introducing or extracting of a material. The introduction or extracting of a material may be either way, through the connector. For example, the connector may enable the easy introducing of a material to a receptacle, or it may enable the easy extracting of a material from a receptacle.

As will be clear to the person skilled in the art, the disclosure applies to the introduction or extraction of any appropriate material, for example, fluids or solids. Fluids generally include liquids and gases, but may also include solutions, suspensions, gels, pastes or the like. The solids may be granular, for example, powder. In some embodiments, a volume of fluid of a first receptacle or second receptacle comprises a solid, or solids, or a fluid, or fluids. In some embodiments, the solid or solids may be suspended within a fluid, for example, a liquid. In some examples, the solid may include one or more magnetic beads for use in the culturing or processing of cells. The one or more magnetic beads may or may not be suspended within a fluid, for example, a liquid.

The material may comprise a magnetic bead. The material may comprise a plurality of magnetic beads.

The connector of the present disclosure provides the advantage that a first receptacle can be connected, disconnected and reconnected to a second receptacle by a connector. More particularly, the connection, disconnection and reconnection may be achieved in an aseptic, or sterile, manner. Furthermore, the connector may be more suited to automated processes and may be easier to handle and use.

In some embodiments, the actuating mechanism may include that the hollow needle is biasedly mounted.

In some embodiments, the hollow needle is biasedly mounted. In specific embodiments, the hollow needle is biasedly mounted at least partially within the housing of the connector. In specific embodiments, the hollow needle is biasedly mounted at least partially within the housing, the longitudinal length of the needle extending at least partially between the proximal end and the distal end of the housing of the connector. The hollow needle may be biasedly mounted by any means. In some embodiments, there is one biasing mechanism to provide a first biasing force. This first biasing force may be to biasedly mount the hollow needle.

In specific embodiments, there are two biasing mechanisms to biasedly mount the hollow needle.

In embodiments where there are two biasing mechanisms the second biasing mechanism may provide a second biasing force. This second biasing force may be to the hollow needle. In some embodiments, the connector comprises a spring to biasedly mount the hollow needle. In specific embodiments, the connector comprises two springs to biasedly mount the hollow needle. The hollow needle may be biasedly mounted in one direction or two directions. In some embodiments, the first biasing mechanism comprises a spring. In some embodiments, the second biasing mechanism comprises a spring. In specific embodiments, both the first biasing mechanism and the second biasing mechanism comprise a spring. In more specific embodiments, the or each spring may be a helical spring.

In some embodiments, the actuating mechanism comprises a collar. In some embodiments, the actuating mechanism comprises a rail. In some embodiments, the actuating mechanism comprises both a collar and a rail. In some embodiments, the collar is with the housing of the connector. In some embodiments, the rail is with the housing. In some embodiments, the collar is configured to be able to move along the length of the rail. In some embodiments, the collar includes one or more protrusions configured to engage with the rail.

In some embodiments, the biasedly mounted needle is held by a collar within the housing of the connector. The collar may be regarded as a needle holder.

In certain embodiments, the connector further comprises an actuating mechanism to enable the hollow needle to pierce the pierceable seal to connect to a second receptacle.

In certain embodiments, the connector further comprises an actuating mechanism to enable the hollow needle to pierce the pierceable seal.

In certain embodiments, the connector further comprises an actuating mechanism to enable the hollow needle to pierce the pierceable seal, thereby forming a communication through the pierceable seal.

In certain embodiments, the connector further comprises an actuating mechanism to enable the hollow needle to pierce the pierceable seal, thereby forming a communication through the pierceable seal, such that material is able to transfer through the connector.

This provides the advantage that the connector can be actuated manually, without the risk of needle stick injuries, or by an automated system. In certain embodiments, this may advantageously enable connection of the two receptacles in an aseptic manner.

The actuating mechanism may include collapsing, or partial collapsing, of the housing. In some embodiments, the actuating mechanism comprises a collapsible housing.

Advantageously, this is a simple mechanism to achieve connection of the two receptacles in an easy to use manner. Collapsible housings for the connector may be inexpensive and simple to manufacture. Advantageously, connectors with a collapsible housing may be disposable.

In certain embodiments, the actuating mechanism moves the hollow needle, to enable the hollow needle to pierce the pierceable seal to connect to a second receptacle.

In certain embodiments, the actuating mechanism moves the hollow needle, to enable the hollow needle to pierce the pierceable seal. In certain embodiments, the actuating mechanism moves the hollow needle, to enable the hollow needle to pierce the pierceable seal to communicate with a second receptacle. In certain embodiments, the actuating mechanism moves the hollow needle, to enable the hollow needle to pierce the pierceable seal, thereby forming a communication through the pierceable seal, to communicate with a second receptacle.

In some embodiments, the actuating mechanism enables axial translation of the hollow needle. The axial translation of the hollow needle may enable the hollow needle to pierce a pierceable seal. In some embodiments, the actuating mechanism enables axial translation of the hollow needle to pierce the pierceable seal at the proximal end of the housing of the connector. In some embodiments, the actuating mechanism enables the axial translation of the hollow needle to pierce the pierceable seal at the distal end of the housing of the connector. In some embodiments, the actuating mechanism enables axial translation of the pierceable seal at the proximal end of the housing of the connector to contact the hollow needle to pierce the pierceable seal at the proximal end of the housing of the connector. In some embodiments, the actuating mechanism enables the axial translation of the pierceable seal at the distal end of the housing of the connector to contact the hollow needle to pierce the pierceable seal at the distal end of the housing of the connector.

In some embodiments, piercing of the pierceable seal thereby forms a communication through the pierceable seal.

In some embodiments, piercing of the pierceable seal thereby forms a communication through the pierceable seal, such that material is able to transfer through the connector.

In specific embodiments, the actuating mechanism enables the hollow needle to pierce a pierceable seal at both the proximal end and distal end of the housing of the connector.

In specific embodiments, where the actuating mechanism enables the hollow needle to pierce a pierceable at both the proximal end and the distal end of the housing of the connector, this may be, for example, by axial translation of the hollow needle and axial translation of one of the pierceable seals.

In certain embodiments, the actuating mechanism moves the housing or part of the housing, to enable the hollow needle to pierce the pierceable seal to connect to a second receptacle.

In certain embodiments, the actuating mechanism moves the housing or part of the housing, to enable the hollow needle to pierce the pierceable seal to communicate with a second receptacle.

In certain embodiments, the housing is collapsible between the proximal end and the distal end to allow the hollow needle to pierce the pierceable seal to connect to a second receptacle.

In certain embodiments, the housing is collapsible between the proximal end and the distal end to allow the hollow needle to pierce the pierceable seal to communicate with a second receptacle.

In certain embodiments, the actuating mechanism comprises an outer sleeve configured to enable the hollow needle to pierce the pierceable seal to connect to a second receptacle.

In certain embodiments, the actuating mechanism comprises an outer sleeve configured to enable the hollow needle to pierce the pierceable seal to communicate with a second receptacle.

In certain embodiments, the outer sleeve is configured such that at least a partial rotation of the outer sleeve causes axial translation of the hollow needle to pierce the pierceable seal to connect to a second receptacle.

In certain embodiments, the outer sleeve is configured such that at least a partial rotation of the outer sleeve causes axial translation of the hollow needle to pierce the pierceable seal to communicate a second receptacle.

This provides the advantage that the connector can be actuated manually without the risk of needle stick injuries.

In some embodiments, the first end of the hollow needle is connected or connectable to a first receptacle, and the actuating mechanism enables the hollow needle to pierce the pierceable seal to connect the second end of the hollow needle to a second receptacle.

In some embodiments, the first end of the hollow needle is connected or connectable to a first receptacle, and the actuating mechanism enables the hollow needle to pierce the pierceable seal to enable the second end of the hollow needle to communicate with a second receptacle.

In some embodiments, the actuating mechanism may be configured such that it is only operable once the connector has engaged with both the first receptacle and the second receptacle. That is, in some embodiments the actuating mechanism may only be operable once the first receptacle is connected to the distal end of the housing, and when the second receptacle is connected to the proximal end of the housing.

In some embodiments, the actuating mechanism may include one or more engagement portions configured to engage with a corresponding portion of a receptacle, such that, upon engagement of the or each engagement portion with the corresponding portion, the actuating mechanism is operable.

This provides the advantage that needle stick injuries are avoided, as the hollow needle can only be actuated once connected to respective first and second receptacles.

In certain embodiments, the outer sleeve is configured such that the outer sleeve causes a releasable locking engagement between a proximal end of the outer sleeve of the connector and a portion of a corresponding receptacle, for example a second receptacle.

This provides the advantage that the user can easily identify, either tactilely, visually or tactiovisually, that the connector is correctly connected to a corresponding receptacle.

The connector of the present disclosure in some embodiments is able to releasably attach to one or more receptacles. In some embodiments, the connector is able to releasably attach to one or more receptacles in a fluid tight manner. In some embodiments, the connector is able to releasably attach to one or more receptacles in an aseptic tight manner.

In certain embodiments, the collapsible housing comprises an upper housing portion and a lower housing portion, the upper housing portion being axially movable along a central longitudinal axis with respect to the lower housing portion. Thus, the upper housing portion may be collapsible with respect to the lower housing portion. In some examples, collapsing the upper housing portion with respect to the lower housing portion causes the hollow needle to pierce a pierceable hermetic seal of the upper housing portion.

In some embodiments, a first portion of the collapsible housing may be axially movable, or translatable, along a central axis extending between the distal and proximal ends of the connector, with respect to a second portion of the collapsible housing. Thus, a movable portion of the housing and a stationary portion of the housing may be provided.

In certain embodiments, an outer sleeve may provide for collapsing, or actuation, of the upper housing portion with respect to the lower housing portion. Thus, the outer sleeve may be regarded as forming part of the actuating mechanism.

Alternatively, in certain embodiments, the collapsible housing comprises an upper housing portion and a lower housing portion, the lower housing portion being axially movable along a central longitudinal axis with respect to the upper housing portion. Thus, the lower housing portion may be collapsible with respect to the upper housing portion. In some examples, collapsing the lower hosing portion with respect to the upper housing portion causes the hollow needle to pierce a pierceable hermetic seal of the lower housing portion.

Further alternatively, in certain embodiments, the collapsible housing comprises an upper housing portion and a lower housing portion, the lower housing portion being axially movable along a central longitudinal axis with respect to the upper housing portion, and the upper housing portion being axially movable along the central longitudinal axis with respect to the lower housing portion. Thus, each of the lower housing portion and the upper housing portion may be collapsible with respect to one another. In some examples, collapsing the lower housing portion with respect to the upper housing portion, and collapsing the upper housing portion with respect to the lower housing portion, causes the hollow needle to pierce a pierceable hermetic seal of the upper housing portion and a pierceable hermetic seal of the lower housing portion. The sequential piercing of the seals may be controlled by the order of collapsing.

In certain embodiments, the upper housing portion comprises at least one actuatable lug configured to move the upper housing portion along the central longitudinal axis, the at least one actuatable lug of the upper housing portion protruding at least partially, or mostly or fully, through at least one slot of the outer sleeve. That is, in some embodiments, the outer sleeve further comprises at least one slot through which the actuatable lug of the upper housing protrudes, at least partially, therethrough.

This provides the advantage that the connector is suitable for automated actuation. Thus, the connector is advantageously suitable for an automated cell and/or gene therapy manufacturing process.

In some embodiments, the upper housing portion comprises a plurality of actuatable lugs. In some embodiments, the outer sleeve comprises a plurality of slots. In specific embodiments, each actuatable lug protrudes at least partially, or mostly or fully, through one of the plurality of slots.

In some embodiments, the upper housing portion comprises a pair of diametrically opposed actuatable lugs. In some embodiments, the outer sleeve comprises a pair of diametrically opposed slots. In specific embodiments, each actuatable lug protrudes at least partially through one of the pair of slots.

In some embodiments, the actuatable lugs of the upper housing portion have a circular or cross-shaped, i.e., crucifix-shaped, cross-section.

In some embodiments, the upper housing portion comprises at least one rib. In some embodiments, the upper housing portion comprises a pair of ribs. In some embodiments, the upper housing portion comprises a pair of ribs, each rib being disposed at either side of an actuatable lug of the upper housing portion. In particular embodiments, the or each rib of the upper housing portion may be configured and arranged to cooperate with one or more corresponding recesses on the outer sleeve. In other embodiments, the or each rib of the upper housing portion may be configured and arranged to frictionally engage with an inner wall of the outer sleeve.

This provides the advantage that rotatable movement of the upper housing portion, specifically within the outer sleeve, is prevented. Thus, the hollow needle is retained in a substantially vertical, or longitudinally extending, manner. In this way, during use, the hollow needle is caused to move substantially, or completely, axially, rather than forming an angle during actuation with respect to the pierceable seal. Thus, a consistent piercing action may be achieved.

In some embodiments, the lower housing portion comprises at least one outwardly extending flange. The outwardly extending flange may extend outwardly, i.e., away from a central longitudinal axis of the lower housing portion, from an outer surface of the lower housing portion. In some embodiments, the lower housing portion comprises a pair of outwardly extending flanges. In some embodiments, the pair of outwardly extending flanges is diametrically opposed. In some embodiments, the or each outwardly extending flange or flanges may be configured and arranged to be received within a corresponding slot or slots of the outer sleeve.

This provides the advantage that the lower housing portion is fixedly retained in a stationary manner to the outer sleeve, for example, with respect to the upper housing portion. Thus, a more reliable actuating of the connector may be ensured.

In certain embodiments, the actuating mechanism comprises a collar operably coupled to the hollow needle, the collar comprising at least one actuatable lug configured to move the collar along a central longitudinal axis, at least one actuatable lug of the collar protruding at least partially through at least one slot of the outer sleeve. That is, in some embodiments, the outer sleeve further comprises at least one slot through which the actuatable lug of the collar protrudes, at least partially, therethrough. Such at least one slot may be different, or the same, as the at least one slot through which the actuatable lugs of the upper housing portion at least partially protrudes i.e., separate slots or a unitary slot for both the actuatable lug of the collar and the actuatable lug of the upper housing portion.

In some examples, axial translation of the collar, and thus the hollow needle, along the central longitudinal axis, toward the proximal end, causes the hollow needle to pierce a pierceable hermetic seal of the lower housing portion.

This provides the advantage that the connector may be actuated in a sequential manner by an automated system. Further, this provides the advantage that the sequential manner of piercing may be controlled by an automated system. Additionally, the use of such a connector, and the piercing of seals thereof, is less susceptible to human error.

In some embodiments, the actuatable lugs of the collar have a circular or cross-shaped, i.e., crucifix-shaped, cross-section.

In some embodiments, the collar comprises a plurality of actuatable lugs. In some embodiments, the outer sleeve comprises a plurality of slots. In specific embodiments, each actuatable lug protrudes at least partially, or mostly or fully, through one of the plurality of slots.

In some embodiments, the collar comprises a pair of diametrically opposed actuatable lugs. In some embodiments, the outer sleeve comprises a pair of diametrically opposed slots. In specific embodiments, each actuatable lug of the collar protrudes at least partially, or mostly or fully, through one of the pairs of slots.

In specific embodiments, the outer sleeve comprises a first plurality of slots, each configured and arranged so that an actuatable lug of the upper housing portion at least partially, or mostly or fully, protrudes therethrough, and the outer sleeve comprises a second plurality of slots, each configured and arranged so that an actuatable lug of the collar at least partially, or mostly or fully, protrudes therethrough.

That is, in certain embodiments, there are distinct slots for the actuatable lugs of the upper housing portion, and there are distinct slots for the actuatable lugs of the collar. In some examples, each of the first plurality of slots may be spaced apart about the outer sleeve by approximately 120°. In some examples, each of the second plurality of slots may be spaced apart about the outer sleeve by 120° and are offset with respect to the first plurality of slots.

This provides the advantage that separate actuating mechanisms, for engaging the distinct actuatable lugs, may be provided.

In specific embodiments, the outer sleeve comprises a first slot and a second slot diametrically opposed to the first slot, wherein one of a pair of the actuatable lugs of the collar and one of a pair of the actuatable lugs of the upper housing portion at least partially, or mostly or fully, protrude through the first slot, and wherein the other of the pair of the actuatable lugs of the collar and the other of the pair of the actuatable lugs of the upper housing portion at least partially, or mostly or fully, protrude through the second slot.

That is, the first slot includes both an actuatable lug of the collar and an actuatable lug of the upper housing portion protruding, at least partially, therethrough. Likewise, the second slot includes both an actuatable lug of the collar and an actuatable lug of the upper housing portion protruding, at least partially, therethrough.

Specifically, the outer sleeve comprises a side wall having a first slot, receiving a first actuatable lug of the upper housing portion and a first actuatable lug of the collar, and a second slot, diametrically opposed to the first slot, receiving a second actuatable lug of the upper housing portion and a second actuatable lug of the collar.

More specifically, in certain embodiments, the outer sleeve comprises a side wall having a first slot and a second slot, the second slot being diametrically opposed to the first slot; the upper housing portion comprises a first actuatable lug extending from a body of the upper housing portion, and a second actuatable lug extending from the body of the upper housing portion, the first and second actuatable lugs being diametrically opposed to one another; the collar comprises a first actuatable lug extending from an outer wall of the collar, and a second actuatable lug extending from the outer wall of the collar, the first and second actuatable lugs being diametrically opposed to one another; wherein the first actuatable lug of the upper housing and the first actuatable lug of the collar protrude at least partially through the first slot of the outer sleeve, and wherein the second actuatable lug of the upper housing and the second actuatable lug of the collar protrude at least partially through the second slot of the outer sleeve.

This provides the advantage that an actuating mechanism having a smaller footprint may be utilized.

Generally, the one or more slots in the outer sleeve may provide access to the actuatable lugs of the upper housing portion and/or the collar. The one or more slots may provide access to a user, i.e., manual access, or to a robot, i.e., automated access.

In certain embodiments, the outer sleeve comprises a side wall, preferably a substantially cylindrical side wall. In some embodiments, the one or more slots, i.e., the first slot or first plurality of slots and/or the second slot or the second plurality of slots, are formed within the side wall. The outer sleeve may be formed of two half-pipe portions operably coupled together to form the outer sleeve. The two half-pipe portions may be welded, adhered, clipped or the like to one another.

In certain embodiments, the outer sleeve comprises a front wall, a rear wall, and side walls adjoining the front wall and the rear wall. There may be two side walls. In some examples, the one or more slots, i.e., the first slot or first plurality of slots and/or the second slot or second plurality of slots, are provided in the or each side wall. The outer sleeve may further comprise a protective wall, forming a gripping region of the outer sleeve, extending over the one or more slots. In this way, the protective wall is configured to prevent manual access to the components within the outer sleeve, whilst allowing for automated actuation of the connector. The protective wall may be knurled or the like to enhance gripping by the user.

In certain embodiments, at least one gaiter is provided to enclose the hollow needle. In some examples, a single flexible gaiter is provided to enclose the hollow needle and the collar. In other examples, a first flexible gaiter is provided to enclose a first portion of the hollow needle, and a second flexible gaiter is provided to enclose a second portion of the hollow needle. The first flexible gaiter may extend from an upper surface of the collar to a lower surface of the upper housing portion. The second flexible gaiter may extend from a lower surface of the collar to an upper surface of the lower housing portion. The at least one gaiter may enclose the hollow needle within an aseptic, or sterile, environment. Thus, the at least one gaiter may aseptically seal the hollow needle therein. Thus, the at least one gaiter may hermetically seal the hollow needle therein.

This provides the advantage that an aseptic environment is ensured around the hollow needle. Further, needle-stick injuries may be prevented.

In certain embodiments, the hollow needle is a double ended needle.

This provides the advantage that two receptacles, optionally including a septum, can be easily connected.

In certain embodiments, both the proximal end and the distal end of the housing of the connector comprise a pierceable seal.

In certain embodiments, the double ended hollow needle is mounted within the housing, and wherein each end of the double ended hollow needle, when biasedly mounted within the housing, face a pierceable seal of either the proximal end or distal end of the housing.

This provides the advantage that the hollow needle may be maintained within an aseptic, or sterile, environment.

In certain embodiments, the first end, i.e., adjacent the proximal end of the housing, of the double ended hollow needle comprises a pencil-point closed end and a port adjacent the pencil-point closed end. Such an end may be referred to as a Whitacre end.

This provides the advantage that the first end of the double ended needle can repeatedly pierce a resealable pierceable seal, for example of the connector, a container, a bioreactor or the like, and ensure the resealability of such seal. Thus, an aseptic environment is maintained.

In certain embodiments, the second end, i.e., adjacent the distal end of the housing, of the double ended hollow needle comprises an open end, such as a beveled open end.

This provides the advantage that the second end of the double ended needle can easily pierce a pierceable seal. Particularly, a smaller actuation force may be required for the second end to pierce the pierceable seal.

In certain embodiments, the connector further comprises an actuating mechanism to enable the double ended hollow needle to pierce the pierceable seal at both the proximal end and the distal end.

In certain embodiments, the actuating mechanism comprises an outer sleeve configured to enable the double ended hollow needle to pierce each pierceable seal to connect to a first receptacle and a second receptacle.

This provides the advantage that the hollow needle, in some embodiments, can aseptically connect to, or communicate with, a receptacle at each end of the housing.

In some embodiments, the connector further comprises an outer sleeve. In some embodiments, the housing of the connector comprises an outer sleeve. In some embodiments, the actuating mechanism comprises an outer sleeve. The outer sleeve may be located on the housing of the connector. The outer sleeve may be located on the housing of the connector, between the proximal end and the distal end of the housing of the connector. In some embodiments, the outer sleeve is rotatable. In some embodiments, the outer sleeve is rotatable in both directions.

In some embodiments, the outer sleeve is configured such that at least a partial rotation of the outer sleeve causes axial translation of the hollow needle to pierce at least one pierceable seal positioned at an end of the housing of the connector. This may be, for example, a pierceable seal positioned at the proximal end or the distal end of the housing.

In some embodiments, the outer sleeve is configured such that at least a partial rotation of the outer sleeve causes axial translation of a pierceable seal to contact the hollow needle to pierce the pierceable seal positioned at an end of the housing of the connector. This may be, for example, a pierceable seal positioned at the proximal end or the distal end of the housing.

In some embodiments, the outer sleeve is configured such that a partial rotation of the outer sleeve causes axial translation of a pierceable seal at both the proximal end and the distal end of the housing, to both contact the hollow needle to pierce the pierceable seal at both the proximal end and the distal end of the housing of the connector.

In certain embodiments, the outer sleeve is configured such that at least a partial rotation of the outer sleeve causes axial translation of the hollow needle to pierce each pierceable seal to connect to, or communicate with, a first receptacle and a second receptacle.

In specific embodiments, the outer sleeve is configured such that at least a partial rotation of the outer sleeve causes axial translation of the hollow needle and axial translation of a pierceable seal.

In some specific embodiments, wherein the connector comprising a pierceable seal at the proximal end of the housing and a pierceable seal at the distal end of the housing, the outer sleeve may be configured such that at least a partial rotation of the outer sleeve causes axial translation of the hollow needle and axial translation of a pierceable seal, such that the hollow needle pierces the pierceable seal at the distal end and the pierceable seal at the proximal end of the housing of the connector.

Partial rotation of the outer sleeve to move the hollow needle or a pierceable seal advantageously enables easy piercing of one or more pierceable seals. Advantageously, this may be in a fluid tight manner. Advantageously, this may be in an aseptic manner.

In certain embodiments, the outer sleeve is configured such that at least a partial rotation of the outer sleeve causes axial translation of the double ended hollow needle to pierce each pierceable seal to connect to, or communicate with, a first receptacle and a second receptacle.

This provides the advantage that the connector can be actuated manually without the risk of needle stick injuries.

In some embodiments, the outer sleeve is configured such that at least a partial axial translation of the outer sleeve causes axial translation of the hollow needle to pierce at least one pierceable seal positioned at an end of the housing of the connector. This may be, for example, a pierceable seal positioned at the proximal end or the distal end of the housing.

In some embodiments, the outer sleeve is configured such that at least a partial axial translation of the outer sleeve causes axial translation of a pierceable seal to contact the hollow needle to pierce the pierceable seal positioned at an end of the housing of the connector. This may be, for example, a pierceable seal positioned at the proximal end or the distal end of the housing.

In some embodiments, the outer sleeve is configured such that a partial axial translation of the outer sleeve causes axial translation of a pierceable seal at both the proximal end and the distal end of the housing, to both contact the hollow needle to pierce the pierceable seal at both the proximal end and the distal end of the housing of the connector.

In certain embodiments, the outer sleeve is configured such that at least a partial axial translation of the outer sleeve causes axial translation of the hollow needle to pierce each pierceable seal to connect to, or communicate with, a first receptacle and a second receptacle.

In specific embodiments, the outer sleeve is configured such that at least a partial axial translation of the outer sleeve causes axial translation of the hollow needle and axial translation of a pierceable seal.

In some specific embodiments, wherein the connector comprising a pierceable seal at the proximal end of the housing and a pierceable seal at the distal end of the housing, the outer sleeve may be configured such that at least a partial axial translation of the outer sleeve causes axial translation of the hollow needle and axial translation of a pierceable seal, such that the hollow needle pierces the pierceable seal at the distal end and the pierceable seal at the proximal end of the housing of the connector.

Partial axial translation of the outer sleeve to move the hollow needle or a pierceable seal advantageously enables easy piercing of one or more pierceable seals. Moreover, axial translation of the outer sleeve ensures that such a connector is more suited to automated processing. Advantageously, this may be in a fluid tight manner. Advantageously, this may be in an aseptic manner.

In certain embodiments, the outer sleeve is configured such that at least a partial axial translation of the outer sleeve causes axial translation of the double ended hollow needle to pierce each pierceable seal to connect to, or communicate with, a first receptacle and a second receptacle.

This provides the advantage that the connector can be actuated manually without the risk of needle stick injuries.

In certain embodiments, the connector further comprises a releasable attaching mechanism. The connector may be releasably attached, for example, to one or more containers, ports, connectors or bioreactors. In some embodiments, a releasable attaching mechanism comprises threads. In some embodiments, the connector comprises threads that correspond to threads on a corresponding element to which the connector may be releasably attached to. In some embodiments, the housing comprises a releasable connecting mechanism. In some embodiments, the housing comprises, at a proximal end of the housing, a releasable connecting mechanism. In some embodiments, the housing comprises, at a distal end of the housing, a releasable connecting mechanism. In some embodiments, the outer sleeve of the connector comprises a releasable attaching mechanism. In some embodiments, the outer sleeve comprises, at a proximal end of the outer sleeve, a releasable connecting mechanism. In some embodiments, the outer sleeve comprises, at a distal end of the outer sleeve, a releasable connecting mechanism.

In some embodiments, the connector may be rotated to releasably attach to a corresponding element. In some embodiments, a corresponding element may be rotated to releasable attach to the connector.

In certain embodiments, the outer sleeve is configured such that the outer sleeve causes a releasable locking engagement between a proximal end of the outer sleeve of the connector and a portion of a corresponding receptacle, for example, a second receptacle.

This provides the advantage that the user can easily identify, either tactilely, visually or tactiovisually, that the connector is correctly connected to a corresponding receptacle.

In some embodiments, the outer sleeve comprises threads. In some embodiments, the outer sleeve comprises threads at a proximal end of the outer sleeve. In some embodiments, the outer sleeve comprises threads at a distal end of the outer sleeve. In some embodiments, the outer sleeve comprises threads on the inner surface of the outer sleeve.

In certain embodiments, the hollow needle is biasedly mounted, at least partially, within the housing.

This provides the advantage that the hollow needle is arranged to move, thereby preventing needle stick injuries. Advantageously, the hollow needle may be held in a safe position but is able to move in use to pierce a pierceable seal, or seals.

In certain embodiments, the double ended hollow needle is biased in a direction toward the proximal end of the housing by a biasing mechanism. Preferably, the biasing mechanism is a helical spring. The helical spring may extend between a collar, operably coupled to the double ended hollow needle, and an upper housing portion.

This provides the advantage that sequential piercing of pierceable hermetic seals is achieved through a single spring.

In some embodiments, the upper housing portion may comprise at least one actuatable lug. The at least one actuatable lug may extend through at least one slot of an outer sleeve of the connector. Upon actuation of the at least one actuatable lug, the upper housing portion is caused to collapse with respect to a lower housing portion, so as to cause piercing of a pierceable hermetic seal within the lower housing portion by the hollow needle. Further actuation causes the spring to compress so as to subsequent cause piercing of a pierceable hermetic seal of the upper housing portion.

This provides the advantage that sequential piercing can be easily and precisely controlled. Thus, the connector is suitable for automation.

In certain embodiments, the double ended hollow needle is biased in a direction toward the distal end of the housing by a biasing mechanism. Preferably, the biasing mechanism is a helical spring. The helical spring may extend between a collar, operably coupled to the double ended hollow needle, and a lower housing portion.

This provides the advantage that sequential piercing of pierceable hermetic seals is achieved through a single spring.

In some embodiments, the lower housing portion may comprise at least one actuatable lug. The at least one actuatable lug may extend through at least one slot of an outer sleeve of the connector. Upon actuation of the at least one actuatable lug, the lower housing portion is caused to collapse with respect to a upper housing portion, so as to cause piercing of a pierceable hermetic seal within the upper housing portion by the hollow needle. Further actuation causes the spring to compress so as to subsequent cause piercing of a pierceable hermetic seal of the lower housing portion.

This provides the advantage that sequential piercing can be easily and precisely controlled. Thus, the connector is suitable for automation.

In certain embodiments, the double ended hollow needle is biased in a direction toward the proximal end of the housing by a first biasing mechanism, and biased in a direction toward the distal end of the housing by a second biasing mechanism.

In certain embodiments, the first biasing mechanism provides a first biasing force, and the second biasing mechanism provides a second biasing force, the first biasing force and the second biasing force being approximately equal.

This provides the advantage that the hollow needle may pierce each septum at approximately the same time.

In certain embodiments, the first biasing mechanism provides a first biasing force, and the second biasing mechanism provides a second biasing force, the first biasing force being greater than the second biasing force.

This provides the advantage that the hollow needle may firstly pierce the second septum, and secondly pierces the first septum, thereby providing sequential piercing of the septa.

In certain embodiments, the first biasing mechanism provides a first biasing force, and the second biasing mechanism provides a second biasing force, the second biasing force being greater than the first biasing force.

This provides the advantage that the hollow needle may firstly pierce the first septum, and secondly pierce the second septum, thereby providing sequential piercing of the septa.

In certain embodiments, the first biasing mechanism comprises a resilient or a non-resilient biasing mechanism.

In certain embodiments, the second biasing mechanism comprises a resilient or a non-resilient biasing mechanism.

In certain embodiments, the first biasing mechanism, or second biasing mechanism, or both the first biasing mechanism and the second biasing mechanism, comprise a helical spring or a deformable elastomeric material.

In certain embodiments, the first end, or the second end, or both the first end and second end, of the double ended hollow needle is beveled. That is, in certain embodiments, the first end or the second end or both the first and second end of the double ended hollow needle is or are beveled.

This provides the advantage that fluid may be directly connected into the through bore of the hollow needle, thereby ensuring that material is, for example, fully transferred from a first receptacle to a second receptacle. Moreover, spillage of material may be reduced, or avoided. Moreover, material, for example particles within a fluid, may also be directed through the hollow needle, such that the material may be efficiently and effectively transferred between, for example, receptacles.

In certain embodiments, the distal end of the housing is connectable to a first receptacle. In certain embodiments, the proximal end of the housing is connectable to a first receptacle.

In certain embodiments, the distal end of the housing comprises a threaded portion configured to engage with a corresponding threaded portion of a first receptacle.

In certain embodiments, the threaded portion comprises a septum seal having a central frustoconical depression.

This provides the advantage that fluid is, for example, fully transferred from a receptacle to the connector. Moreover, spillage of material may be reduced, or avoided. Moreover, material, for example solid particles within the fluid, may also be directed through the hollow needle, such that the material may be efficiently and effectively transferred between, for example, receptacles.

In certain embodiments, the threaded portion comprises an anti-rotational member.

In certain embodiments, the anti-rotational member comprises a plurality of inclined notches configured to engage with a plurality of corresponding notches, or rips, on a receptacle.

In certain embodiments, the pierceable seal at the or each end of the housing comprises a pierceable hermetic seal.

This provides the advantage that an aseptic, or sterile, environment may be maintained.

In some embodiments, the pierceable seal comprises a pierceable hermetic seal. In some embodiments, the pierceable seal comprises a resealable pierceable seal. In some embodiments, the pierceable seal comprises a releasable pierceable hermetic seal. In certain embodiments, the resealable pierceable hermetic seal comprises a septum seal. In some embodiments, the resealable pierceable seal is self-sealing. In some embodiments, the resealable hermetic seal is self-sealing. In some embodiments, the septum seal is self-sealing. In some embodiments, the septum seal is a self-sealing septum seal. In specific embodiments the pierceable seal is a self-sealing septum seal. In specific embodiments the pierceable seal is a self-sealing hermetic seal.

This provides the advantage that the pierceable hermetic seal is resealable, such that an aseptic, or sterile, connection, disconnection and reconnection can be made.

In certain embodiments, the pierceable seal comprises an annular septum seal. That is, the pierceable seal comprises a septum seal formed as an annulus. The annulus may be formed as a raised annular portion enclosing a circular flat base. The hollow needle may be configured to pierce through the circular flat base. The raised annular portion may be configured to engage, for example a face-to-face engagement, with a corresponding pierceable seal, such as another annular septum seal, for example corresponding raised annular portions in face-to-face engagement or received within the annulus of one another, or a flat septum seal.

This provides the advantage that the annular raised portion ensures sterility within the enclosed area to be pierced. Thus, an aseptic, or sterile, environment may be maintained.

In certain embodiments, the connector further comprises a cover disposed over the pierceable seal at the or each end of the housing of the connector.

In certain embodiments, the cover comprises a removable aseptic paper seal.

In certain embodiments, the connector further comprises an aseptic seal system including an aseptic membrane and a clip portion, the aseptic membrane being disposed over the pierceable hermetic seal at the or each end of the housing of the connector and being operably coupled to the clip portion.

This provides the advantage that the aseptic membrane ensures an aseptic environment at the or each pierceable hermetic seal during handling and/or set up of the connector and/or other components.

In certain embodiments, the clip portion is slidably operably connected to the connector such that the clip portion is slidable between a first configuration, in which the aseptic membrane is disposed over the or each pierceable hermetic seal, and a second configuration, in which the aseptic membrane is removed from the or each pierceable hermetic seal.

This provides the advantage that the aseptic seal system may be removed by an automated system prior to actuation. Thus, an aseptic environment is ensured during use.

In some embodiments, the clip portion is slidably operably connected to an outer sleeve of the connector.

In specific embodiments, the clip portion comprises a rail that is configured to be slidably operably received within a rail receiving portion of an outer sleeve of the connector.

In specific embodiments, the clip portion includes at least one, preferably two, protruding shoulders. In some examples, the at least one protruding shoulder is configured to be operably engaged by an aseptic seal actuating mechanism. More particularly, in some embodiments, the aseptic seal actuating mechanism is arranged to impart a pushing force onto the or each shoulder.

In specific embodiments, the clip portion includes at least locating element, configured and arranged to cooperate with a corresponding locating element of the outer sleeve. In particular embodiments, the clip portion includes an outwardly extending rib, such as a longitudinal rib, configured and arranged to cooperate with, for example, frictionally engage with, a corresponding rib or recess of the outer sleeve.

This provides the advantage that the clip portion, and thus the aseptic seal system, is maintained in position prior to engagement by an aseptic seal actuating mechanism.

In some embodiments, the aseptic membrane comprises an aseptic paper seal. Preferably, the aseptic membrane comprises an aseptic polyethylene film.

In some embodiments, the aseptic membrane comprises at least one fold, thereby forming a first surface configured to provide an aseptic seal to the or each pierceable hermetic seal, and a second surface configured to mate with a corresponding aseptic membrane. Any number of folds may be provided.

In certain embodiments, the connector is an aseptic connector.

In certain embodiments, at least one end of the connector is detachably engageable with a receptacle by rotating the connector.

In certain embodiments, the first end of the hollow needle may be fluidly connected to a first receptacle. That is, there may be a fluid connection between the first end of the hollow needle and the first receptacle is a fluid connection.

In certain embodiments, the first end of the hollow needle may be fluidly connectable to a first receptacle.

In certain embodiments, the actuating mechanism acts on the housing or the hollow needle to form a fluid communication through the pierceable seal.

In certain embodiments, the actuating mechanism acts directly on the housing. In other embodiments, the actuating mechanism acts directly on the hollow needle. The term "directly" is used to mean that the actuating mechanism acts on the respective component without any intervening or intermediary parts.

In some embodiments, the first receptacle may comprise a volume, for example, a volume of fluid. In some embodiments, the second receptacle may comprise a volume, for example, a volume of fluid.

The present disclosure also provides an aseptic seal system as described herein.

In some embodiments, the aseptic seal system may comprise a clip portion and an aseptic membrane operably coupled to the clip portion.

In some embodiments, the clip portion may comprise a front wall, a rear wall, side walls adjoining the front and rear walls, and a bottom wall. The clip portion may include a hollow body defined by the front wall, the rear wall, the side walls and the bottom wall. The hollow body may comprise one or more strengthening ribs extending from an inner surface of the front wall to an inner surface of the rear wall. The front wall may comprise one or more protruding shoulders configured to be engaged by an aseptic seal actuating mechanism. The aseptic seal actuating mechanism may be configured to provide a pushing force onto the or each protruding shoulder. The bottom wall may include an axially protruding member configured and arranged to cooperate with a receiving member of a corresponding aseptic seal system, for example, of a container or the like. The clip portion may comprise one or more locating elements, such as an outwardly extending rib or a plurality of outwardly extending ribs as described above, on one side wall, or both side walls.

In some embodiments, the clip portion may comprise one or more rails configured to be slidably received within a corresponding rail receiving portion of a connector.

In some embodiments, the aseptic membrane may comprise an aseptic paper seal. Preferably, the aseptic membrane comprises an aseptic polyethylene film. The aseptic membrane may comprise at least one fold, thereby forming a first surface configured to aseptically seal to a pierceable hermetic seal, such as a septum seal, and a second surface configured to mate with a corresponding aseptic membrane.

The present disclosure also relates to a method of removing an aseptic seal system from a connector.

In a first step, a connector and an aseptic seal system are provided, as described herein.

In a second step, an aseptic seal actuating mechanism is provided. Optionally, the aseptic actuating mechanism may be provided as part of an instrument, such as an incubator or a housing.

In a third step, the aseptic seal actuating mechanism engages with the clip portion of the aseptic seal system. Optionally, the aseptic seal actuating mechanism engages with one or more shoulders of the clip portion.

In a fourth step, the aseptic seal actuating mechanism imparts a force to the clip portion so as to remove, at least partially, the aseptic seal system from the connector. Optionally, the force may be a pushing force or a pulling force.

In a fifth step, at least partial removal of the clip portion causes at least partial removal of the aseptic membrane from a pierceable hermetic seal, thereby exposing at least a part, preferably all, of the pierceable hermetic seal.

The present disclosure also provides a system, comprising:
  a connector as described herein;
  a first receptacle detachably coupled to one end of the connector and wherein the first receptacle is connected to the first end of the hollow needle; and
  a second receptacle detachably coupled to one end of the connector and wherein the second receptacle is connected to the second end of the hollow needle.

This provides the advantage that a first receptacle can be connected, disconnected and reconnected to a second receptacle by a connector. More particularly, the connection, disconnection and reconnection can be achieved in an aseptic, or sterile, manner. Furthermore, the system may be more suited to automated processes and may be easier to handle and use.

In certain embodiments, the first receptacle or the second receptacle, or both the first receptacle and second receptacle comprises a pierceable seal coaxially aligned with the pierceable seal at the, or each, end of the housing of the connector.

In certain embodiments, the, or each, pierceable seal of the first receptacle or the second receptacle, or both the first receptacle and the second receptacle comprises a pierceable hermetic seal, and wherein the, or each, pierceable seal of the housing comprises a pierceable hermetic seal.

In certain embodiments, one or more of the pierceable hermetic seals comprises a septum seal. That is, in certain embodiments, the, or each pierceable seal of the first receptacle or the second receptacle, or both the first receptacle and the second receptacle comprises a septum seal. Additionally, or alternatively, in certain embodiments, the, or each, pierceable hermetic seal of the housing comprises a septum seal.

In certain embodiments, the, or each, pierceable seal of the first receptacle or the second receptacle, or both the first receptacle and the second receptacle, comprise an aseptic seal system including an aseptic membrane configured to mate with an aseptic membrane of the connector.

In certain embodiments, the system further comprises a cell processing platform or a vacutainer.

In certain embodiments, the first receptacle may be fluidly connected to the first end of the hollow needle.

In certain embodiments, the second receptacle may be fluidly connected to the second end of the hollow needle.

In some embodiments, the first receptacle may comprise a volume, for example, a volume of fluid. In some embodiments, the second receptacle may comprise a volume, for example, a volume of fluid.

The present disclosure also provides a system comprising:
  a container or vacutainer; and
  a connector as described herein;
    wherein the container or vacutainer is coupled to the distal end of the housing of the connector, and wherein the first end of the hollow needed is connected to the container or vacutainer.

This provides the advantage that a container or vacutainer can be connected, disconnected and reconnected to a second receptacle by a connector. More particularly, the connection, disconnection and reconnection can be achieved in an aseptic, or sterile, manner. Furthermore, the system may be more suited to automated processes and may be easier to handle and use.

In certain embodiments, the receptacle or bioreactor or container or vacutainer comprises a volume of fluid.

In certain embodiments, the first end of the hollow needle may be fluidly connected to the container or vacutainer, for example, fluidly connected to a volume of fluid thereof.

According to another aspect of the disclosure, there is also provided a receptacle comprising a connector as described herein. The receptacle may comprise a container, a vacutainer, or the like.

According to another aspect of the present disclosure, there is also provided a method of connecting two receptacles, comprising the steps of:
  providing a connector as herein described;
  connecting the distal end of the housing of the connector to a first receptacle, such that the first receptacle is connected with the first end of the hollow needle;
  detachably connecting the proximal end of the housing of the connector to a second receptacle comprising a pierceable seal, such that the pierceable seal of the connector is coaxially aligned with the pierceable seal of the second receptacle;
  actuating the hollow needle to pierce the pierceable seal of the housing of the connector and through the pierceable seal of the second receptacle, thereby connecting the first receptacle and the second receptacle.

This provides the advantage that a first receptacle can be connected, disconnected and reconnected to a second receptacle by a connector. More particularly, the connection, disconnection and reconnection can be achieved in an aseptic, or sterile, manner. Furthermore, the method may be more suited to automated processes and may be easier to handle and use. The method is easy to use, and efficient.

In certain embodiments, the step of actuating the hollow needle comprises fluidly connecting the first receptacle to the second receptacle.

In certain embodiments, the step of actuating the hollow needle comprises fluidly connecting the first receptacle to the second receptacle, thereby forming a communication between the first receptacle and the second receptacle.

In certain embodiments, the step of connecting the distal end to a first receptacle comprises detachably connecting the distal end to the first receptacle.

In certain embodiments, the method further comprises the step of: at least partially rotating an actuating mechanism, thereby causing the hollow needle to pierce the pierceable hermetic seal of the housing of the connector and a pierceable seal of the first receptacle, or the second receptacle, or both the first receptacle and the second receptacle.

In certain embodiments, the method further comprises the step of: at least partially collapsing an upper housing portion of the connector along a central longitudinal axis with respect to a lower housing portion of the connector, thereby causing the hollow needle to pierce the pierceable hermetic seal of the housing of the connector and a pierceable seal of the first receptacle.

In some embodiments, the step of at least partially collapsing the upper housing portion comprises: engaging one or more actuatable lugs of the upper housing portion with an actuating mechanism; and actuating the or each actuatable lug of the upper housing portion so as to collapse the upper housing portion along the central longitudinal axis with respect to the lower housing portion of the connector.

In some embodiments, the step of at least partially collapsing the upper portion of the connector causes the hollow needle to pierce a pierceable hermetic seal of the upper housing portion.

In certain embodiments, the method further comprises the step of: at least partially axially translating the hollow needle along a central longitudinal toward the proximal end of the connector, thereby causing the hollow needle to pierce the pierceable hermetic seal of the housing of the connector and a pierceable seal of the second receptacle.

In some embodiments, the step of at least partially axially translating the hollow needle comprises: engaging one or more actuatable lugs of a collar, operably coupled to the hollow needle, with an actuating mechanism, and actuating the or each actuatable lug of the collar so as to axially translate the collar, and thus the hollow needle, toward the proximal end of the connector.

In some embodiments, the step of at least partially axially translating the hollow needle causes the hollow needle to pierce a pierceable hermetic seal of a lower housing portion.

In certain embodiments, the or each pierceable seal is a pierceable hermetic seal.

In certain embodiments, the or each pierceable hermetic seal comprises a septum seal.

According to yet another aspect of the present disclosure, there is provided a connector as described herein and an actuation system configured to actuate the connector.

In certain embodiments, the actuation system is configured to actuate needle-safe features of the connector, the actuating mechanism acting upon the hollow needle, i.e., to cause piercing of the hollow needle through the or each pierceable seal, and/or the aseptic seal system as described herein. The actuation system may be external to the connector. The actuation system may be formed as part of an instrument, such as an incubator, or the like.

According to yet another aspect of the present disclosure, there is also provided an aseptic coupling arrangement comprising:
  a first aseptic seal system comprising a first clip portion including a first coupling element, and a first aseptic membrane, operably coupled to the first clip portion, disposed over at least a portion of a first pierceable seal;
  a second aseptic seal system comprising a second clip portion including a second coupling element, configured to operably couple to the first coupling element, and a second aseptic membrane, operably coupled to the second clip portion and configured to operably couple to the first aseptic membrane, disposed over at least a portion of a second pierceable seal.

This provides the advantage that two fluid volumes can be aseptically connected and disconnected. In particular, this provides the advantage that two fluid volumes can be aseptically connected and disconnected in a manner that is suitable for automation, for example, suitable for use in an automated cell and/or gene therapy manufacturing process.

In some embodiments, the first aseptic membrane and/or the second aseptic membrane are disposed over most of, or the entirety of, their respective first pierceable seal and/or second pierceable seal.

In some embodiments, the first aseptic seal system and/or the second aseptic seal system comprises an aseptic seal system of a connector, the respective first and/or second pierceable seal being formed as part of the connector. The connector may be the connector as described herein. The first aseptic seal system and/or the second aseptic seal system may be the aseptic seal system of the connector as described herein.

In some embodiments, the first aseptic seal system and/or the second aseptic seal system comprises an aseptic seal system of a container, a bioreactor, an interface plate or the like, the respective first and/or second pierceable seal being formed as part of the container, the bioreactor, the interface plate or the like.

In some embodiments, the first pierceable seal and/or the second pierceable seal comprises a seal as described herein, such as a hermetic seal, a resealable seal, a septum seal, or the like.

In some embodiments, the first aseptic seal system and/or the second aseptic seal system are arranged to be actuated by an actuation system. In some embodiments, upon actuation of the first aseptic seal system and/or the second aseptic seal system, the first aseptic membrane and/or the second aseptic membrane is caused to be removed from the respective first pierceable seal and/or the second pierceable seal.

In some embodiments, the first clip portion is slidably operably coupled to a portion of a component in which the first pierceable seal is arranged. In some embodiments, the second clip portion is slidably operably coupled to a portion of a component in which the second pierceable seal is arranged. In particular embodiments, the first aseptic seal system and/or the second aseptic seal system are arranged to be actuated to slidably move the first clip portion and the second clip portion, thereby removing the first aseptic membrane and the second aseptic membrane from the respective first pierceable seal and the second pierceable seal. In some embodiments, the first aseptic seal system and/or the second aseptic seal system are arranged to be actuated between a first configuration, in which the respective aseptic membranes are at least partially disposed over their respective pierceable seals, and a second configuration, in which the respective aseptic membrane are removed from their respective pierceable seals.

According to yet another aspect of the present disclosure, there is provided a method of operating an aseptic coupling arrangement comprising:
  providing a first aseptic seal system, comprising a first clip portion including a first coupling element, and a first aseptic membrane, operably coupled to the first clip portion, over at least a portion of a first pierceable seal;
  providing a second aseptic seal system, comprising a second clip portion including a second coupling element, and a second aseptic membrane, operably coupled to the second clip portion, over at least a portion of a second pierceable seal;
  operably coupling the first coupling element to the second coupling element;
  operably coupling the first aseptic membrane to the second aseptic membrane;
  actuating the first aseptic seal system and/or the second aseptic seal system, thereby removing the first aseptic membrane from the portion of the first pierceable seal and the second aseptic membrane from the portion of the second pierceable seal to aseptically couple an outer face of the first pierceable seal to an outer face of the second pierceable seal.

This provides the advantage that two fluid volumes can be aseptically connected and disconnected. In particular, this provides the advantage that two fluid volumes can be aseptically connected in a manner that is suitable for automation, for example, suitable for use in an automated cell and/or gene therapy manufacturing process.

In some embodiments, the outer face of the first pierceable seal is urged into an aseptic face-to-face engagement with the outer face of the second pierceable seal.

In some embodiments, the method further comprises disposing of the first aseptic seal system and/or the second aseptic seal system.

In some embodiments, the method further comprises providing a fluid passageway through the first pierceable seal and the second pierceable seal. The fluid passageway may be provided by the connector described herein.

According to yet another aspect of the present disclosure, there is provided a sterile, or an aseptic, connector, for introducing or extracting a material to or from at least one receptacle, comprising:
  a housing extending between a distal end a proximal end, the housing comprising a first pierceable seal at the distal end and a second pierceable seal at the proximal end;
  a hollow needle mounted within the housing between the distal end and the proximal end, a first end of the hollow needle facing the first pierceable seal and being connectable to a first receptacle, and a second end of the hollow needle facing the second pierceable seal and being connectable to a second receptacle; and
  an actuating mechanism acting on the housing or the hollow needle to enable the hollow needle to pierce the first pierceable seal and the second pierceable seal, thereby forming a communication through the pierceable seals, such that material is able to transfer through the sterile connector.

In some embodiments, the sterile connector, or the connector according to any above aspect, forms a sterile communication or a hermetic communication through the pierceable seals, such that material is able to transfer through the sterile connector or connector in a sterile or hermetic manner.

That is, the communication formed through the pierceable seal or seals may be a sterile, i.e., aseptic, or a hermetic, i.e., fluid-tight. Thus, a sterile or hermetic environment is ensured for the material transfer. In some embodiments, the communication is both sterile and hermetic.

According to yet another aspect of the present disclosure, there is provided a sterile package or a sterile container comprising the connector or the sterile connector as described herein.

That is, a sterile, or an aseptic, package or container is provided having the connector or sterile connector packaged therein. The package or container may assume the form of a packet, a receptacle, a box, a bag, or the like. The package or container, and/or the connector or sterile connector, may be sterilized prior to, or following, packaging into the package or container. In some embodiments, the package or container, optionally including the connector or sterile connector, are gamma irradiated prior to, or following, packaging of the connector or sterile connector into the package or container.

This provides the advantage that a fully sterile kit is provided to a user, thus providing a ready-to-use connector in a biological material handling system.

As used herein the term "aseptically attached," "attached in an aseptic tight manner" or "attached in an aseptic manner" is used to describe an aseptic attachment. This includes an attachment that is tight enough to substantially prevent the passage of microbes.

As used herein, the term "axial translation" is used to describe movement parallel or substantially parallel to the longitudinal axis. When used to describe the axial translation of the needle, this describes the possible movement of the needle parallel to the longitudinal axis of the needle and the connector. When the term is used to describe the axial translation of the outer sleeve, or housing, or other element, this is describing the movement of the outer sleeve, the housing of other element in a plane parallel to the longitudinal axis of the connector. The longitudinal axis of the connector extends between the proximal end and the distal end of the connector. The longitudinal axis of the connector extends also between the proximal end and distal end of the housing of the connector.

As used herein, the term "collapse" or "collapsible" is used to describe shortening in length or movement to shorten in length. The terms "collapse" and "collapsible" as used herein also include folding, sliding, turning and rotation that may result in a shortening of length, or height. For example, collapsing of the housing or outer sleeve may include rotation of the housing or outer sleeve such that the height or length of the housing or outer sleeve is reduced. The terms "collapsing" and "collapsible" need not necessarily means folding. The terms "collapsing" and "collapsible" need not necessarily means that the reduction in height or length cannot be undone. The terms "collapsible" and "collapse" as used herein also include partial collapse or collapsing.

As used herein the term "receptacle" is used to describe any vessel or container able to hold a material, for example, a solid or a fluid. The term "receptacle" as used herein includes both hard and soft receptacles, for example, sacks, bags, bellows, bioreactors or vacutainers.

As used herein, the term "double ended hollow needle" is used to describe a hollow needle that is pointed, or sharp, at both ends.

As used herein, the term "material" is used to describe any material. The term "material" includes a solid, or a fluid, or solids, or fluids. The term "material" also includes gases, liquids, solutions, pastes, gels and the like.

As used herein, the term "fluid" is used to describe gas and liquids, including solutions, but also includes granular solids including powders. The granular solids need not be in a solution. Equally, the granular solids may be in a solution, for example, the granular solids may be suspended within a liquid.

As used herein the term "hermetic seal" is used to describe a seal that is fluid tight.

As used herein, the term "partial rotation" is used to describe a partial movement in a rotating manner and direction. It may include all and any amount or distance of the rotation. Specifically, herein it will include a rotation to a desired degree of rotation to, for example, complete a function, for example, to pierce a seal, or releasable attach two items.

As used herein, the term "pierceable seal" is used to describe a seal that can be pierced, for example by a needle.

The term "resealable pierceable seal" is used to describe a seal that is pierceable but also resealable in that once the cause of the pierce is removed, for example, a hollow needle, the seal is able to reseal automatically. The term "pierceable seal" as used herein may be a "resealable pierceable seal."

As used herein the term "to pierce" is used to describe the piercing of a material, such that the piercing element, for example a hollow needle, at least partially, protrudes though the material.

As used herein, the term "self-sealing," in reference to a seal, is used to describe a seal that, after removal of the cause of piercing or rupture, the seal can reseal itself automatically, thus the seal is configured and made of material that enables the opening or rupture to close and reseal.

As used herein the "septum seal" is used to describe a seal that comprises a material that provides an aseptic seal, but the material can also be pierced, for example, by a needle.

As used herein the term "self-sealing aseptic seal" is used to describe an aseptic seal that is capable of resealing after a puncture or piercing from, for example, a hollow needle, to give an aseptic seal again.

Any of the features or steps described herein in relation to one embodiment, aspect or example, of a connector, or of the method for manufacturing a connector, the apparatus (or system) of manufacturing a connector, the components for a connector thereof, or a kit of parts comprising a connector or the manufacturing apparatuses thereof of the method for manufacturing a connector, any of the apparatus (including the system) for manufacturing a component for a connector, a kit of parts comprising a plurality of manufacturing apparatuses suitable for the manufacturing of a connector, or a component for a connector thereof, may be equally applicable to any other embodiment, aspect or example of any connector herein described, any of the method of manufacturing a component for a connector, an apparatus (including the system) for manufacturing a component of a connector, a component thereof, or a kit of parts comprising a plurality of manufacturing apparatuses suitable for the manufacturing of a connector.

Reference will now be made to the drawings, which depict one or more embodiments described in this disclosure. However, it will be understood that other embodiments not depicted in the drawings fall within the scope of this disclosure. Like numbers used in the figures refer to like components, steps and the like. However, it will be understood that the use of a number to refer to a component in a given figure is not intended to limit the component in another figure labeled with the same number. In addition, the use of different numbers to refer to components in different figures is not intended to indicate that the different numbered components cannot be the same or similar to other numbered components. The figures are presented for purposes of illustration and not limitation. Schematic drawings presented in the figures are not necessarily to scale.

BRIEF DESCRIPTION OF THE DRAWINGS

Example embodiments of the disclosure are now described, by way of example only, hereinafter with reference to the accompanying drawings, in which:

FIG. 16 illustrates a cross-sectional view of FIG. 12, where the hollow needle is connected to the first container and the second container;

FIG. 17 illustrates a cross-sectional view of FIG. 12 when connected to the first container and the second container after the fluid connection has been made;

FIG. 18 illustrates a cross-sectional view of FIG. 12 when the connector and the first container are removed from the second container;

FIG. 46 illustrates (a) a top view, (b) a side view, (c) a bottom view, and (d) a cross-sectional view of the components of FIG. 45 including an outer sleeve;

FIG. 52 illustrates (a) a perspective view, and (b) a cross-sectional view of the outer sleeve of the connector of FIG. 51;

FIG. 53 illustrates (a) a perspective view, (b) a bottom view, and (c) a top view of an aseptic seal system for use in the connector of FIG. 51;

FIG. 78 illustrates (a) a perspective view, (b) a top view, and (c) a bottom view of a transit cover for use in the connector of FIG. 63;

FIG. 79 illustrates perspective views of (a) a first step, (b) a second step, (c) a third step, (d) a fourth step, (e) a fifth step, (f) a sixth step, (g) a seventh step, (h) an eighth step, (i) a ninth step, and (j) a tenth step of the assembly of the connector of FIG. 63.

DETAILED DESCRIPTION

Figure 1:
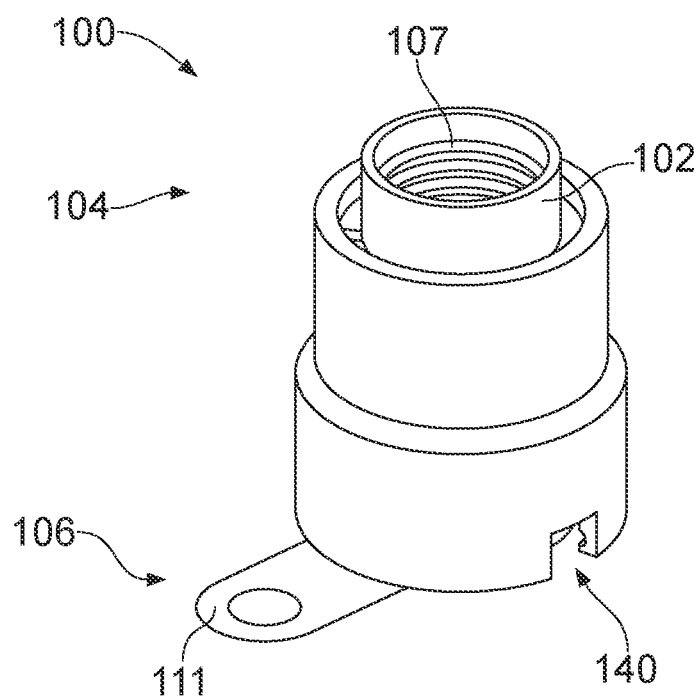
FIG. 1 illustrates a perspective view of a connector according to an embodiment of the present disclosure, including a removable aseptic paper seal.

The described example embodiments relate to a connector for introducing or extracting material to or from at least one receptacle. In particular, some embodiments relate to a connector that is an aseptic connector. It is noted that the terms "aseptic" and "sterile" may be used interchangeably throughout. References to fluids in the detailed description are not intended to limit the scope of protection to such materials. As will be recognized by a person skilled in the art, fluids as described herein are merely an example of a suitable material for use with the described connector. Equally, reference may be made to a container, vacutainer or the like; however, such references in the detailed description are not intended to limit the scope of protection to such receptacles or vessels. As will be recognized by a person skilled in the art, containers, vacutainers or the like are described herein as mere examples of suitable receptacles.

Certain terminology is used in the following description for convenience only and is not limiting. The words "upper" and "lower" designate directions in the drawings to which reference is made and are with respect to the described component when assembled and mounted. The words "inner," "inwardly" and "outer," and "outwardly" refer to directions toward and away from, respectively, a designated centerline or a geometric center of an element being described (e.g., a central axis), the particular meaning being readily apparent from the context of the description. Further, the terms "proximal" (i.e., nearer to) and "distal" (i.e., away from) designate positions relative to an axis or a point of attachment.

Further, as used herein, the terms "connected," "affixed," "coupled" and the like are intended to include direct connections between two members without any other members interposed therebetween, as well as, indirect connections between members in which one or more other members are interposed therebetween. The terminology includes the words specifically mentioned above, derivatives thereof, and words of similar import.

Further, unless otherwise specified, the use of ordinal adjectives, such as, "first," "second," "third," etc., merely indicate that different instances of like objects are being referred to and are not intended to imply that the objects so described must be in a given sequence, either temporally, spatially, in ranking or in any other manner. Like reference numerals are used to depict like features throughout.

Figure 2:
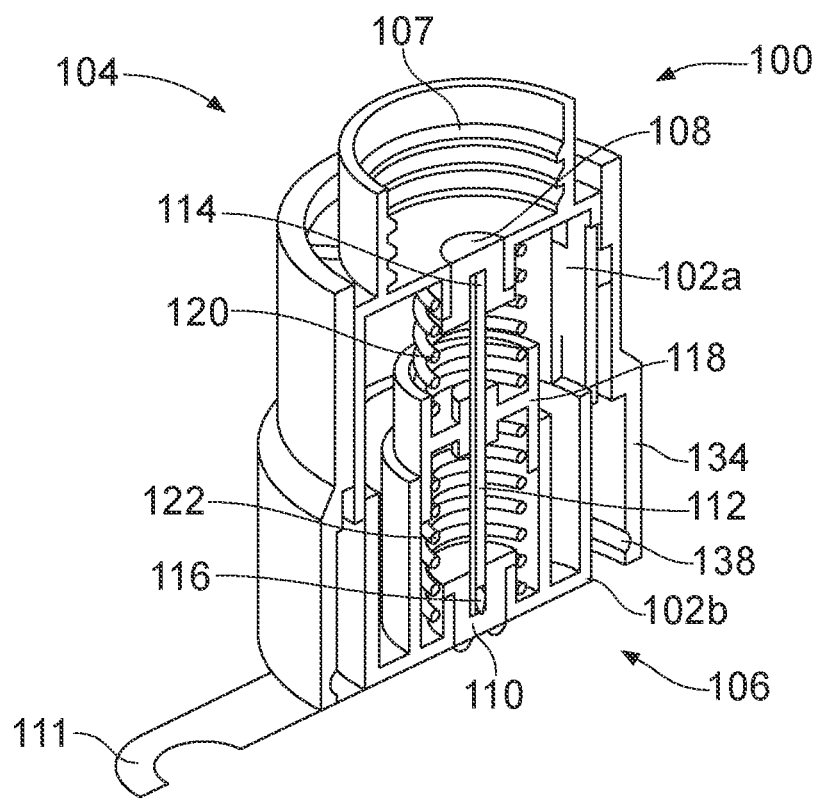
FIG. 2 illustrates a cross-sectional view of the connector of FIG. 1.

As shown in FIGS. 1 and 2, there is provided a connector 100 for connecting two volumes of fluid. The connector 100 includes a housing 102 including an upper housing portion 102a and a lower housing portion 102b. The housing 102 extends along a longitudinal axis between a distal end 104 and a proximal end 106. The upper housing portion 102a may be axially movable, or slidable, with respect to the lower housing portion 102b, as will be described further below.

Figure 3:
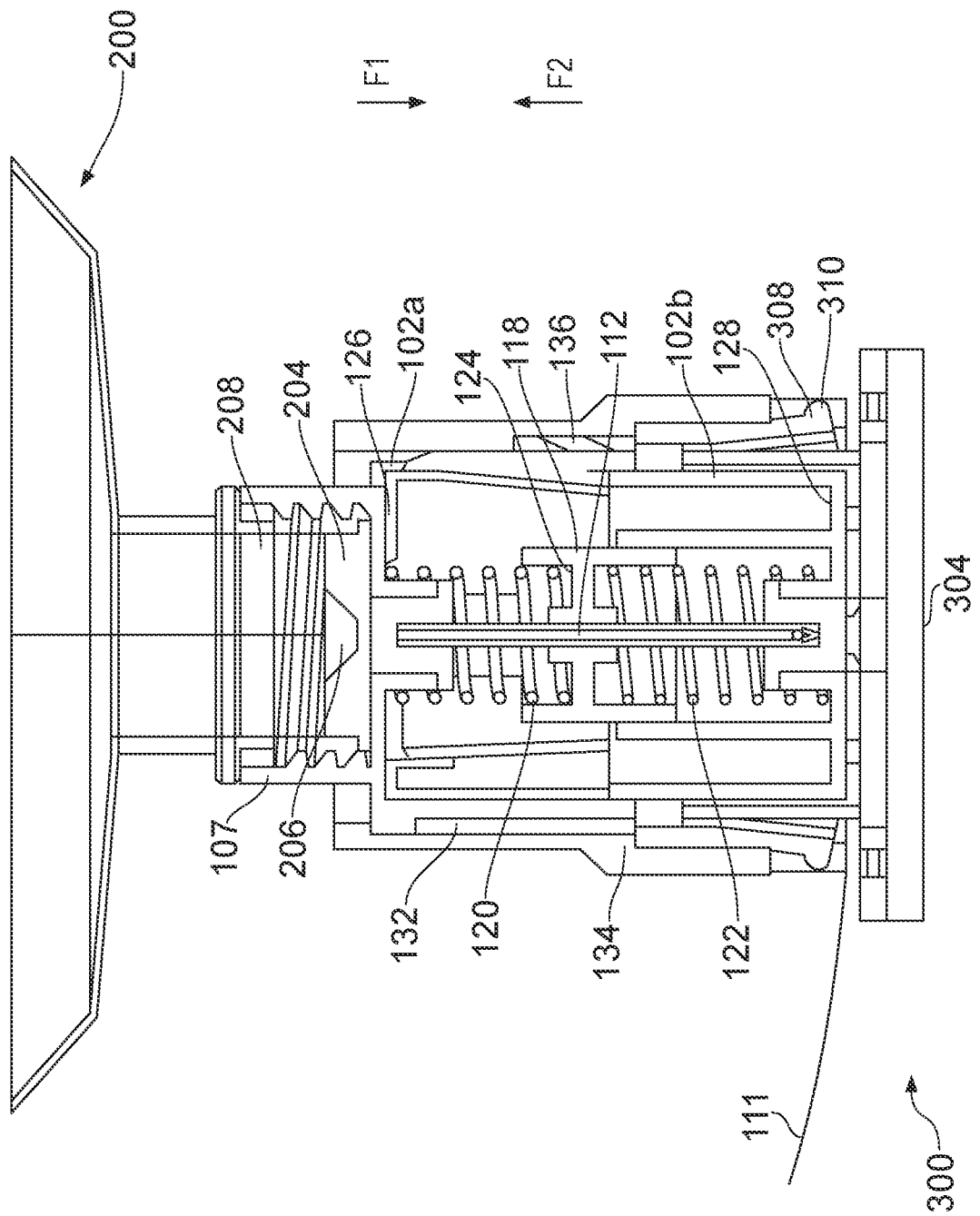
FIG. 3 illustrates a cross-sectional view of the connector of FIG. 1 when connected to a first container and a second container.
Figure 5:
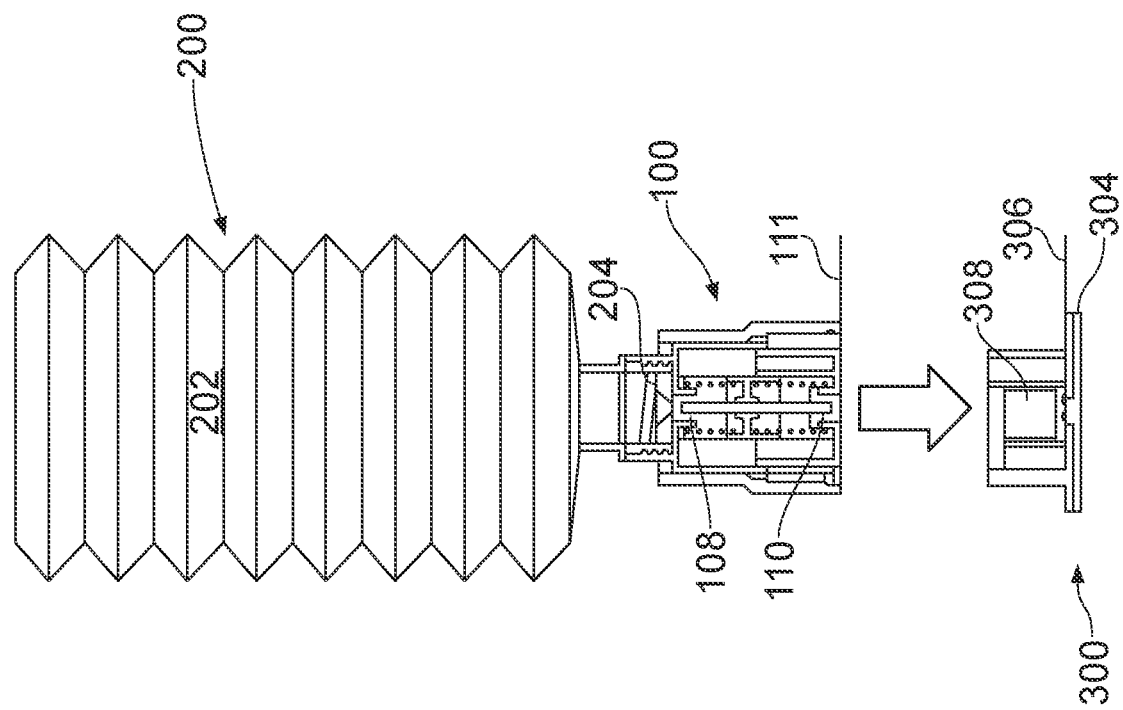
FIG. 5 illustrates a cross-sectional view of the connector of FIG. 1 when connected to a first container, and a second container having another removable aseptic paper seal, prior to assembly to the second container.
Figure 4:
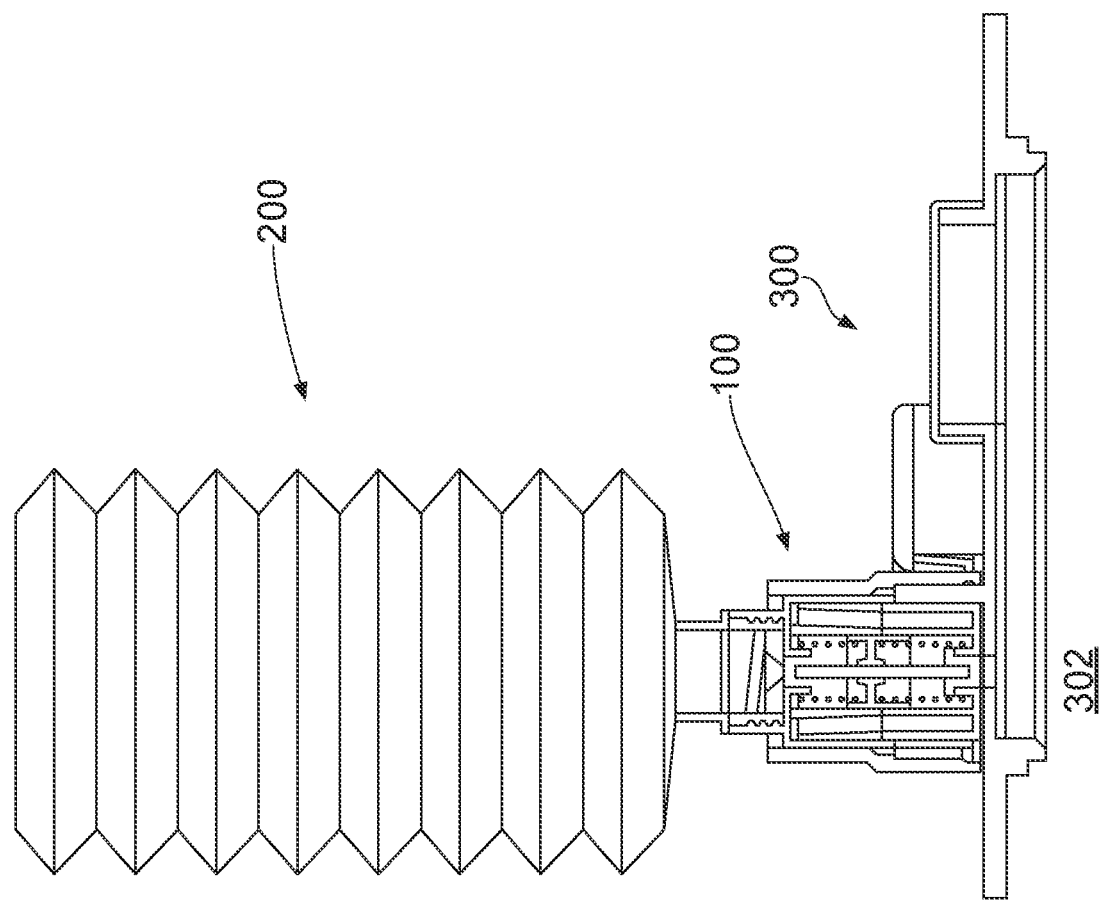
FIG. 4 illustrates another cross-sectional view of FIG. 3.
Figure 7:
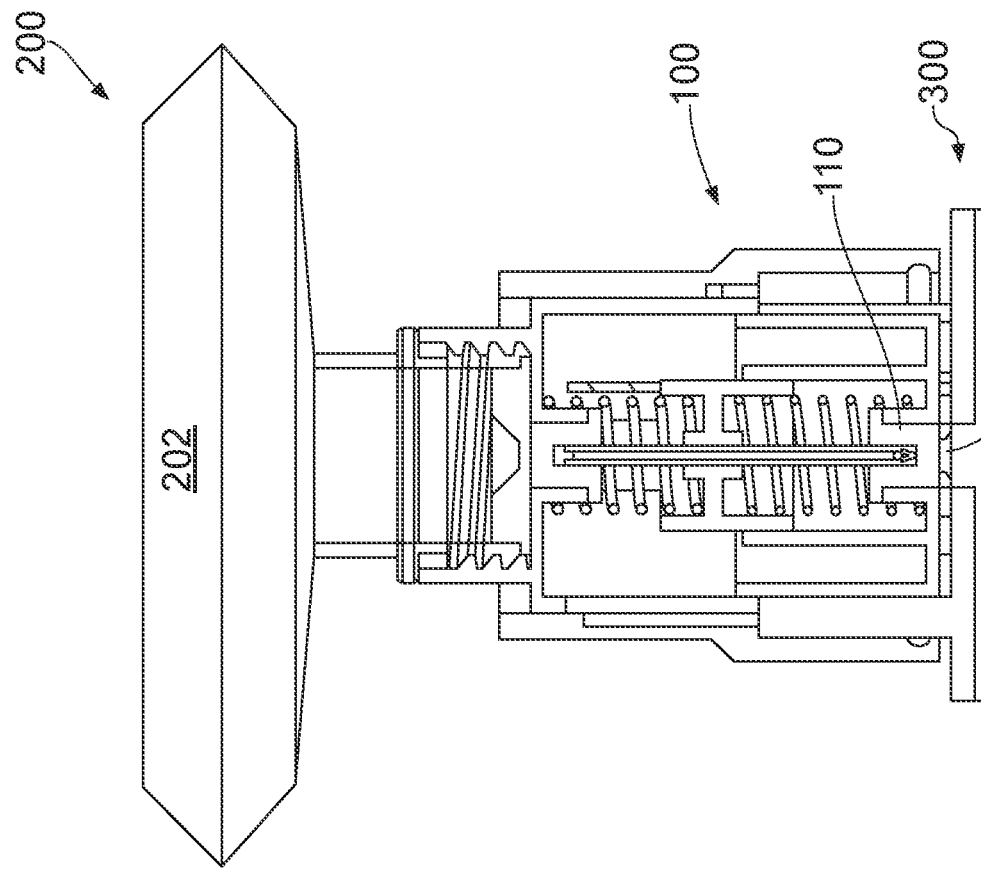
FIG. 7 illustrates a cross-sectional view of the connector of FIG. 1 when connected to a first container and a second container, having the removable aseptic paper seals removed.

The housing 102 includes a threaded portion 107 at its distal end 104 for connecting to a corresponding threaded portion 208 of a first container 200 including a first volume of fluid 202 (see FIGS. 3 and 5). As will be clear to the skilled person, the housing 102 may be provided without the threaded portion 107, and instead be provided with another suitable connection mechanism for connecting to a portion of a container. Further, a first container may be directly attached to the distal end 104 by any suitable mechanism, for example, the container may be pre-connected or sealed, for example, through an adhesive or the like. In some embodiments, the container is manufactured comprising a connector according to the present disclosure.

In this embodiment, the connector 100 includes a first septum seal 108 disposed at the distal end 104 of the housing 102, and a second septum seal 110 disposed at the proximal end 106 of the housing 102. The first septum seal 108 includes a substantially planar, i.e., flat, pierceable surface facing outwardly at the distal end 104. The second septum seal 110 includes a generally annular portion, extending outwardly at the proximal end 106, enclosing a substantially planar, i.e., flat, pierceable surface facing outwardly at the proximal end 106. The housing 102 further includes a hollow needle 112 that is biasedly mounted within the housing 102. The hollow needle 112 is generally coaxially aligned with the longitudinal axis. The hollow needle 112 includes a first end 114, facing the first septum seal 108, and a second end 116, facing the second septum seal 110. The first end 114 is configured to be able to pierce the first septum seal 108, in use, and the second end 116 is configured to be able to pierce the second septum seal 110, in use. The first septum seal 108, the second septum seal 110, or both the first and second septum seal 108, 110 may optionally be provided with a removable aseptic paper seal 111.

The hollow needle 112 is mounted within the housing 102 through a collar 118 that is spring-biased by a first helical spring 120 and a second helical spring 122. In other embodiments, the hollow needle 112 may be mounted in another suitable manner, for example, the hollow needle 112 may be statically mounted, i.e., such that it does not move, and the housing 102 may be movable about the hollow needle 112. With further reference to FIG. 3, the collar 118 includes an upper surface 124, facing an inner surface 126 of the distal end 104 of the housing 102, and a lower surface 128, facing an inner surface 130 of the proximal end 106 of the housing 102. The collar 118 engages with the hollow needle 112 through any appropriate engagement mechanism, for example, a friction-fit through bore as shown. The first spring 120 extends from the inner surface 126 of the distal end 104 of the housing 102 to the upper surface 124 of the collar 118. The second spring 122 extends from the inner surface 130 of the proximal end 106 of the housing 102 to the lower surface 128 of the collar 118. In this way, the first spring 120 provides a first biasing force F1 to the hollow needle 112, via the collar 118, in a direction toward the proximal end 106 of the housing 102, and the second spring 122 provides a second biasing force F2 to the hollow needle 112, via the collar 118, in a direction toward the distal end 104 of the housing 102.

As best shown in FIG. 3, the first helical spring 120 includes a wire diameter, i.e., a thickness of the material from which the helical spring is formed, that is greater than a wire diameter of the second helical spring 122. In this way, the first spring 120 imparts a greater biasing force than the second spring 122. That is, the first biasing force F1 is larger than the second biasing force F2. In other examples, the first spring 120 may have an outer diameter, i.e., the diameter of the spring itself, that is greater than an outer diameter of the second spring 122, thereby providing a first biasing force F1 that is greater than the second biasing force F2. Alternatively, in other embodiments, the first spring 120 and the second spring 122 may have equal biasing forces, or the second spring 122 may have a greater biasing force than the first spring 120. In examples where one of the first biasing forces and the second biasing forces is greater than the other, i.e., non-equal, the hollow needle 112 is caused to pierce one of the first septum seal 108 and the second septum seal 110 first, and then the other of the first septum seal 108 and the second septum seal 110. In this way, non-equal first and second biasing forces provide sequential piercing of septa, as described in more detail below.

As will be appreciated by the skilled person, other suitable biasing mechanisms may be used. In some examples, the or both helical springs 120, 122 may be resilient or non-resilient. In other examples, a deformable material or another type of spring may be provided in place of one or both helical springs 120, 122, for example an elastomeric material. The or each deformable material may be provided in the form of a bellows. The or each deformable material may be resilient or non-resilient. Any combination may be used.

Referring to FIGS. 1 to 3, the connector 100 further includes an actuating mechanism 132 for causing the hollow needle 112 to pierce the septum seals 108, 110. The actuating mechanism 132 includes an outer sleeve 134 that is arranged to collapse the upper housing portion 102*a* with respect to the lower housing portion 102*b*. The outer sleeve 134 is rotatable with respect to the housing 102 about the central longitudinal axis of the housing 102. More specifically, the outer sleeve 134 includes a rail 136 that is arranged to engage with a protrusion (not shown) on the upper housing portion 102*a*. As the outer sleeve 134 is rotated, the protrusion is guided by the rail 136, thereby converting a rotation of the outer sleeve 134 into axial translation, i.e., collapsing, of the upper housing portion 102*a*. As described further below, this causes the springs 120, 122 to compress and cause the hollow needle 112 to pierce the septum seals 108, 110. The outer sleeve 134 may also include a circumferential groove 138 at its proximal end. The circumferential groove 138 is configured to receive one or more protrusions 310 on one or more legs 308 of a second container 300, to provide a releasable locking engagement with the second container, as described below. The circumferential groove 138 may receive one or more protrusions 310 by a snap mechanism. The outer sleeve 134 may also include one or more apertures 140 that allow the user to release the or each leg 308 of the second container 300, thereby releasing the releasable locking engagement.

Referring to FIGS. 1 to 11, particularly FIGS. 3 to 11, a method of using the connector 100 is now described. The connector 100 is first coupled to a first container 200 containing a first volume of fluid 202 and a septum seal 204. The septum seal 204 may include a central frustoconical depression 206. The first container 200 may take the form of a bellows, which is a container having a distal end, a proximal end, and corrugated, or Z-folded, walls therebetween. In other examples, the first container 200 may take the form of a vacutainer or a lid, i.e., an interface plate between the connector 100, the first container 200 and another container.

The first container 200 may be detachably coupled, or permanently coupled, to the distal end 104 of the connector 100. In the depicted example, the first container 200 includes a threaded portion 208 that threadedly engages with the threaded portion 107 at the distal end 104 of the housing 102 of the connector 100. In this way, the septum seal 204 of the first container 200 abuts the first septum seal 108 of the connector. In some examples, the first container 200 may include a removable aseptic paper seal (not shown) disposed over the septum seal 204 that is arranged to engage with a removable aseptic paper seal (not shown) disposed over the first septum seal 108 of the connector. In such examples, once the connection between the connector 100 and the second container 300 is made, the aseptic paper seals may be removed by pulling a pull tab on each of the respective aseptic paper seals, thereby providing an aseptic abutment between the septum seal 204 of the first container 200 and the first septum seal 108 of the connector.

Once the connector 100 is coupled to the first container 200, the connector 100 may then be connected to a second container 300 containing a second volume of fluid 302. The second container 300 may take the form of a container or a bellows as described above, a lid, i.e., an interface plate between the connector 100, the first container 200 or another container, or the like. In the depicted example, the second container 300 takes the form of a lid that is connected or connectable to a container, for example, a bioreactor (not shown). The second container 300 includes a septum seal 304 having a removable aseptic paper seal 306 disposed thereon. Additionally, the second container 300 includes a plurality of legs 308, each leg 308 having a protrusion 310.

Figure 6:
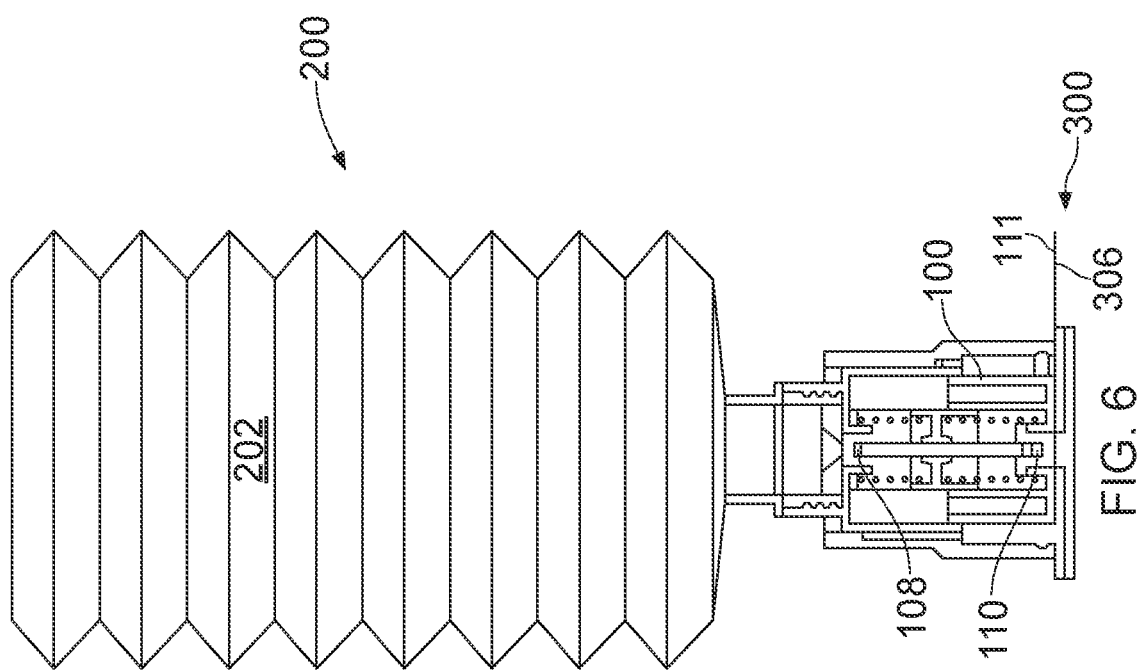
FIG. 6 illustrates a cross-sectional view of the connector of FIG. 1 when connected to a first container and a second container.
Figure 8:
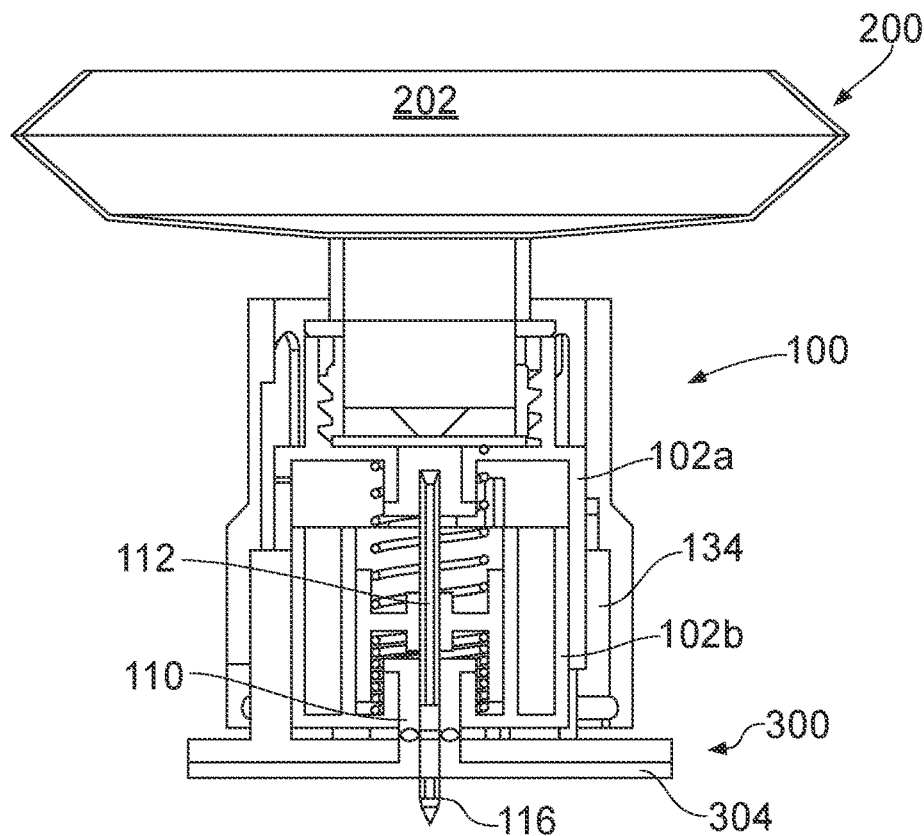
FIG. 8 illustrates a cross-sectional view of the connector of FIG. 1 when connected to a first container and a second container, where the hollow needle is connected to the second container.
Figure 9:
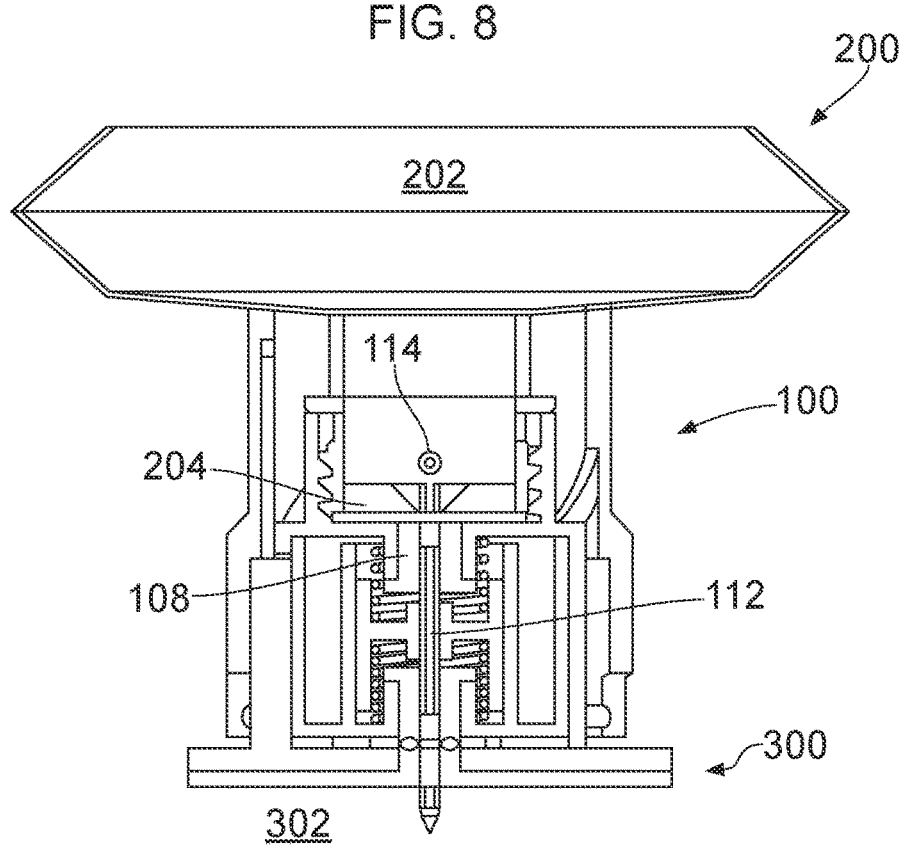
FIG. 9 illustrates a cross-sectional view of the connector of FIG. 1 when connected to a first container and a second container, where the hollow needle is connected to the first container and the second container.
Figure 10:
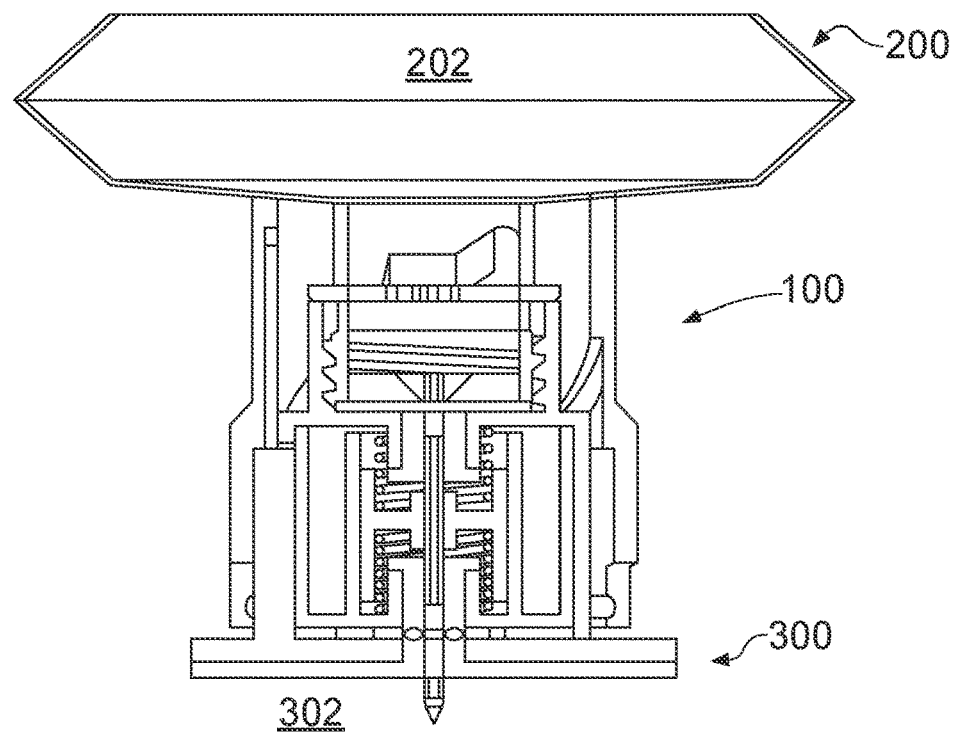
FIG. 10 illustrates another view of FIG. 9, in which fluid can be transferred between the first container and the second container.

The connector 100 is detachable coupled to the second container 300 by a snap engagement with the protrusion 310 on each leg 308 into the circumferential groove 138 of the outer sleeve 134. One or more of the legs 308 are exposed through the apertures 140 of the outer sleeve 134, thereby allowing for release of the protrusions 310 from the circumferential groove 138 after use. During the detachable coupling of the second container 300 with the connector 100, the removable aseptic paper seal 111 of the connector 100 engages the removable aseptic paper seal 306 of the second container 300. Once the second container 300 has engaged with the outer sleeve 134, the removable aseptic paper seals 111, 306 are removed by pulling a pull tab, or handle, of each aseptic paper seal 111, 306. In this way, an aseptic abutment is provided between the second septum seal 110 of the connector 100 and the septum seal 304 of the second container 300, as shown in FIG. 6. The connector 100 is then ready to provide fluid communication between the first volume of fluid 202 and the second volume of fluid 302.

Referring particularly to FIGS. 8 to 11, the outer sleeve 134 of the connector 100 is rotated about the longitudinal axis of the housing 102. The rotation of the outer sleeve 134 causes the upper housing portion 102*a* to collapse in an axial direction toward, and within, the lower housing portion 102*b*. In this way, the hollow needle 112 is first caused to pierce the second septum seal 110 as the biasing force of the first spring 120 is greater than the biasing force of the second spring 122. In other words, the second spring 122 is compressed to a greater extent, or more easily, than the first spring 120, thus allowing the hollow needle 112 to firstly pierce the second septum seal 110 of the connector 100. Continual rotation of the outer sleeve 134 causes the second end 116 of hollow needle 112 to pierce the second septum seal 110 of the connector 100, into and then through the septum seal 304 of the second container 300. In this way, the second end 116 of the hollow needle 112 is fluidly connected to the second container 300.

As the outer sleeve 134 of the connector 100 is continually rotated about the longitudinal axis of the housing 102, the hollow needle 112 is caused to pierce the first septum seal 108 as the first spring 120 is caused to compress. In other words, the first end 114 of the hollow needle 112 is forced through the first septum seal 108 as the first spring 120 is forced to compress, since the second spring 122 is already fully compressed by virtue of the differing biasing forces. Continual rotation of the outer sleeve 134 causes the first end 114 of the hollow needle 112 to pierce the first septum seal 108 of the connector 100, into and then through the septum seal 204 of the first container 200. In this way, the first end 114 of the hollow needle 112 is fluidly connected to the first container 200, thereby fluidly connected the first container 200, including the first volume of fluid 202, to the second container 300, including the second volume of fluid 302.

The fluid within the first volume of fluid 202 may then be introduced into the second volume of fluid 302. Additionally, or alternatively, the fluid within the second volume of fluid 302 may then be introduced into the first volume of fluid 202.

In other examples where the second biasing force F2, of the second spring 122, is greater than the first biasing force F1, of the first spring 120, the septa 108, 110 are pierced sequentially in the opposite order. That is, the first septum seal 108 would be pierced first, thus firstly fluidly connecting the first container 200, followed by a piercing of the second septum seal 110, thus secondly fluidly connecting the second container 300.

Figure 11:
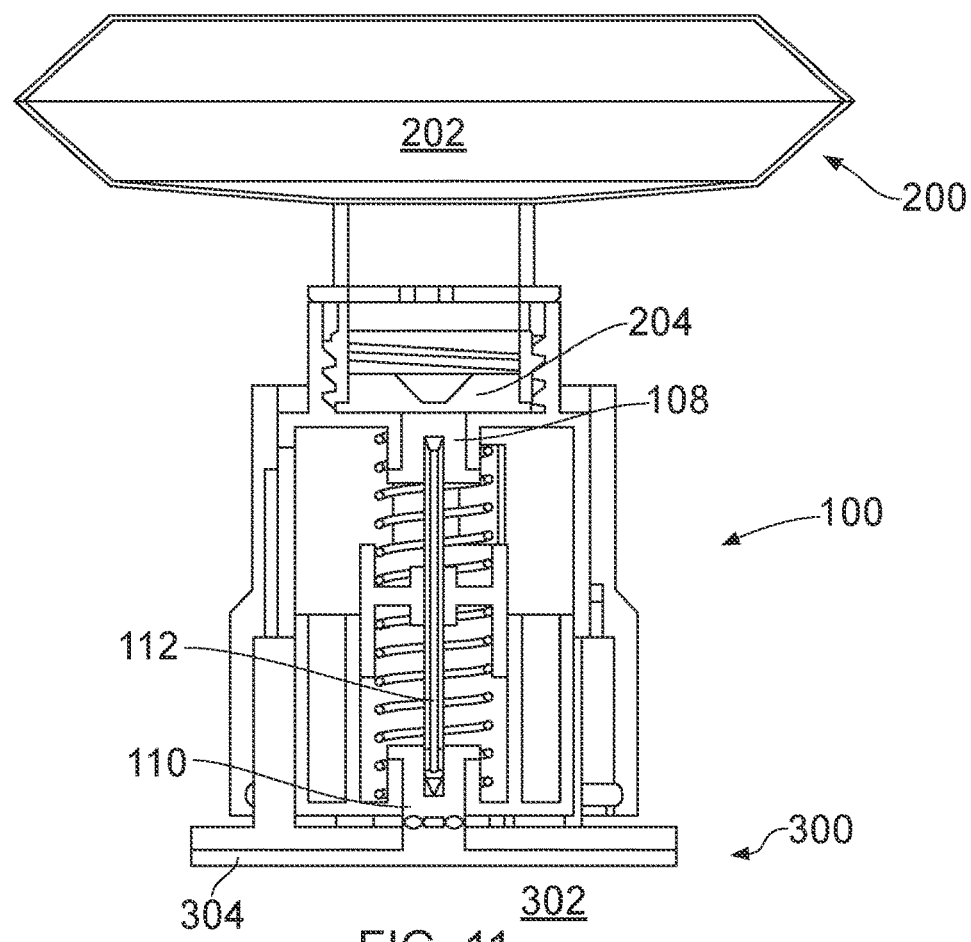
FIG. 11 illustrates a cross-sectional view of the connector of FIG. 1 when connected to a first container and a second container after the fluid connection has been made.
Figure 12:
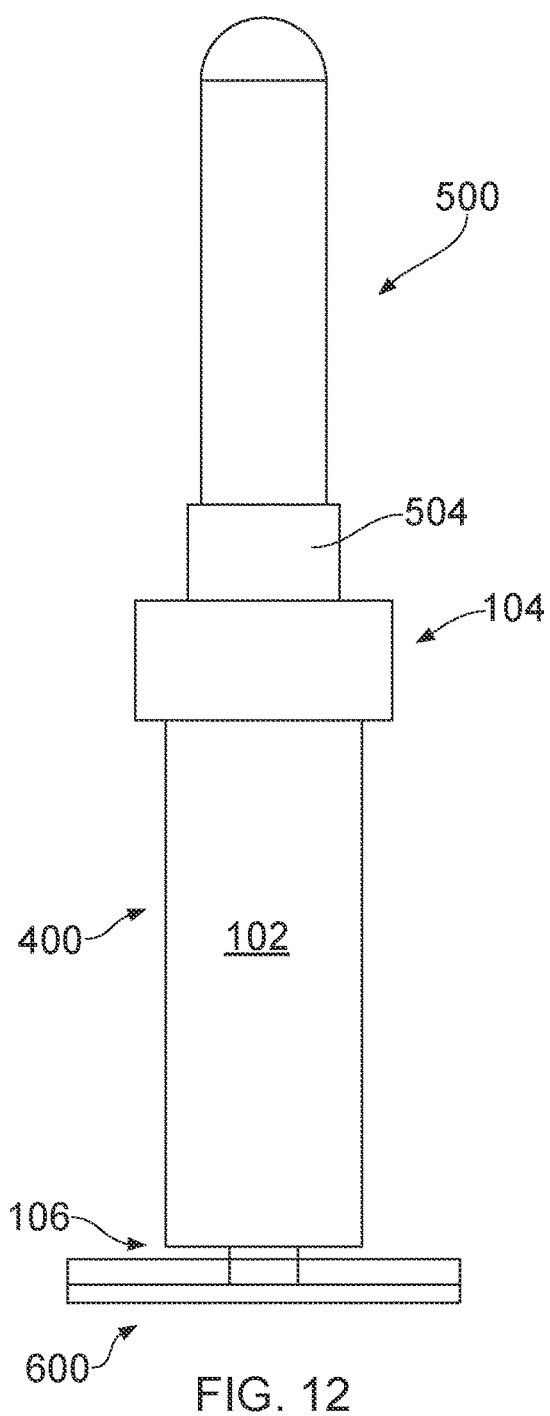
FIG. 12 illustrates a side view of a connector according to another embodiment of the present disclosure, when connected to a first container and a second container.
Figure 13:
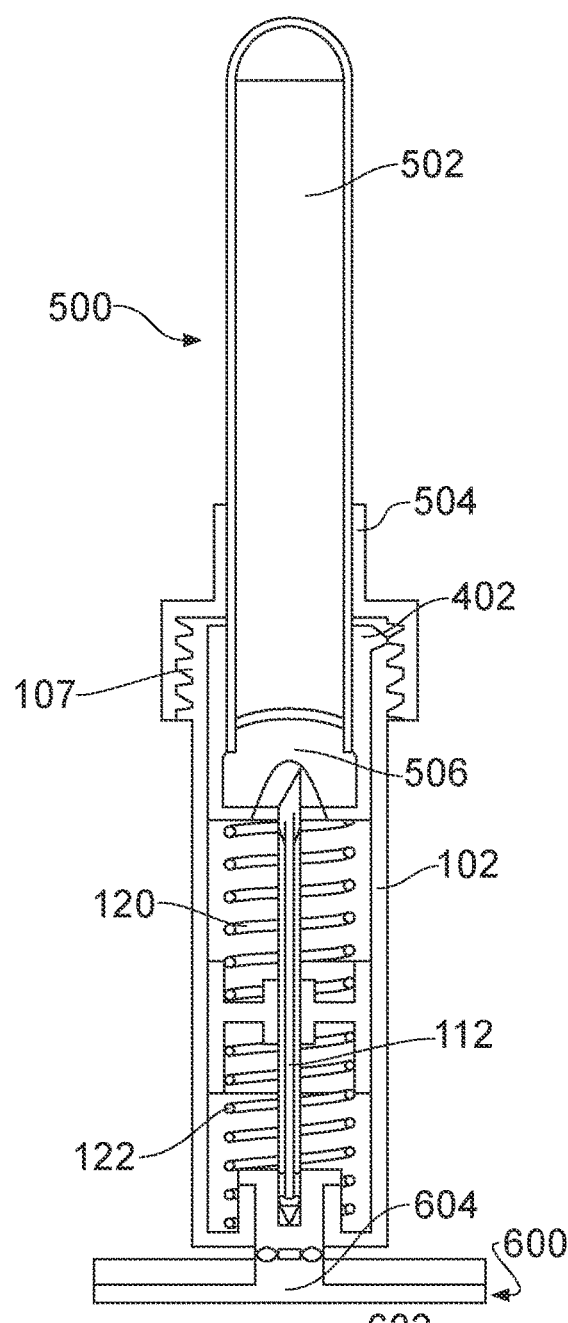
FIG. 13 illustrates a cross-sectional view of FIG. 12.

In order to remove the fluid connection between the two fluid volumes, the method is followed in reverse. That is, the outer sleeve 134 is rotated in the opposite direction, such that the hollow needle 112 is retracted firstly from the first container 200 and the first septum seal 108, and then from the second container 300 and the second septum seal 110, as shown in FIG. 11. The connector 100 can then be removed by pressing the legs 308 to remove the protrusions 310 from the circumferential groove 138 of the outer sleeve 134.

As shown in FIGS. 12 to 18, there is provided another embodiment of a connector 400 for fluidly connecting two volumes of fluid. The connector 400 is particularly suitable for quick sampling of a volume of fluid. The connector 400 is the same as the construction of connector 100 except for the details listed below. Like reference numerals denote like features.

The connector 400 includes a housing 102 and does not include the outer sleeve 134 as described in relation to the first connector 100. However, in some examples, the outer sleeve 134 may be present, or the elements thereof may be formed as part of an outer surface of the housing 102.

The housing 102 additionally comprises an axially movable cap 402 at the distal end 104 of the housing 102. The cap 402 serves to maintain a sterile environment within the housing 102. The cap 402 may include a pierceable, breakable or septum seal (not shown) which allows the hollow needle 112 to pierce therethrough but maintains a sterile environment. The cap 402 is axially movable along the longitudinal axis of the connector 400, that is, it may be collapsible, or slidable, with respect to the housing 102.

The connector 400 is used in a similar manner to that described in relation to connector 100. Firstly, the connector 400 is connected to a first container 500, depicted as a vacutainer in this embodiment, having a first volume of fluid 502. The first container 500 includes a threaded outer sleeve 504 and a septum seal 506. The first container 500 is inserted within the cap 402, and the threaded outer sleeve 504 is threadedly engaged with the threaded portion 107 of the housing 102.

Once the first container 500 is connected to the connector 400 at the distal end 104, the connector 400 is connected at its proximal end 106 to a second container 600. In the depicted embodiment, the second container 600 is a lid that is connected or connectable to a bioreactor (not shown) having a second volume of fluid 602 and a septum seal 604. The connector 400 and the second container 600 can be connected in any suitable manner, including in the way described in relation to connector 100 and the second container 300 above.

Figure 14:
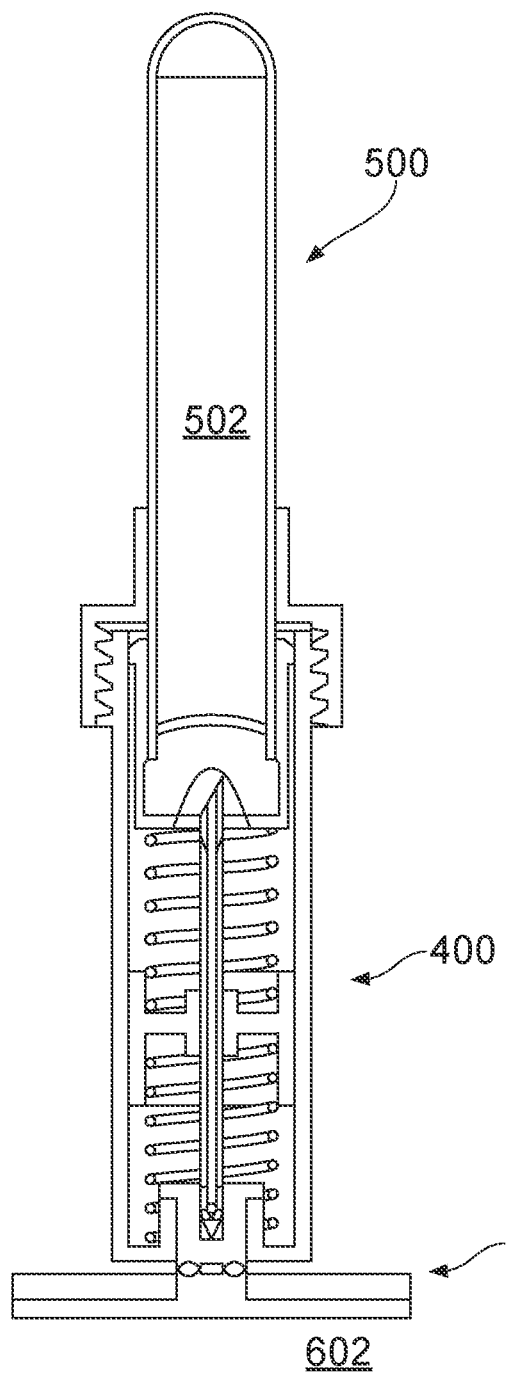
FIG. 14 illustrates a cross-sectional view of FIG. 12 when connected to a first container and a second container before a fluid connection is made.
Figure 15:
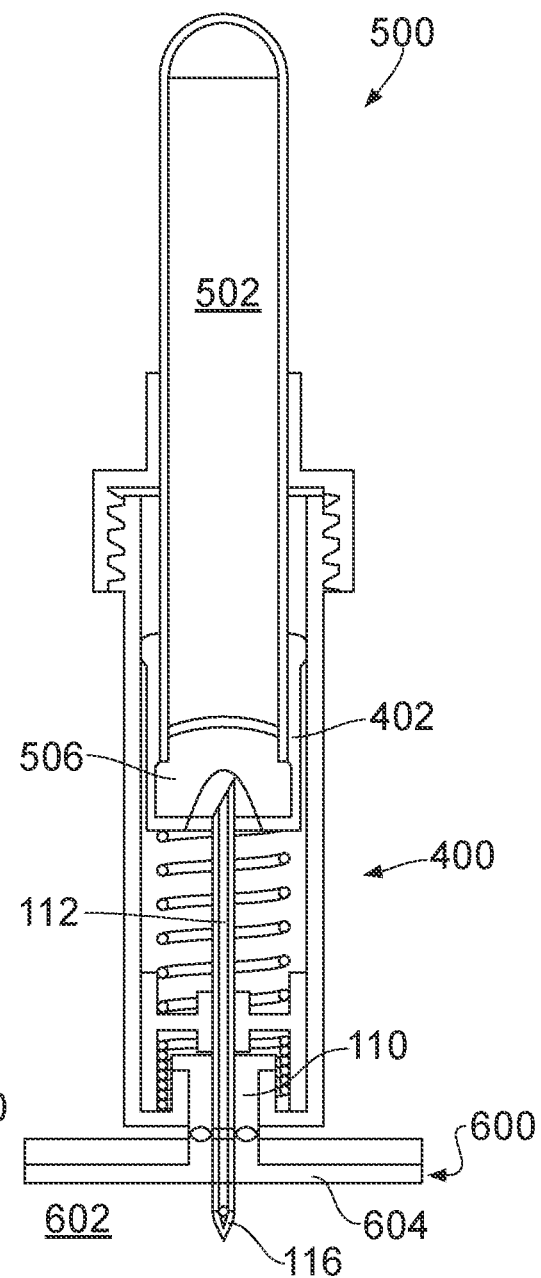
FIG. 15 illustrates a cross-sectional view of FIG. 12, where the hollow needle is connected to the second container.

Once the connector 400, the first container 500 and the second container 600 are connected, as shown in FIG. 14, the first container 500 is axially moved, i.e., pushed, toward the second container 600. In this way, as described above, the hollow needle 112 first pierces the second septum seal 110 of the housing 102 and the septum seal 604 of the second container 600, as shown in FIG. 15. Thus, the second end 116 of the hollow needle 112 is fluidly connected to the second volume of fluid 602.

As the first container 500 is continually pushed toward the second container 600, the hollow needle 112 is caused to pierce the septum seal of the cap 402 and the septum seal 506 of the first container 500, as shown in FIG. 16. In doing so, the first end 114 of the hollow needle 112 is fluidly connected to the first volume of fluid 502, thereby fluidly connecting the first volume of fluid 502 to the second volume of fluid 602.

Once the operation is complete, and as shown in FIGS. 17 and 18, the user ceases to apply pressure to the first container 500, i.e., ceases to push the first container 500, so that the connector 400 may be removed from the second container 600.

Additionally, or alternatively, in some examples, the connector 400 may be disengaged from the connection mechanism on the second container 600. The first container 500 can then be removed from the connector 400 by unscrewing the threaded outer sleeve 504 of the first container from the connector 400.

Although the embodiment of FIGS. 12 to 18 utilizes two springs as part of the actuation mechanism, it will be apparent to persons skilled in the art that such an actuation mechanism could be replaced by any other actuation mechanism discussed herein, particularly those discussed in the embodiments described below.

As shown in FIGS. 19 to 27, there is provided another embodiment of a connector 700 for connecting two volumes of fluid. The connector 700 is the same construction as connector 100, described in relation FIGS. 1 to 11, except for the details listed below. Like reference numerals denote like features.

Figure 21:
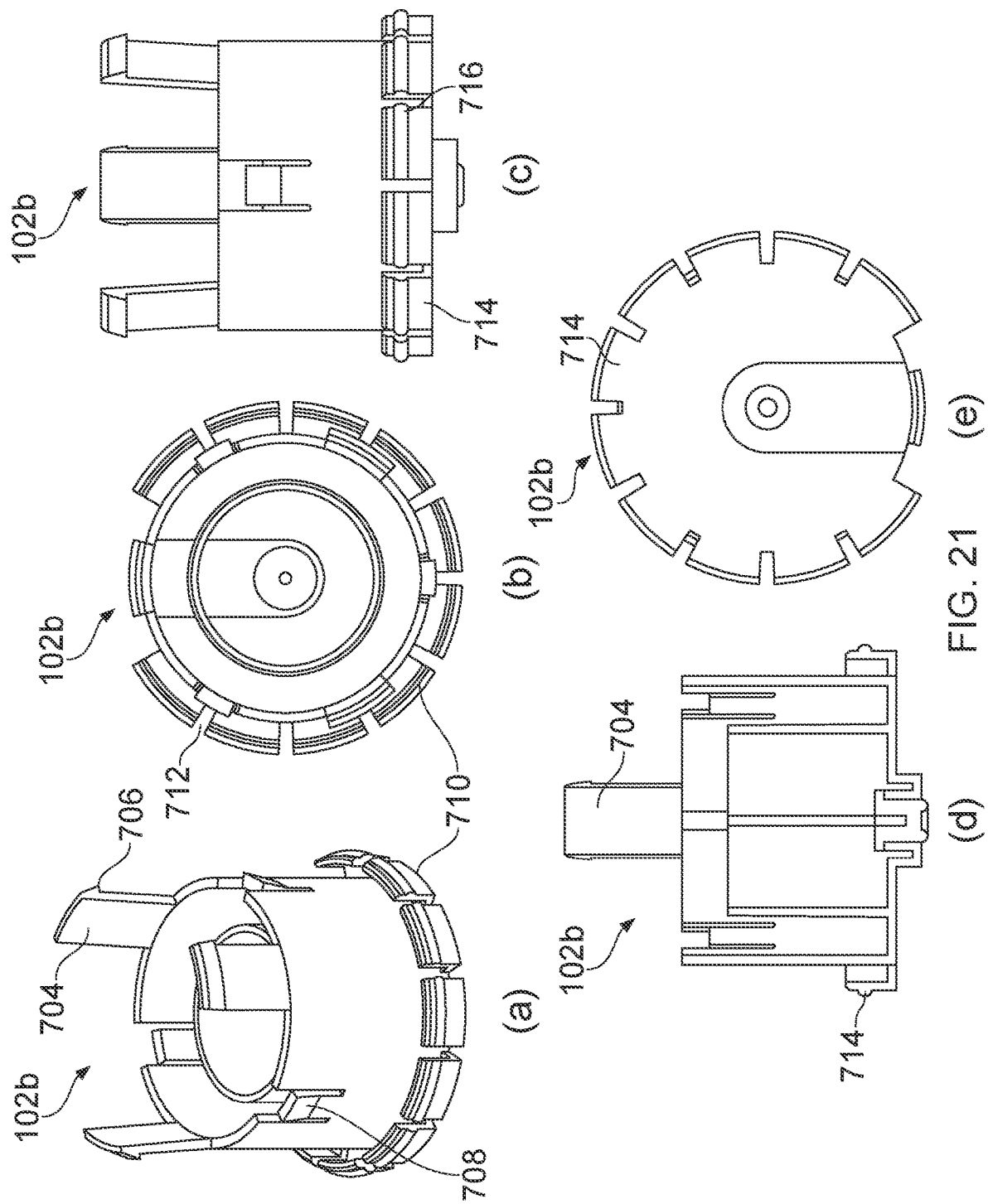
FIG. 21 illustrates (a) a perspective view, (b) a top view, (c) a side view, (d) a cross-sectional view, and (e) a bottom view of the lower housing portion of the connector of FIG. 19.
Figure 22:
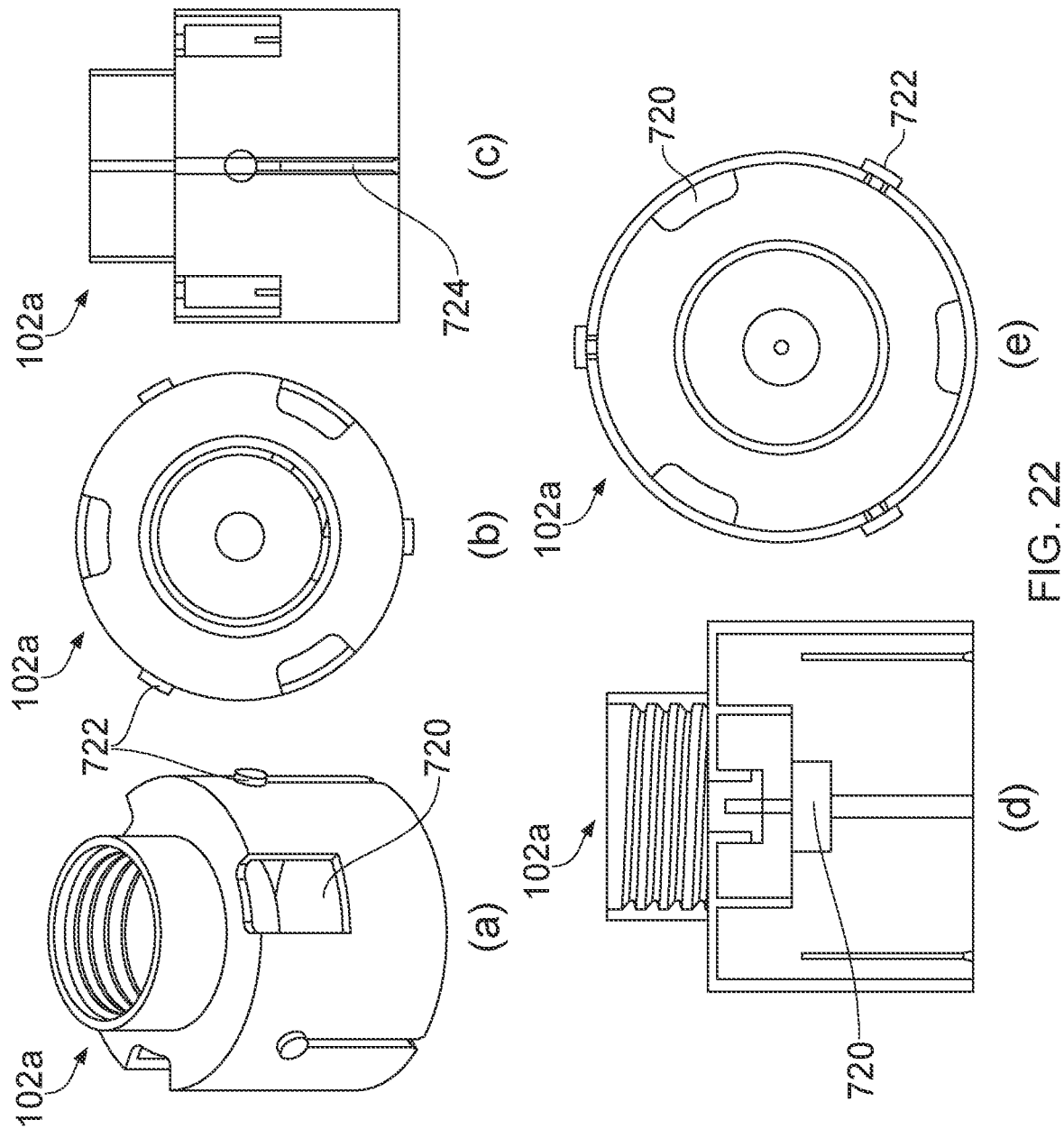
FIG. 22 illustrates (a) a perspective view, (b) a top view, (c) a side view, (d) a cross-sectional view, and (e) a bottom view of the upper housing portion of the connector of FIG. 19.
Figure 23:
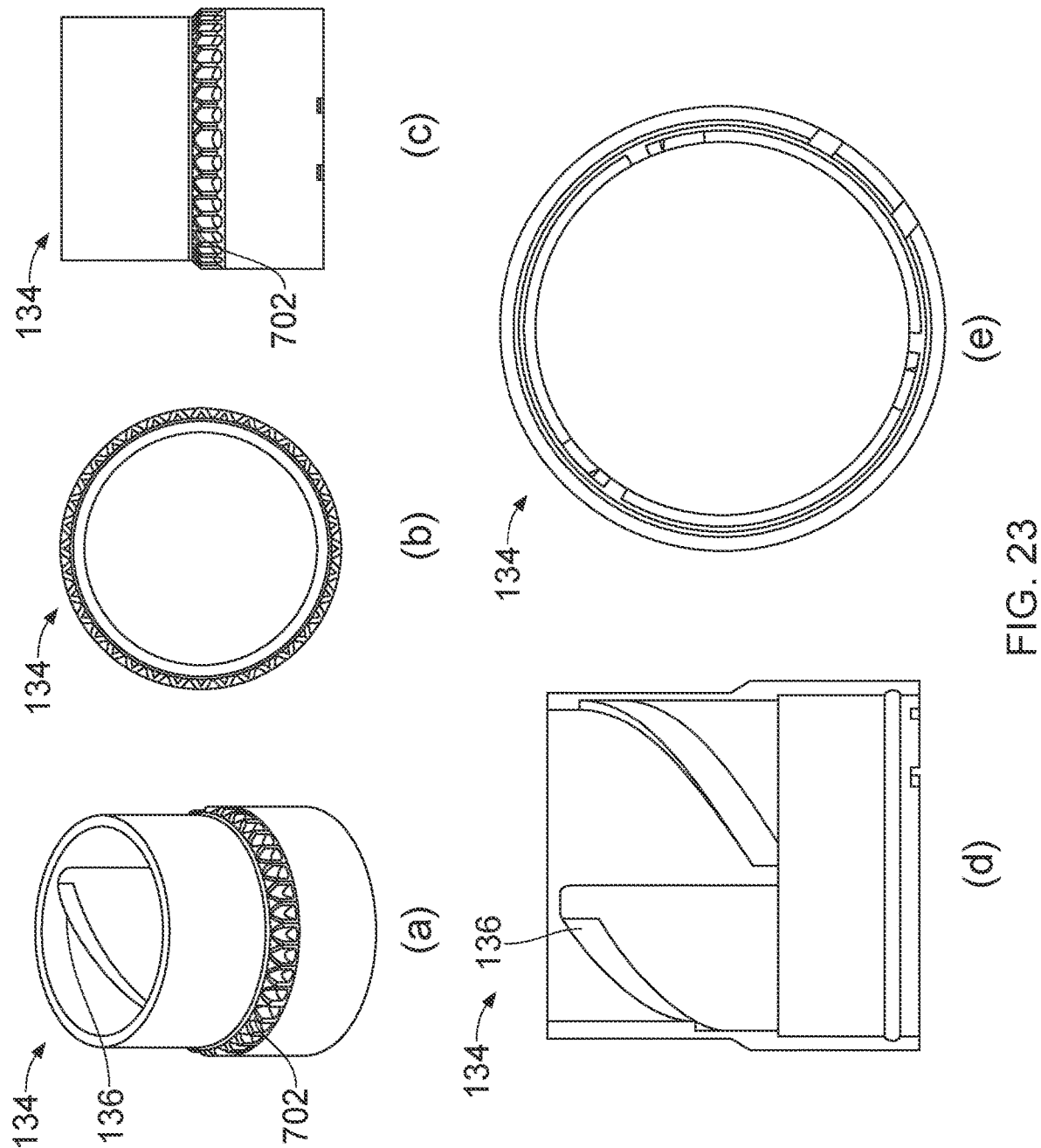
FIG. 23 illustrates (a) a perspective view, (b) a top view, (c) a side view, (d) a cross-sectional view, and (e) a bottom view of the outer sleeve of the connector of FIG. 19.
Figure 24:
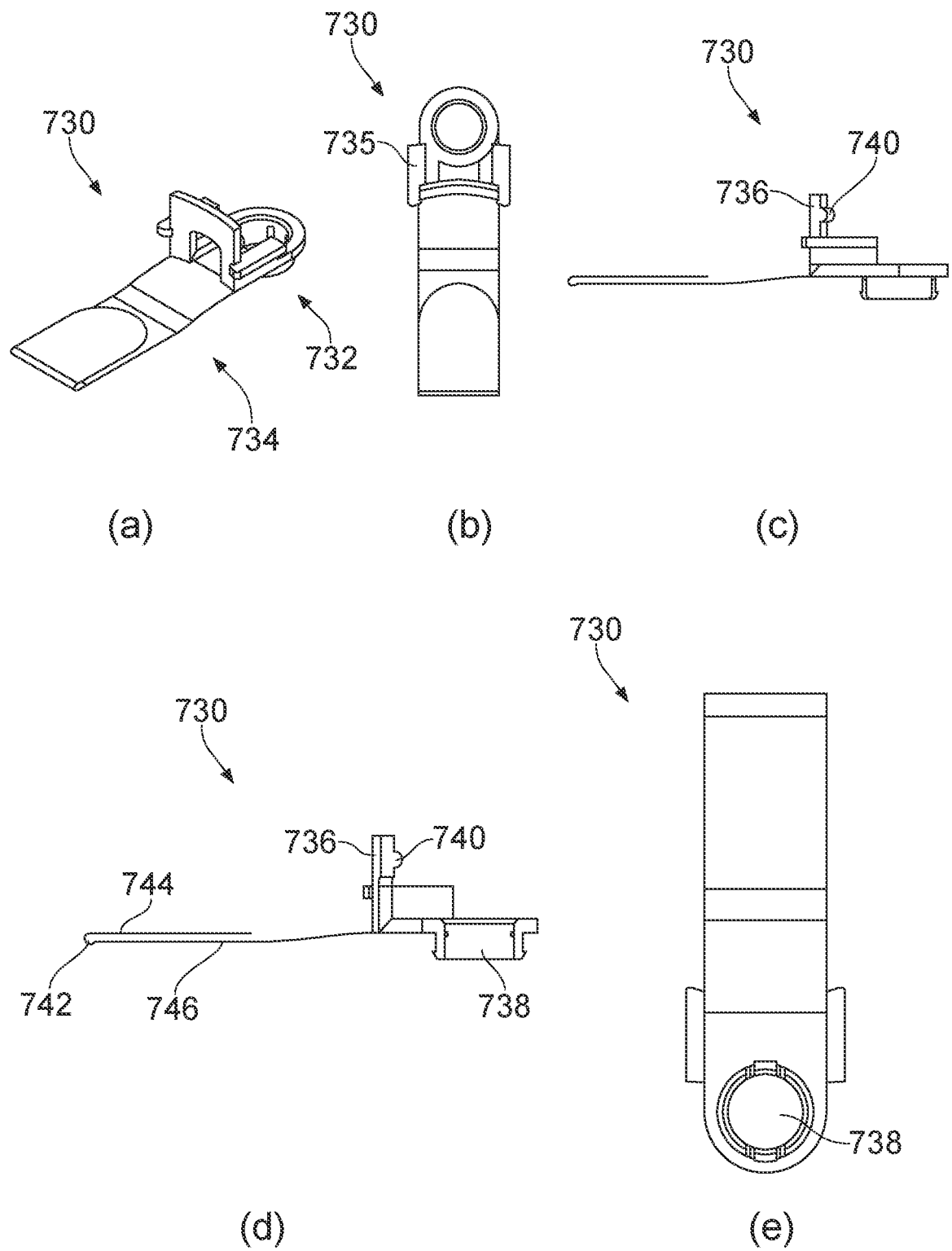
FIG. 24 illustrates (a) a perspective view, (b) a top view, (c) a side view, (d) a cross-sectional view, and (e) a bottom view of an aseptic sealing system for use with the connector of FIG. 19.
Figure 25:
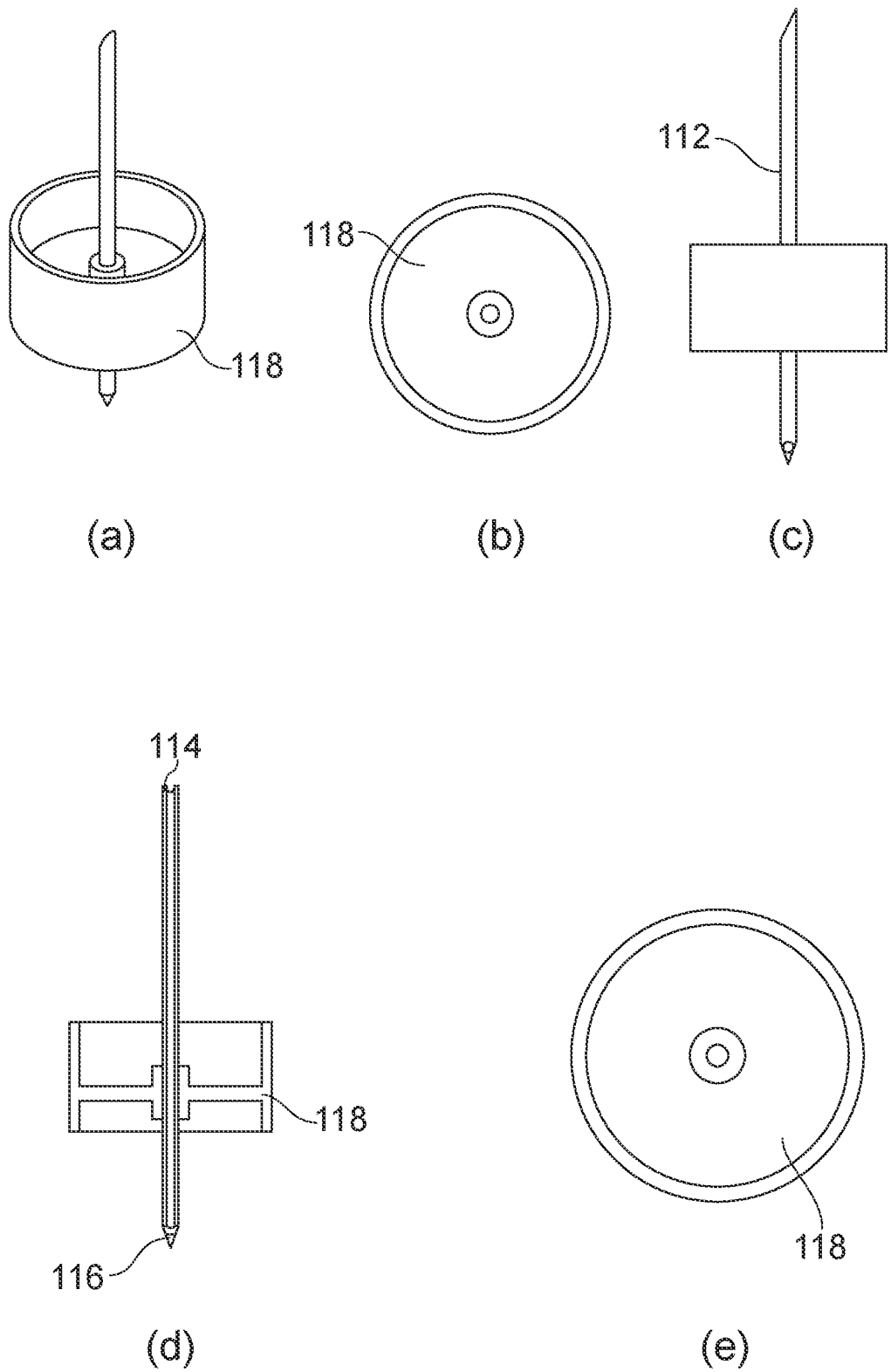
FIG. 25 illustrates (a) a perspective view, (b) a top view, (c) a side view, (d) a cross-sectional view, and (e) a bottom view of the collar of the connector of FIG. 19.
Figure 26:
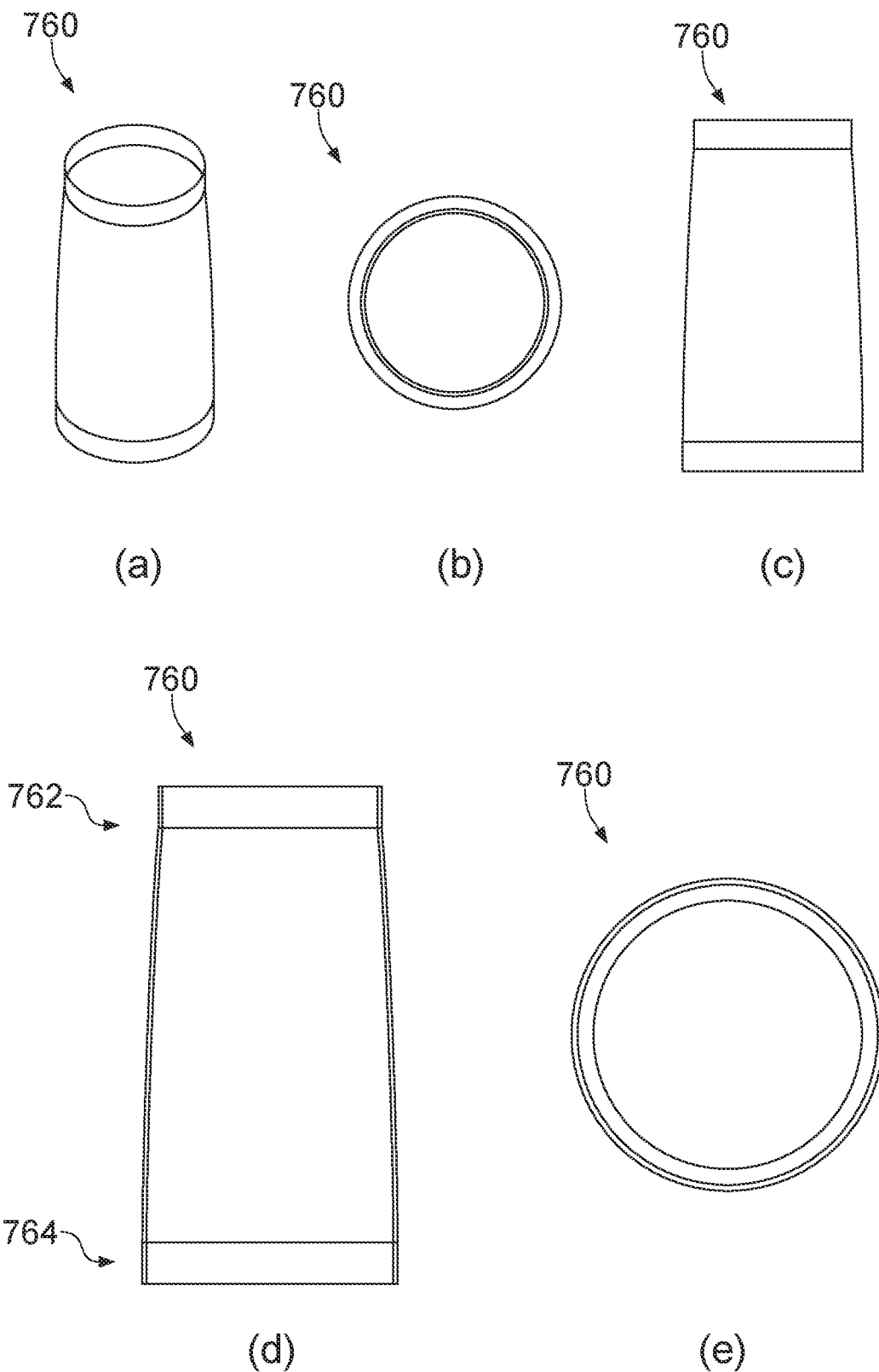
FIG. 26 illustrates (a) a perspective view, (b) a top view, (c) a side view, (d) a cross-sectional view, and (e) a bottom view of a gaiter of the connector of FIG. 19.
Figure 27:
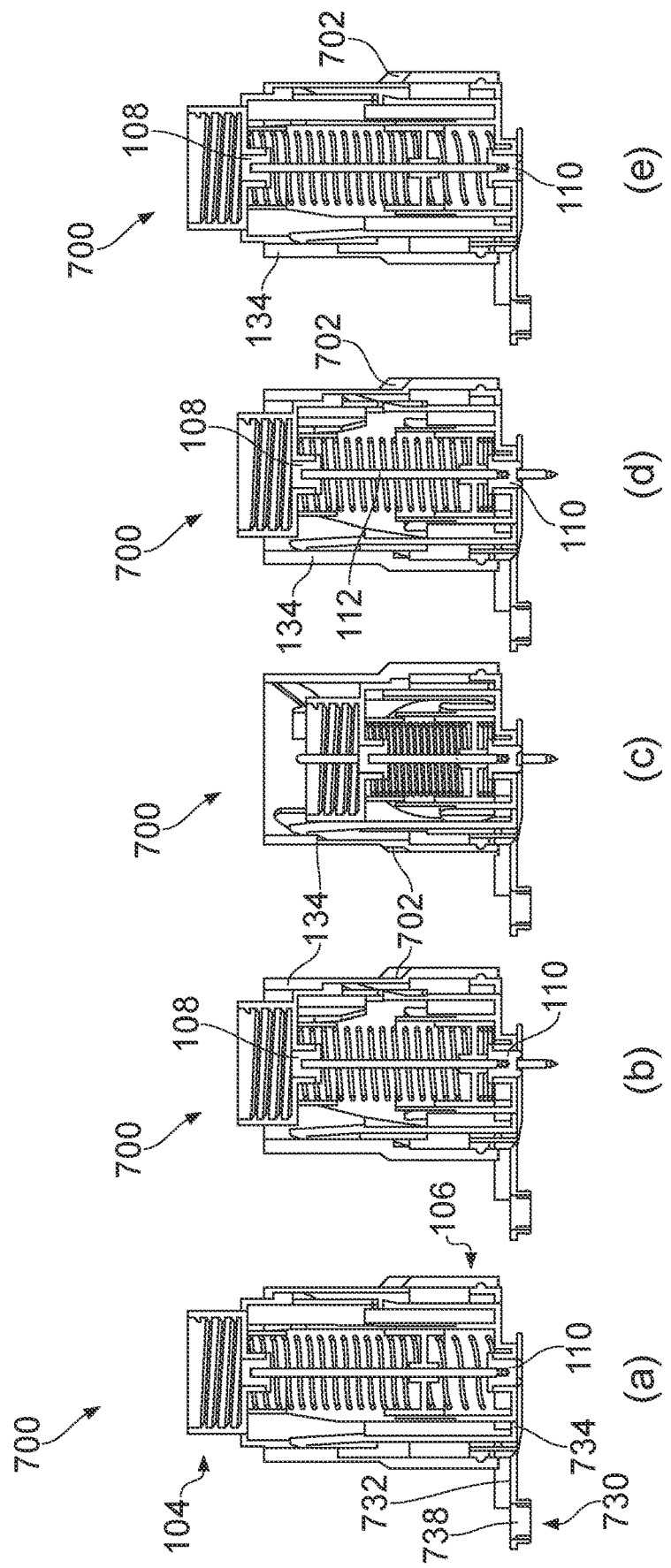
FIG. 27 illustrates the connector of FIG. 19(a) prior to actuation, (b) following aseptic connection to a first fluid volume, (c) following aseptic connection to a second fluid volume, (d) following aseptic disconnection from the second fluid volume, and (e) following aseptic disconnection from the first fluid volume.

The connector 700 includes a lower housing portion 102*b*, as shown best in FIGS. 21(*a*) to 21(*e*), and an upper housing portion 102*a*, as best shown in FIGS. 22(*a*) to 22(*e*), enclosed by the outer sleeve 134, as shown best in FIGS. 23(*a*) to 23(*e*).

Figure 19:
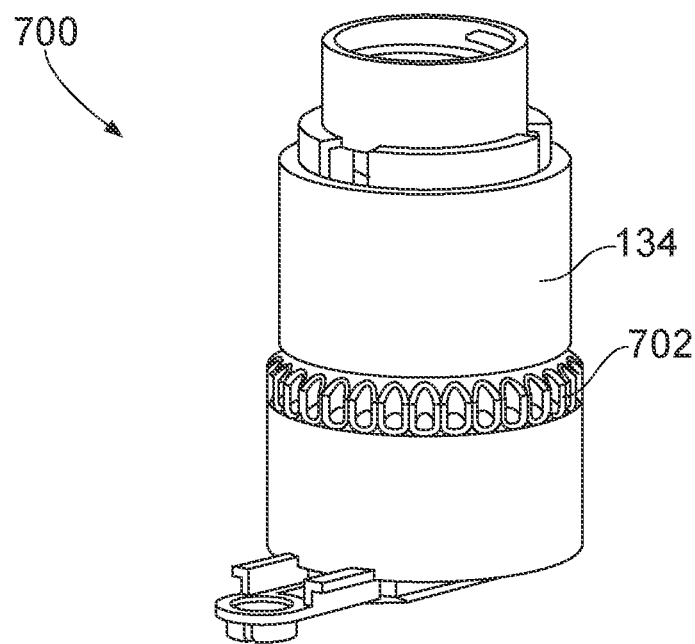
FIG. 19 illustrates a perspective view of a connector according to another embodiment of the present disclosure.

As shown in FIG. 19, the outer sleeve 134 of the connector 700 includes a plurality of teeth 702 formed as recesses within an outer surface of the outer sleeve 134. The plurality of teeth 702 are configured and arranged to engage with a cooperating feature of an automated actuation mechanism formed as part of an instrument (not shown). In this way, the outer sleeve 134 may be actuated, i.e., rotated, automatically by an actuation mechanism of an instrument, an incubator or the like.

Referring to FIGS. 21(*a*) to 21(*e*), and further reference to FIGS. 22(*a*) to 22(*e*), the lower housing portion 102*b* includes an inner body concentrically displaced within an outer body and attached thereto. The inner body and the outer body are generally of equally heights. Further, the lower housing portion 102*b* includes a plurality of arms 704, each arm 704 extending axially from an upper, or distal, portion of the lower housing portion 102*b*. Further, each arm 704 is provided with a hook portion 706 at a distal end thereof. The arms 704 may be resiliently deformable, or otherwise flexible. The lower housing portion 102*b* is also provided with a plurality of outwardly inclined tongues 708, inclining outwardly with respect to the central longitudinal axis and optionally formed within cut-out portions of the outer body of the lower housing portion 102*b*. The tongues 708 may be resiliently deformable, or otherwise flexible. The tongues 708 are arranged to engage, at their distal ends, with a bottom edge of the upper housing portion 102*a* so as to prevent the upper housing portion 102*a* being disposed over the lower housing portion 102*b*. In this way, the tongues 708 are formed as needle-safe features so as to only allow the upper housing portion 102*a* to be disposed over the lower housing portion 102*b* when required and intended. Thus, accidental axial translation of the upper housing portion 102*a* with respect to the lower housing portion 102*b* is mitigated. In particular, in use, the upper housing portion 102*a* is placed over the lower housing portion 102*b*. The bottom edge of the upper housing portion 102a engages with the tongues 708. The tongues 708 must be pushed inwardly, by an actuation mechanism or by a user, so as to allow the upper housing portion 102a to be disposed over the lower housing portion 102b. In some examples, the tongues 708 may be pushed inwardly by one or more pins of an actuation mechanism (not shown). On the contrary, when removing the upper housing portion 102a from the lower housing portion 102b, the upper housing portion 102a is axially removed and the tongues 708 assume their original position by virtue of their resiliently deformable nature.

The lower housing portion 102b also includes a circumferential skirt 710 having a plurality of slots 712 thereby defining a plurality of resiliently deformable portions 714 of the circumferential skirt 710. Each resiliently deformable portion 714 includes an outwardly, or radially, extending ledge 716 configured and arranged to engage with the circumferential groove 138 of the outer sleeve 134 of the connector 700 (see FIG. 20), in use, thereby forming a snap-fit arrangement. The circumferential skirt 710 may be interrupted by an opening configured and arranged to receive an aseptic seal system as described further below.

Referring to FIGS. 22(a) to 22(e), the upper housing portion 102a includes a plurality of windows 720 configured and arranged to receive the arms 704 therethrough, and the hook portions 706 thereof (see FIGS. 21(a) to 21(e)), in use. The hook portions 706 (see FIGS. 21(a) to 21(e)) are configured and arranged to retain the lower housing portion 102b to the upper housing portion 102a and prevent accidental release thereof. Thus, needle-stick injuries and malfunctioning of the connector may be prevented. In other words, the arms 704 extending through the windows 720 must be compressed to release the upper housing portion 102a from the lower housing portion 102b. Thus, a quick and needle-safe assembly and disassembly of the connector may be achieved.

Further, the upper housing portion 102a also includes a plurality of protrusions, formed as circular studs, 722, extending radially outwardly from the body of the upper housing portion 102a, configured and arranged to cooperate with the rail 136 of the outer sleeve 134, in the same manner as described in the above embodiment of FIGS. 1 to 11. There is also provided a slot 724 formed in the body of the upper housing portion 102a extending axially downwardly from each of the studs 722 toward the bottom edge of the upper housing portion 102a. The slots 724 are configured and arranged to allow for one or more pins, or like features, of an actuation mechanism (not shown) to protrude therethrough, to engage the needle-safe features, i.e., tongues, 708 of FIGS. 21(a) to 21(e) as described above, and/or to protrude therethrough following actuation. As such, when assembled, the slots 724 are aligned with the tongues 708 of FIGS. 21(a) to 21(e) and allow a space for one or more pins of an actuating mechanism (not shown) to protrude.

Referring to FIGS. 19, 20 and 24(a) to 24(e), the connector 700 is provided with an aseptic seal system 730 that is configured and arranged to mate with a corresponding aseptic seal system (not shown) on another component, such as a receptacle, an interface or the like. The aseptic seal system 730 is provided with a clip portion 732, preferably composed of high density polyethylene (HDPE), configured and arranged to clip to the outer sleeve 134 of the connector 700 in use, and an aseptic membrane 734. The clip portion 732 is provided with a pair of substantially parallel lateral rails 735 having an upstanding wall 736 at one end thereof and an aperture 738 at another end thereof.

Figure 20:
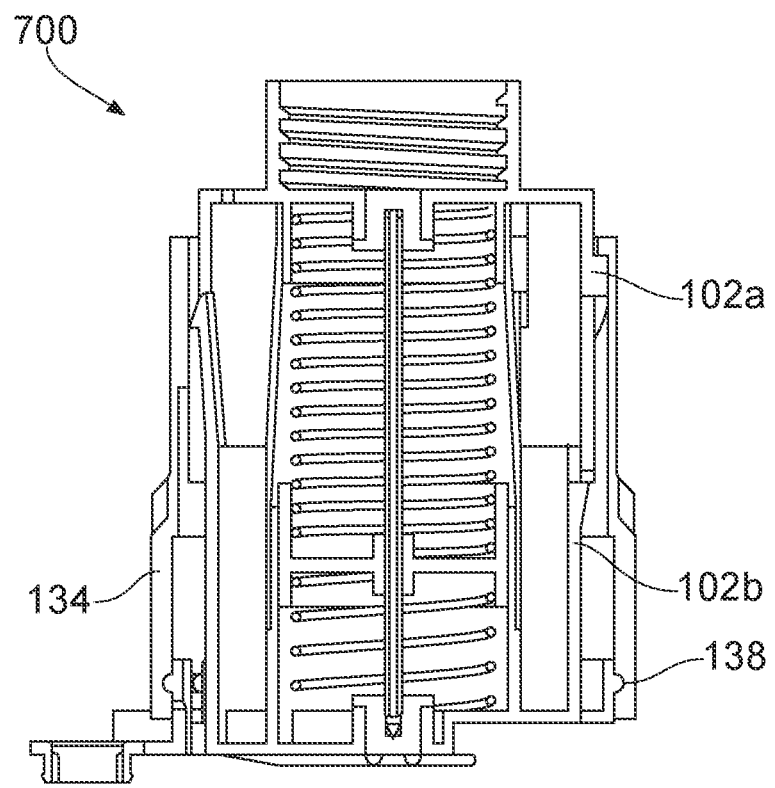
FIG. 20 illustrates a cross-sectional view of the connector of FIG. 19.

The upstanding wall 736 is provided with a protrusion 740 extending radially outwardly. With particular reference to FIGS. 19 and 20, the rails 735 are configured and arranged to be slidably received within a corresponding portion of the outer sleeve 134 and detachably coupled to a circumferential groove 138 thereof by protrusion 740. The aseptic seal system 730 is also arranged to be received within a space of the lower housing portion 102b, as described above. Thus, once received within the lower housing portion 102b, in use, the protrusion 740 and the upstanding wall 736 complete the circumferential skirt 710 of the lower housing portion 102b (see FIGS. 21(a) to 21(e)). In use, upon removal of the aseptic seal system 730 from the connector 700, the upstanding wall 736 may be caused to break, i.e., the upstanding wall 736 may be frangible. Thus, the one-time use nature of the aseptic seal system 730 is aided. Alternatively, the upstanding wall 736 may be uncoupled from the outer sleeve 134 prior to removal.

The aperture 738 is configured and arranged to receive a corresponding protrusion formed as part of an actuation system (not shown) so as to couple thereto. Upon actuation, the protrusion engages the aperture 738 so as to slidably remove the clip portion 732, and the associated aseptic membrane 734.

The aseptic membrane 734 may be formed as an aseptic paper seal, a polyethylene film, or the like, and is generally coupled to the clip portion 732. The aseptic membrane 734 includes at least one fold 742. The at least one fold 742 forms an aseptic surface 744 and a mating surface 746. The aseptic surface 744 is arranged to aseptically seal, i.e., cover, the second septum seal 110 in use (see FIG. 2). The mating surface 746 is arranged to cooperate and mate with a corresponding mating surface (not shown) of a corresponding aseptic seal system (not shown). The mating surface 746 may be heat welded, adhered, or the like to a corresponding mating surface.

Referring to FIGS. 25(a) to 25(e), the collar 118 of the connector 700 is shown in more detail. The collar 118 is formed so as to engage, via a friction-fit, with the hollow needle 112. As can be seen in FIGS. 20 and 25(d), the collar 118 is positioned off-center toward the second end 116 of the hollow needle 112, or away from the first end 114 of the hollow needle 112.

Referring to FIGS. 20 and 26(a) to 26(e), the connector 700 further includes a flexible gaiter 760 formed generally as a cylindrical sleeve. The flexible gaiter 760 is coupled at a distal end 762 to the upper housing portion 102a, and is coupled at a proximal end 764 to the lower housing portion 102b. The gaiter 760 is flexible so as to account for axial displacement between the upper and lower housing portions 102a, 102b, in use. The gaiter 760 can be coupled at its distal end 762 and proximal end 764 by any appropriate means, such as by welding, an adhesive, a clip, or the like.

With reference to FIGS. 19 to 26, and particular reference to FIGS. 27(a) to 27(e), the connector 700 is shown, in use. In FIG. 27(a), the connector 700 is coupled to respective volumes of fluids (not shown) at its distal end 104 and proximal end 106. The aseptic membrane 734 of the aseptic seal system 730 is coupled to a corresponding aseptic membrane on one of the volumes of fluids (not shown), adjacent the proximal end 106. The aseptic seal system 730, coupled to a corresponding aseptic seal system (not shown) is then removed by an actuation device, preferably through slidably removing, i.e., pulling, the clip portion 732 of the aseptic seal system 730. In some examples, an actuation device may include a protrusion that is received within the aperture 738 of the clip portion 732. The action of slidably removing the aseptic membranes 734 enables aseptic face-to-face engagement of the second septum seal 110 of the connector 700 with a corresponding septum seal of a volume of fluid. In some examples, such as the example shown, the aseptic seal system 730 remains in place and the hollow needle 112 is arranged to pierce through the aseptic membrane 734.

As shown in FIG. 27(b), the connector 700 is actuated, preferably through a toothed actuation mechanism engaging with the plurality of teeth 702 on the outer sleeve 134 of the connector 700, so as to rotate the outer sleeve 134. As shown in FIGS. 27(b) and 27(c), continually rotation of the outer sleeve 134 provides sequential piercing of the first and second septum seals 108, 110, as described above, to provide an aseptic fluid pathway between the two volumes of fluid. Then, as shown in FIGS. 27(d) and 27(e), the actuation mechanism counter-rotates the outer sleeve 134, via the teeth 702, so as to aseptically disconnect the volumes of fluid by sequentially aseptically disconnecting the hollow needle 112 from the first and second septum seals 108, 110. The connector 700 may then be removed and discarded.

Figure 28:
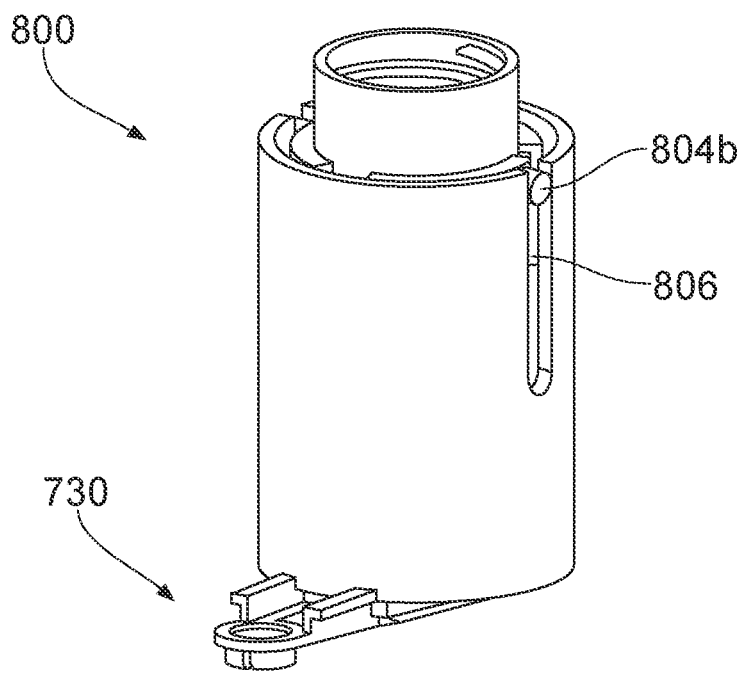
FIG. 28 illustrates a perspective view of a connector according to another embodiment of the present disclosure.
Figure 29:
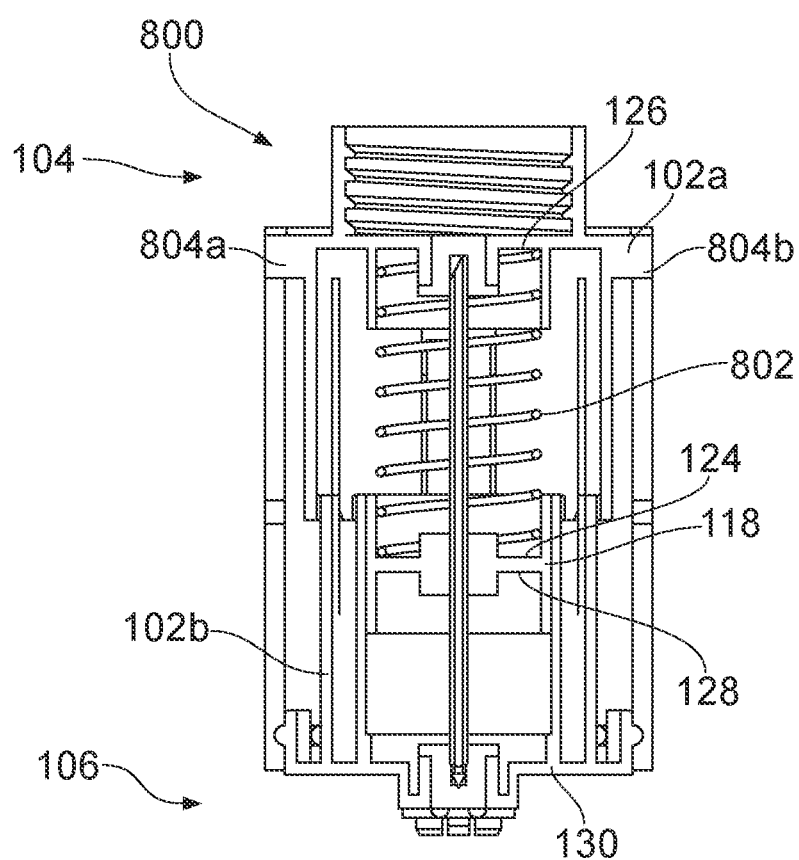
FIG. 29 illustrates a cross-sectional view of the connector of FIG. 28.
Figure 30:
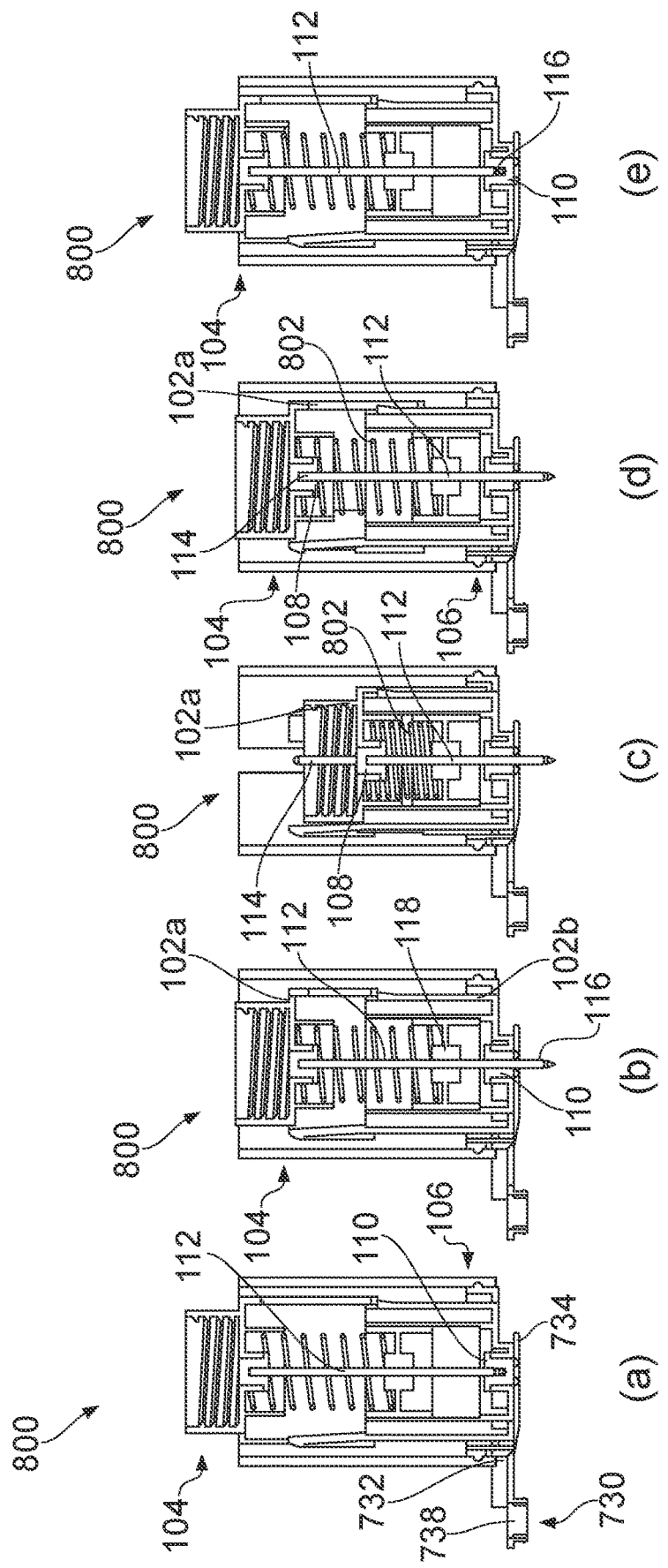
FIG. 30 illustrates the connector of FIG. 28(a) prior to actuation, (b) following aseptic connection to a first fluid volume, (c) following aseptic connection to a second fluid volume, (d) following aseptic disconnection from the second fluid volume, and (e) following aseptic disconnection from the first fluid volume.

As shown in FIGS. 28 to 30, there is provided another embodiment of a connector 800 for connecting two volumes of fluid. The connector 800 is the same construction as connector 100, described in relation FIGS. 1 to 11, except for the details listed below. Like reference numerals denote like features.

As best shown in FIG. 29, the connector 800 includes a single helical spring 802 received between the collar 118 and the upper housing portion 102a. Specifically, the single helical spring 802 extends from the inner surface 126 of the distal end 104 of the housing 102, i.e., the inner surface 126 of the upper housing portion 102a, to the upper surface 124 of the collar 118. In other embodiments, a single helical spring may be received between the collar 118 and the lower housing portion 102b. In those embodiments, the single helical spring 802 would extend from the inner surface 130 of the proximal end 106 of the housing, i.e., the inner surface 130 of the lower housing portion 102b, to the lower surface 128 of the collar 118. In those embodiments, sequential piercing would be achieved in the opposite order to that described below.

With further reference to FIGS. 28 and 29, the upper housing portion 102a of the connector 800 includes a pair of actuatable lugs 804a, 804b. The actuatable lugs 804a, 804b are shown as generally cylindrical protrusions extending radially from the outer surface of the upper housing portion 102a. The actuatable lugs 804a, 804b may be any size or shape. The outer sleeve 134 of the connector 800 includes a pair of longitudinal slots 806, each configured and arranged to receive one of the actuatable lugs 804a, 804b. The actuatable lugs 804a, 804b are movable axially, and also guided by, the longitudinal slots 806 so as to allow axial translation, i.e., collapsing, of the upper housing portion 102a with respect to the lower housing portion 102b as described further below. In other examples, the actuatable lugs may be formed on the lower housing portion 102b to achieve sequential piercing in the opposite order to that described below.

The connector 800 further includes an aseptic seal system 730 as described above in relation to FIGS. 19, 20 and 24(a) to 24(e).

With further and particular reference to FIGS. 30(a) to 30(e), the connector 800 is shown in use. In FIG. 30(a), the connector 800 is coupled to respective volumes of fluids at its distal end 104 and proximal end 106. The aseptic membrane 734 of the aseptic seal system 730 is coupled to a corresponding aseptic membrane on one of the volumes of fluids (not shown), adjacent the proximal end 106. The aseptic seal system 730, coupled to a corresponding aseptic seal system (not shown) is then removed by an actuation device, preferably through slidably removing, i.e., pulling, the clip portion 732 of the aseptic seal system 730. In some examples, an actuation device may include a protrusion that is received within the aperture 738 of the clip portion 732. The action of slidably removing the aseptic membranes 734 enables aseptic face-to-face engagement of the second septum seal 110 of the connector 800 with a corresponding septum seal of a receptacle. In some examples, such as the example shown, the aseptic seal system 730 remains in place and the hollow needle 112 is arranged to pierce through the aseptic membrane 734.

As shown in FIG. 30(b), the connector 800 is actuated, preferably through an axially translatable actuation mechanism engaging with the distal end 104 of the connector 800, so as to axially translate, i.e., push or collapse, the upper housing portion 102a with respect to the lower housing portion 102b. Alternatively, an actuation mechanism may engage with the pair of actuatable lugs 804a, 804b (see FIG. 28) so as to axially translate the upper housing portion 102a. The actuation mechanism may be formed as part of an instrument, such as an incubator. As can be seen in FIG. 30(b), as the upper housing portion 102a collapses with respect to the lower housing portion 102b, the collar 118, and thus the hollow needle 112 operably coupled thereto, is axially translated toward the second septum seal 110 at the proximal end 106 of the connector 800. The spring 802 remains in the original configuration during this initial actuation step due to the biasing force imparted onto the collar 118. Such axial translation thus causes the hollow needle 112 to pierce the second septum seal 110 at its second end 116.

As shown in FIG. 30(c), continual axial translation of the upper housing portion 102a causes compression of the spring 802 so as to allow the upper housing portion 102a to collapse further and thus cause the hollow needle 112 to pierce the first septum seal 108 at its first end 114. Thus, the volumes of fluid connected at each end of the connector 800 are fluidly connected by the hollow needle 112.

As shown in FIG. 30(d), the upper housing portion 102a is allowed to relax, through the biasing force of the spring 802, or the upper housing portion 102a is axially translated toward the distal end 104 of the connector 800, i.e., away from the proximal end 106 of the connector 800. In this way, the hollow needle 112 ceases to pierce the first septum seal 108 at its first end 114. Further axial translation of the upper housing portion 102a toward the distal end 104 of the connector 800, shown in FIG. 30(e), causes the hollow needle 112 to cease the piercing of the second septum seal 110 at its second end 116. Thus, an aseptic disconnection is achieved. The connector 800 may be removed and discarded.

As shown in FIGS. 31 to 35, there is provided another embodiment of a connector 900 for connecting two volumes of fluid. The connector 900 is the same construction as connector 100, described in relation FIGS. 1 to 11, except for the details listed below. Like reference numerals denote like features.

Figure 31:
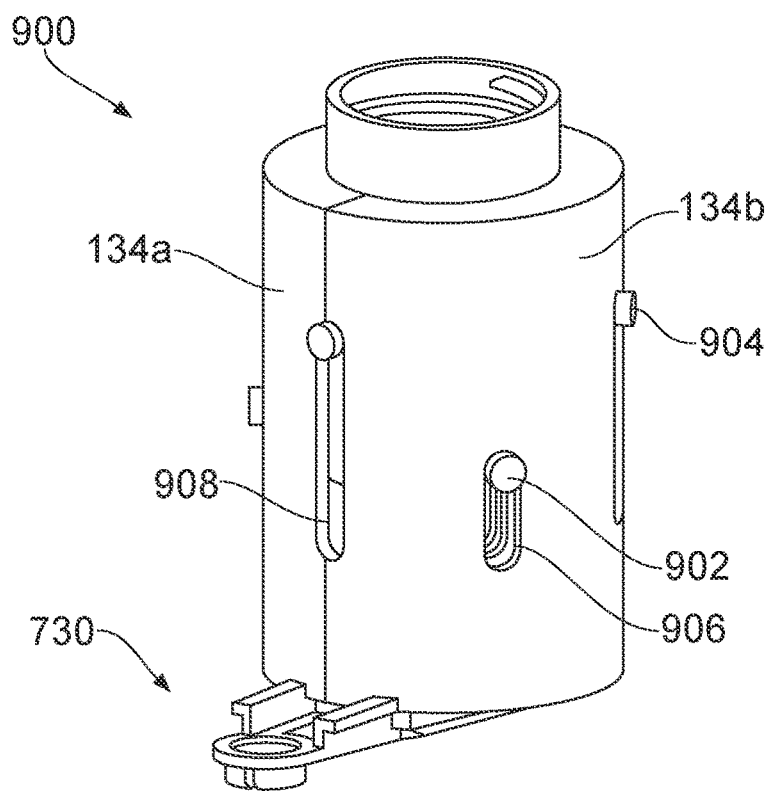
FIG. 31 illustrates a perspective view of a connector according to another embodiment of the present disclosure.
Figure 32:
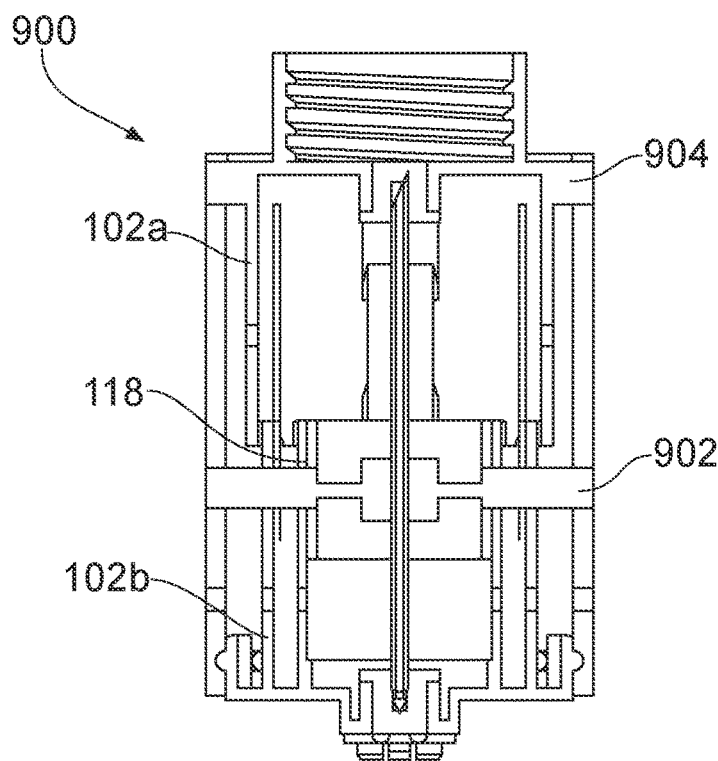
FIG. 32 illustrates a cross-sectional view of the connector of FIG. 31.
Figure 33:
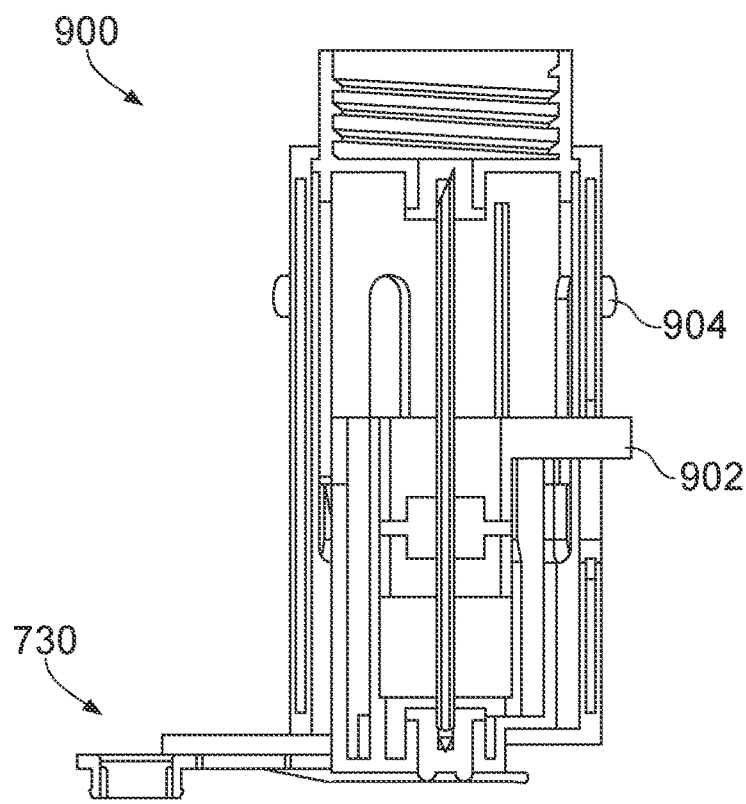
FIG. 33 illustrates another cross-sectional view of the connector of FIG. 31.

As shown in FIGS. 31 to 33, the connector 900 of the present embodiment does not include a spring, unlike the previous embodiments. Instead, the connector 900 is provided with a collar 118 including a plurality of actuatable lugs 902 extending radially outwardly from the collar 118. The actuatable lugs 902 may be any size or shape. Furthermore, the upper housing portion 102a includes a plurality of actuatable lugs 904 extending radially outwardly from the upper housing portion 102a. Likewise, the actuatable lugs may be any size of shape.

The outer sleeve 134 of the connector 900 comprises two half-pipe portions 134a, 134b, which may be welded, adhered, clipped or the like to secure the same in use. Alternatively, the outer sleeve 134 may be integrally formed. The outer sleeve 134 generally includes a first plurality of longitudinal slots 906 and a second plurality of longitudinal slots 908. As shown in FIG. 31, each of the plurality of actuatable lugs 902 of the collar 118 extend radially outwardly through each of the first plurality of longitudinal slots 906, and each of the plurality of actuatable lugs 904 of the upper housing portion 102a extend radially outwardly through each of the second plurality of longitudinal slots 908. Referring further to FIG. 31, a lower stop of the first plurality of longitudinal slots 906 and a lower stop of the second plurality of longitudinal slots 908 are coplanar, that is, they are formed at a substantially similar or same distance with respect to the proximal end 106 of the connector 900. An upper stop of the first plurality of longitudinal slots 906 and an upper stop of the second plurality of longitudinal slots 908 are non-coplanar, that is, they are formed at a substantially different distance with respect to the proximal end 106 of the connector 900.

Figure 34:
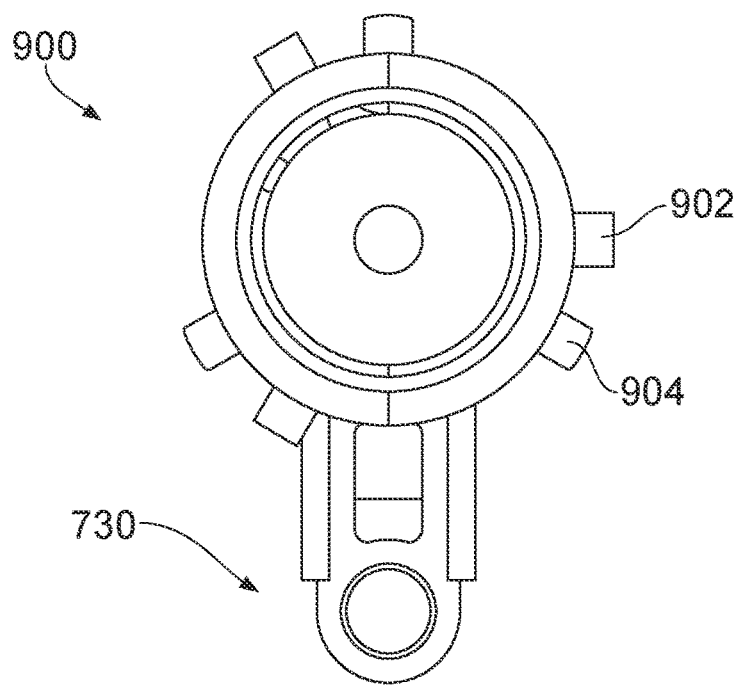
FIG. 34 illustrates a top view of the connector of FIG. 31.
Figure 35:
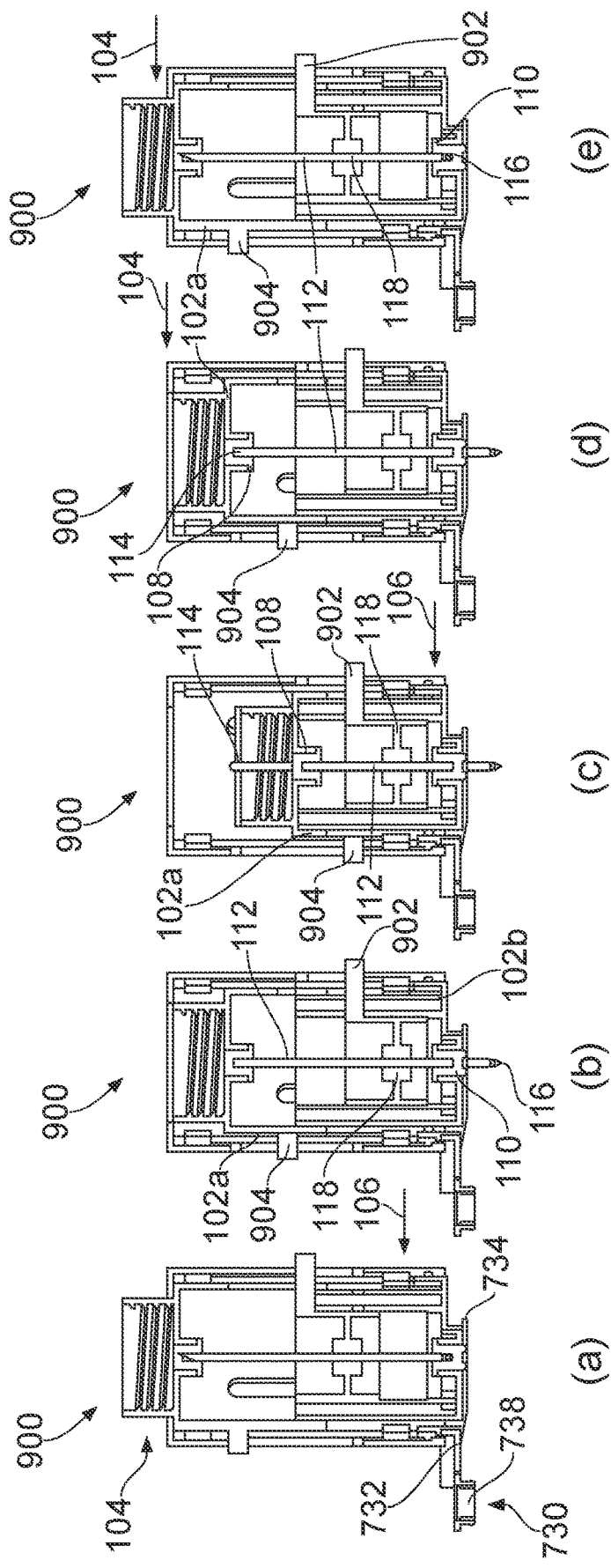
FIG. 35 illustrates the connector of FIG. 31(a) prior to actuation, (b) following aseptic connection to a first fluid volume, (c) following aseptic connection to a second fluid volume, (d) following aseptic disconnection from the second fluid volume, and (e) following aseptic disconnection from the first fluid volume.

As best shown in FIG. 34, the plurality of actuatable lugs 902 extending from the collar 118 are each offset by approximately 120°. Similarly, the plurality of actuatable lugs 904 extending from the upper housing portion 102a are each offset by approximately 120°. The slots of the first plurality of longitudinal slots 906, and the slots of the second plurality of longitudinal slots 908, are similarly offset with respect to the others within the plurality of slots by 120°. Generally, as shown in FIG. 34, the actuatable lugs 902 of the collar 118 and the actuatable lugs 904 of the upper housing portion 102a are offset with respect to one another. Similarly, the first and second plurality of longitudinal slots 906, 908 is offset with respect to one another.

Referring to FIGS. 31 to 34, the connector 900 is further provided with an aseptic seal system 730 as described above in relation to FIGS. 19, 20 and 24(a) to 24(e). However, as best shown in FIG. 33, the aseptic seal system 730 does not include a protruding portion for clipping to the outer sleeve of the connector 900. Thus, the aseptic seal system 730 is freely slidable with respect to the outer sleeve.

The connector 900 is shown, in use, in FIGS. 35(a) to 35(e). In FIG. 35(a), the connector 900 is coupled to respective volumes of fluids at its distal end 104 and proximal end 106. The aseptic membrane 734 of the aseptic seal system 730 is coupled to a corresponding aseptic membrane on one of the volumes of fluids, adjacent the proximal end 106. The aseptic seal system 730, coupled to a corresponding aseptic seal system (not shown) is then removed by an actuation device, preferably through slidably removing, i.e., pulling, the clip portion 732 of the aseptic seal system 730. In some examples, an actuation device may include a protrusion that is received within the aperture 738 of the clip portion 732. The action of slidably removing the aseptic membranes 734 enables aseptic face-to-face engagement of the second septum seal 110 of the connector 900 with a corresponding septum seal of a volume of fluid. In some examples, such as the example shown, the aseptic seal system 730 remains in place and the hollow needle 112 is arranged to pierce through the aseptic membrane 734.

As shown in FIG. 35(b), the connector 900 is actuated, preferably through an axially translatable actuation mechanism engaging with the actuatable lugs 904 extending from the upper housing portion 102a of the connector 900, so as to axially translate, i.e., push or collapse, the upper housing portion 102a with respect to the lower housing portion 102b. Concurrently, an axially translatable actuation mechanism engages with the actuatable lugs 902 extending from the collar 118 of the connector 900 so as to axially translate, i.e., push, the collar 118, and thus the hollow needle 112, toward the second septum seal 110. Thus, the second end 116 of the hollow needle 112 is caused to pierce the second septum seal 110. The actuation mechanism may be formed as part of an instrument, such as an incubator.

As shown in FIG. 35(c), the axially translatable actuation mechanism, engaged with the actuatable lugs 904 extending from the upper housing portion 102a, continues to axial translate the upper housing portion 102a toward the proximal end 106 of the connector 900. Concurrently, the axially translatable actuation mechanism, engaged with the actuatable lugs 902 of the collar 118, retains the collar 118 in place during further actuation of the upper housing portion 102a. In this way, the first septum seal 108 is caused to be pierced by the first end 114 of the hollow needle 112, as shown in FIG. 35(c). In this way, an aseptic fluid pathway is formed between the connected volumes of fluids.

As shown in FIG. 35(d), to aseptically disconnect the connector 900, the upper housing portion 102a is axially translated toward the distal end 104 of the connector 900, through the axially translatable actuation mechanism engaged with the actuatable lugs 904 of the upper housing portion 102a. In this way, the hollow needle 112 is caused to cease piercing of the first septum seal 108 at its first end 114.

As shown in FIG. 35(e), further axially translation of the upper housing portion 102a of the connector 900, through the actuating mechanism engaged with the actuatable lugs 904 of the upper housing portion 102a, is provided. Concurrently, the collar 118, and thus the hollow needle 112, is axially translated toward the distal end 104 of the connector 900, via the actuation mechanism engaging the actuatable lugs 902 of the collar 118, so as to cause the hollow needle 112 to cease piercing of the second septum seal 110 at its second end 116. Thus, the connector 900 is aseptically fluidly disconnected. The connector 900 may be removed and discarded.

As shown in FIGS. 36 to 50, there is provided another embodiment of a connector 1000 for connecting two volumes of fluid. The connector 1000 is the same construction as connector 900, described in relation FIGS. 31 to 35, except for the details listed below. Like reference numerals denote like features.

Figure 36:
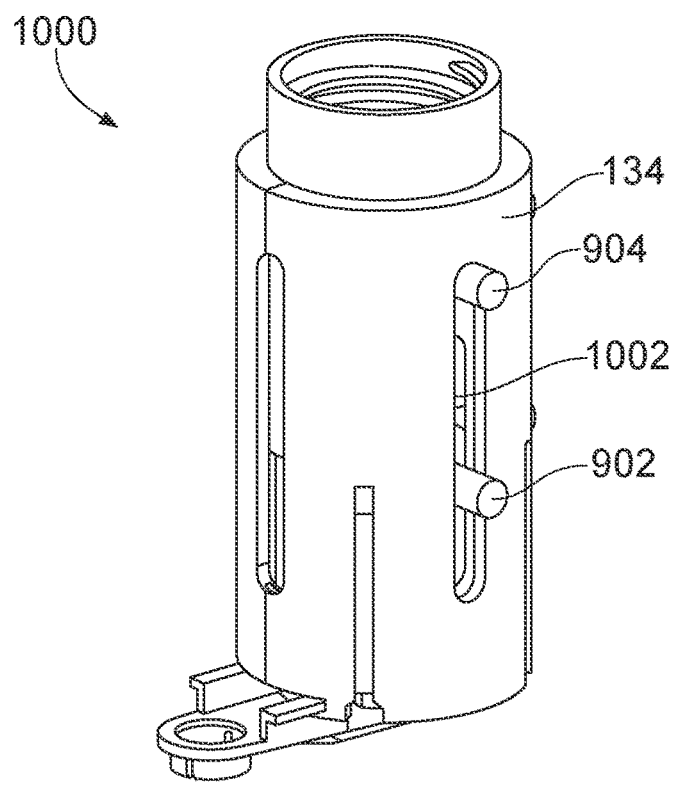
FIG. 36 illustrates a perspective view of a connector according to another embodiment of the present disclosure.
Figure 37:
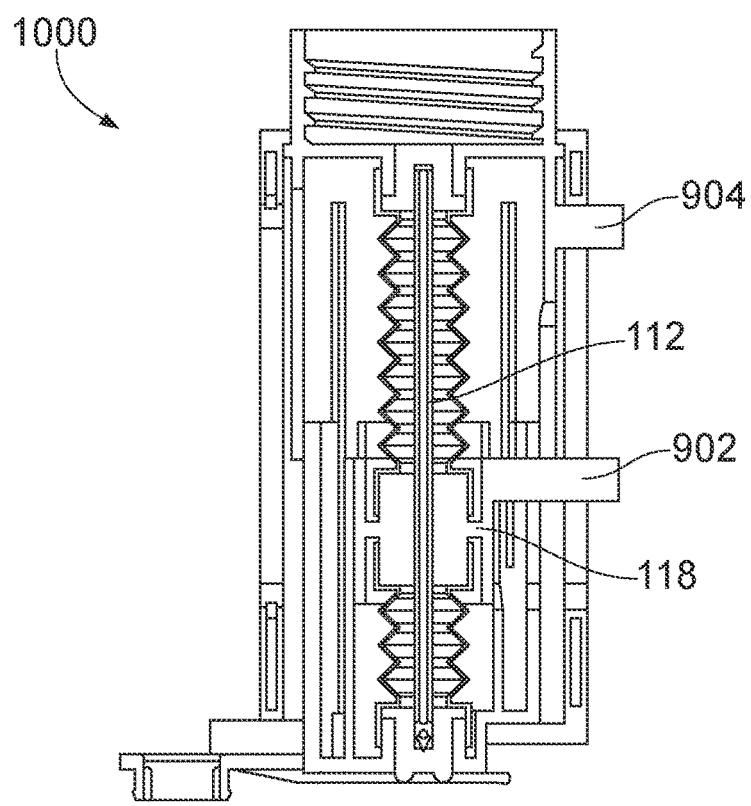
FIG. 37 illustrates a cross-sectional view of the connector of FIG. 36.
Figure 38:
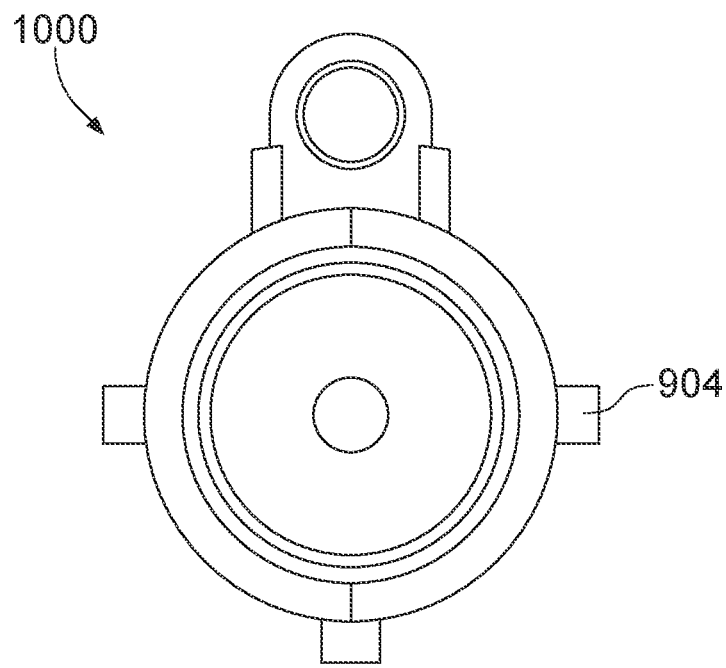
FIG. 38 illustrates a top view of the connector of FIG. 36.
Figure 39:
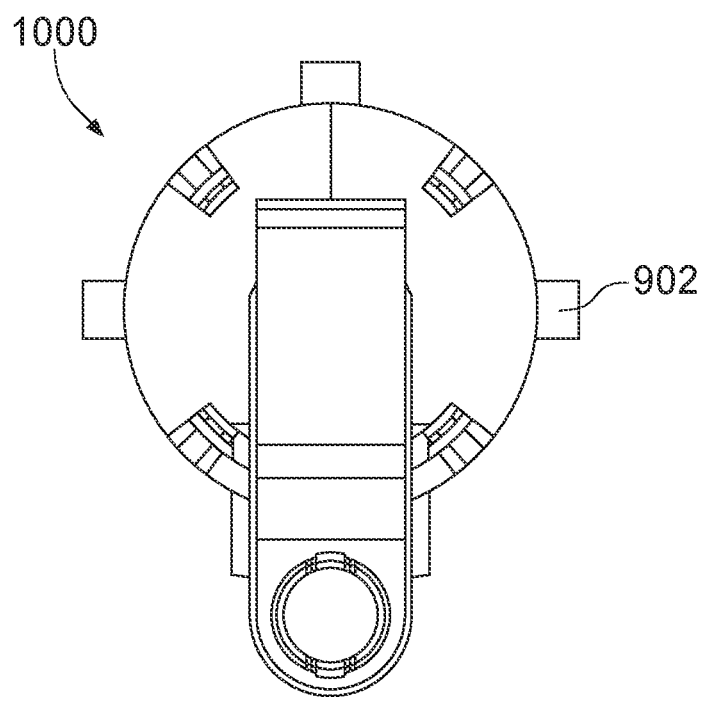
FIG. 39 illustrates a bottom view of the connector of FIG. 36.
Figure 40:
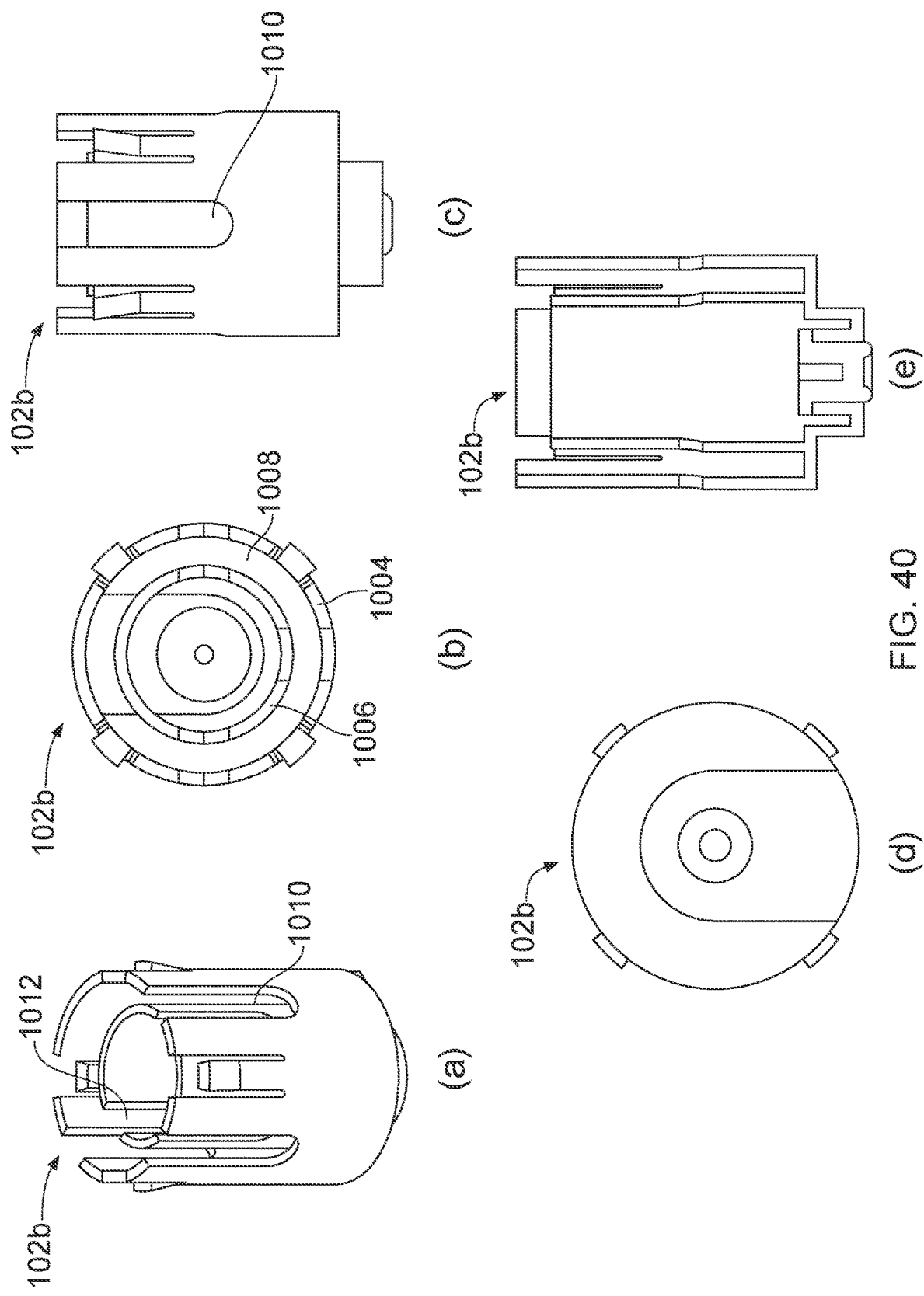
FIG. 40 illustrates (a) a perspective view, (b) a top view, (c) a side view, (d) a bottom view, and (e) a cross-sectional view of the lower housing portion of the connector of FIG. 36.
Figure 41:
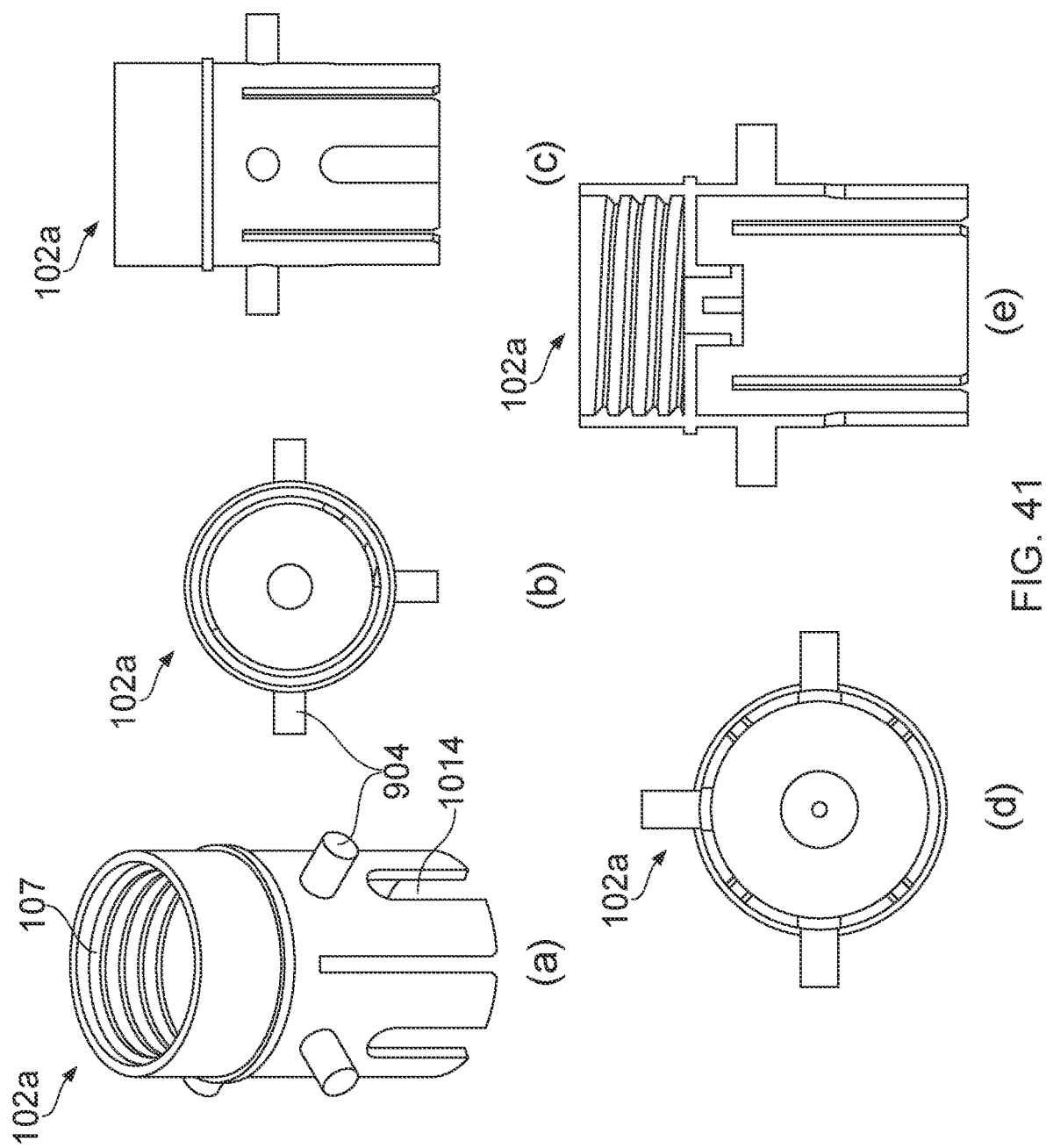
FIG. 41 illustrates (a) a perspective view, (b) a top view, (c) a side view, (d) a bottom view, and (e) a cross-sectional view of the upper housing portion of the connector of FIG. 36.
Figure 42:
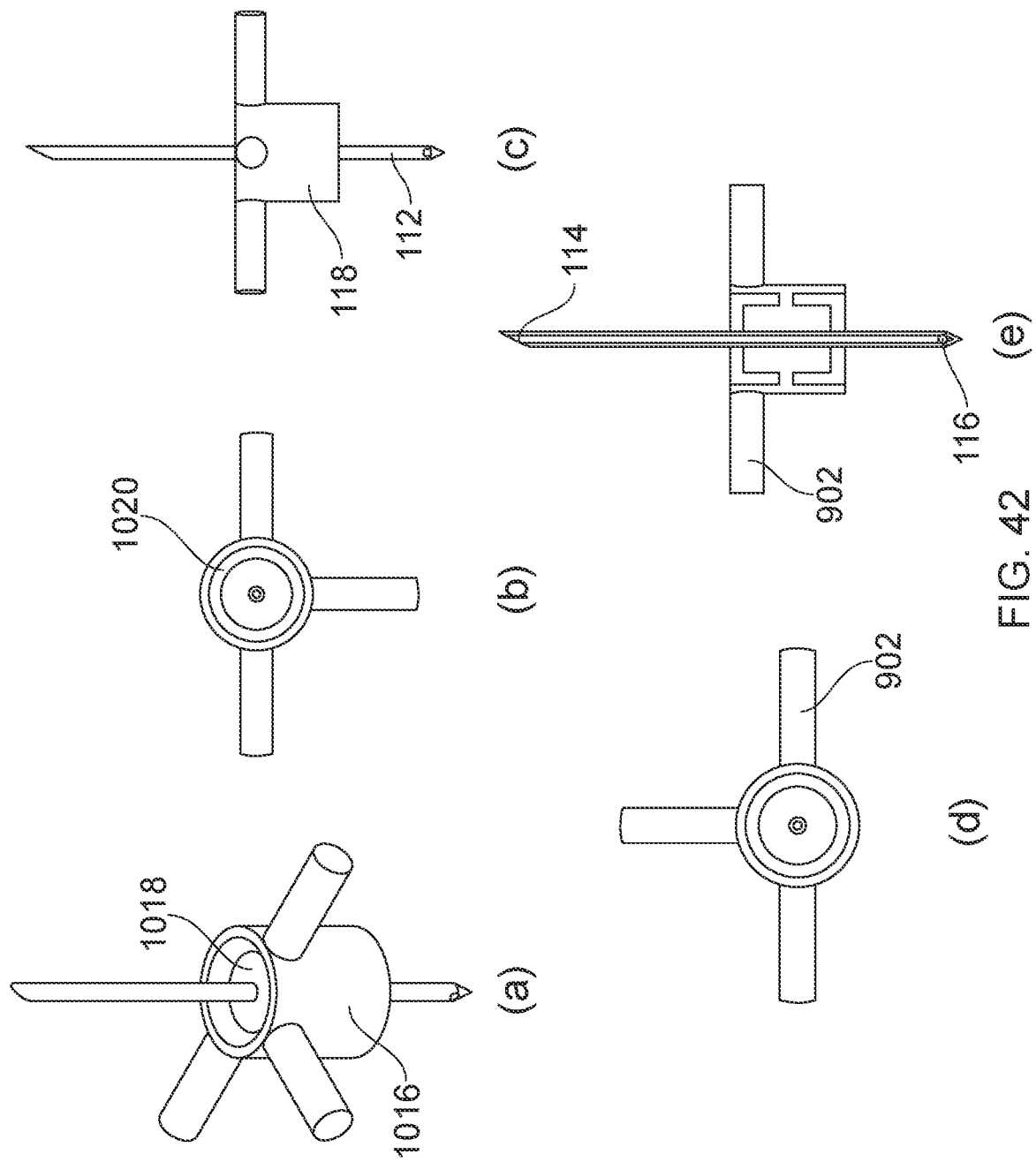
FIG. 42 illustrates (a) a perspective view, (b) a top view, (c) a side view, (d) a bottom view, and (e) a cross-sectional view of the collar and hollow needle of the connector of FIG. 36.
Figure 43:
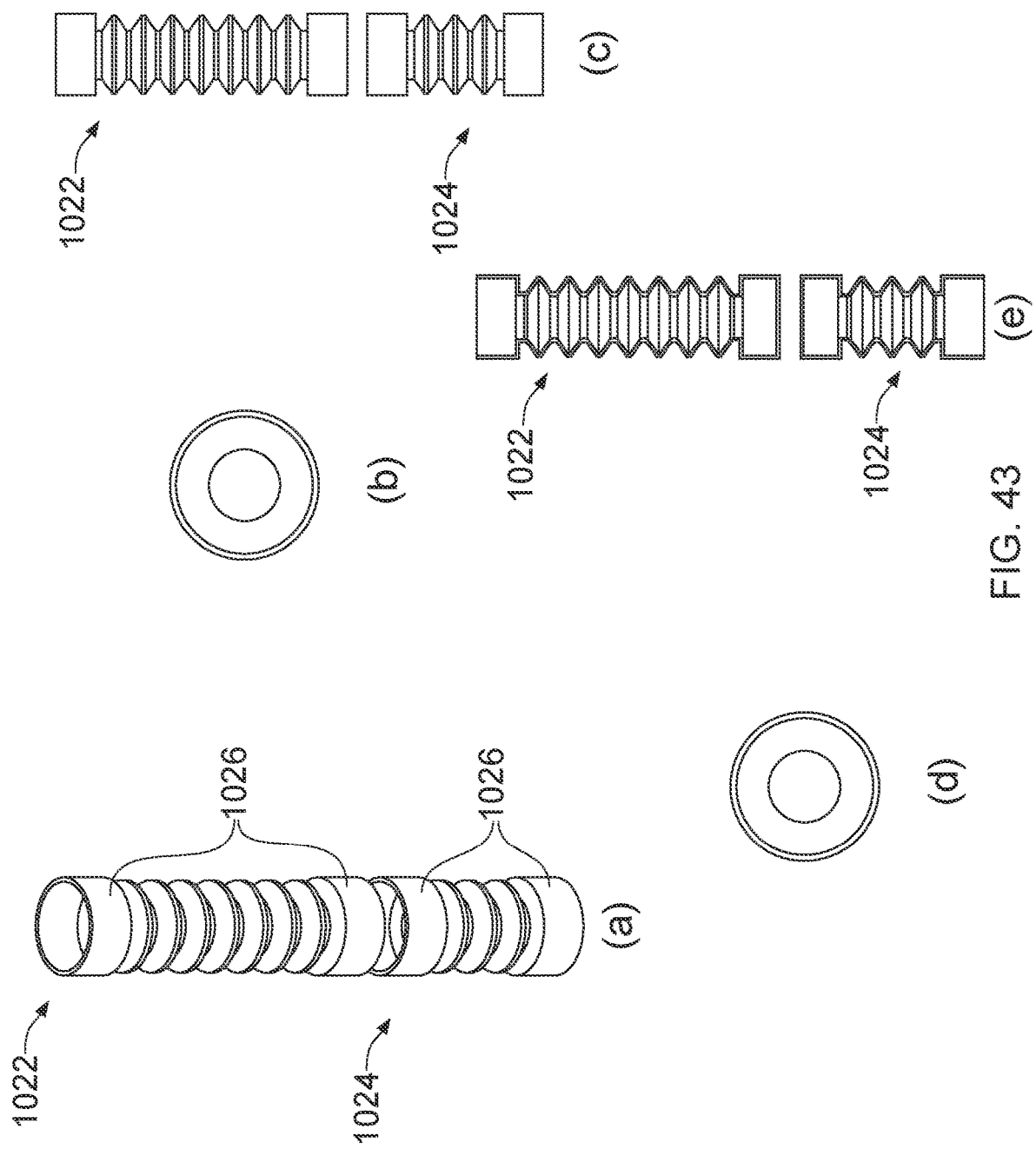
FIG. 43 illustrates (a) a perspective view, (b) a top view, (c) a side view, (d) a bottom view, and (e) a cross-sectional view of the gaiters of the connector of FIG. 36.
Figure 44:
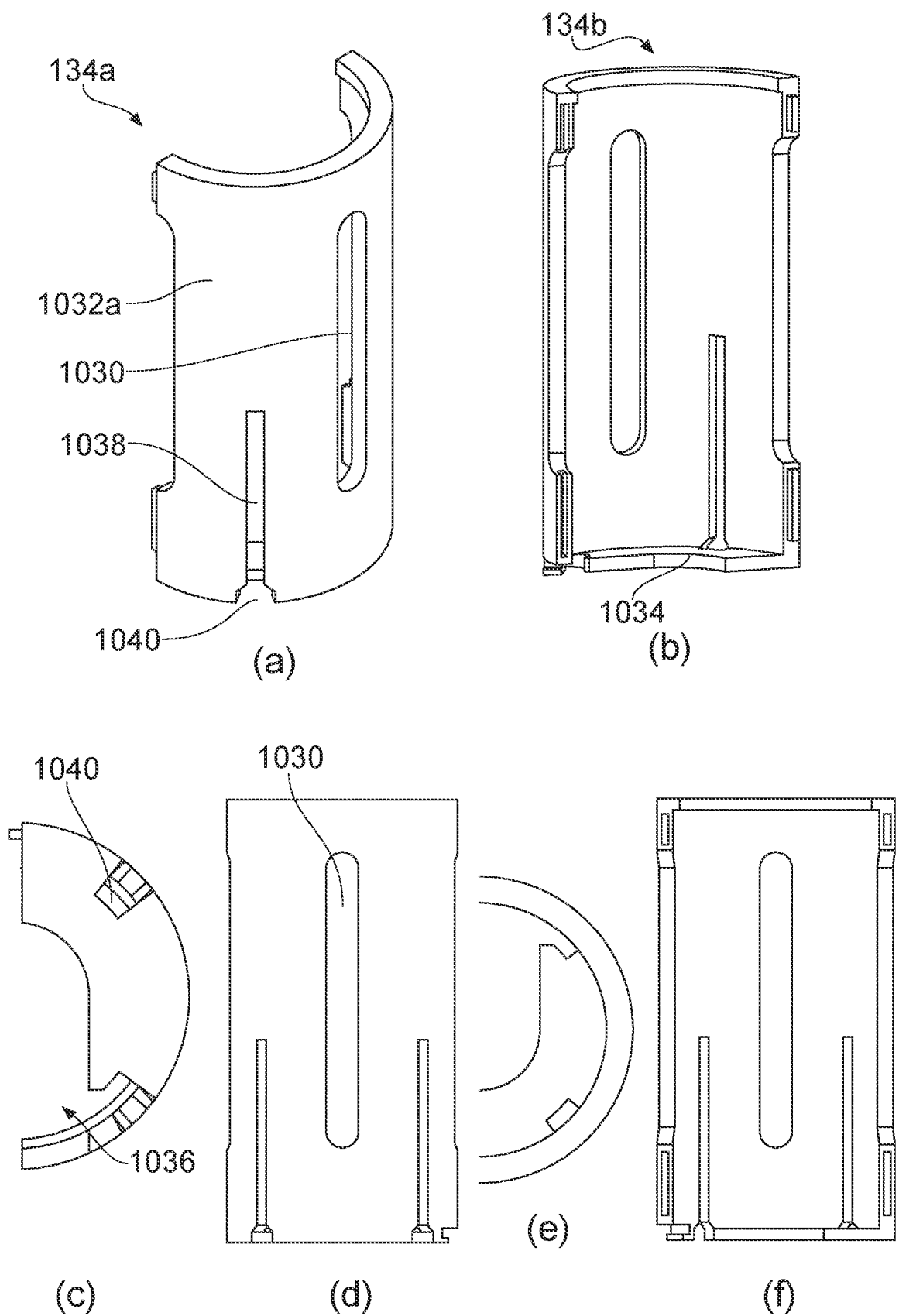
FIG. 44 illustrates (a) a perspective view of one portion of the outer sleeve, (b) a perspective view of another portion of the outer sleeve, (c) a bottom view of a portion of the outer sleeve, (d) a side view of a portion of the outer sleeve, (e) a top view of a portion of the outer sleeve, and (f) another side view of a portion of the outer sleeve of the connector of FIG. 36.
Figure 45:
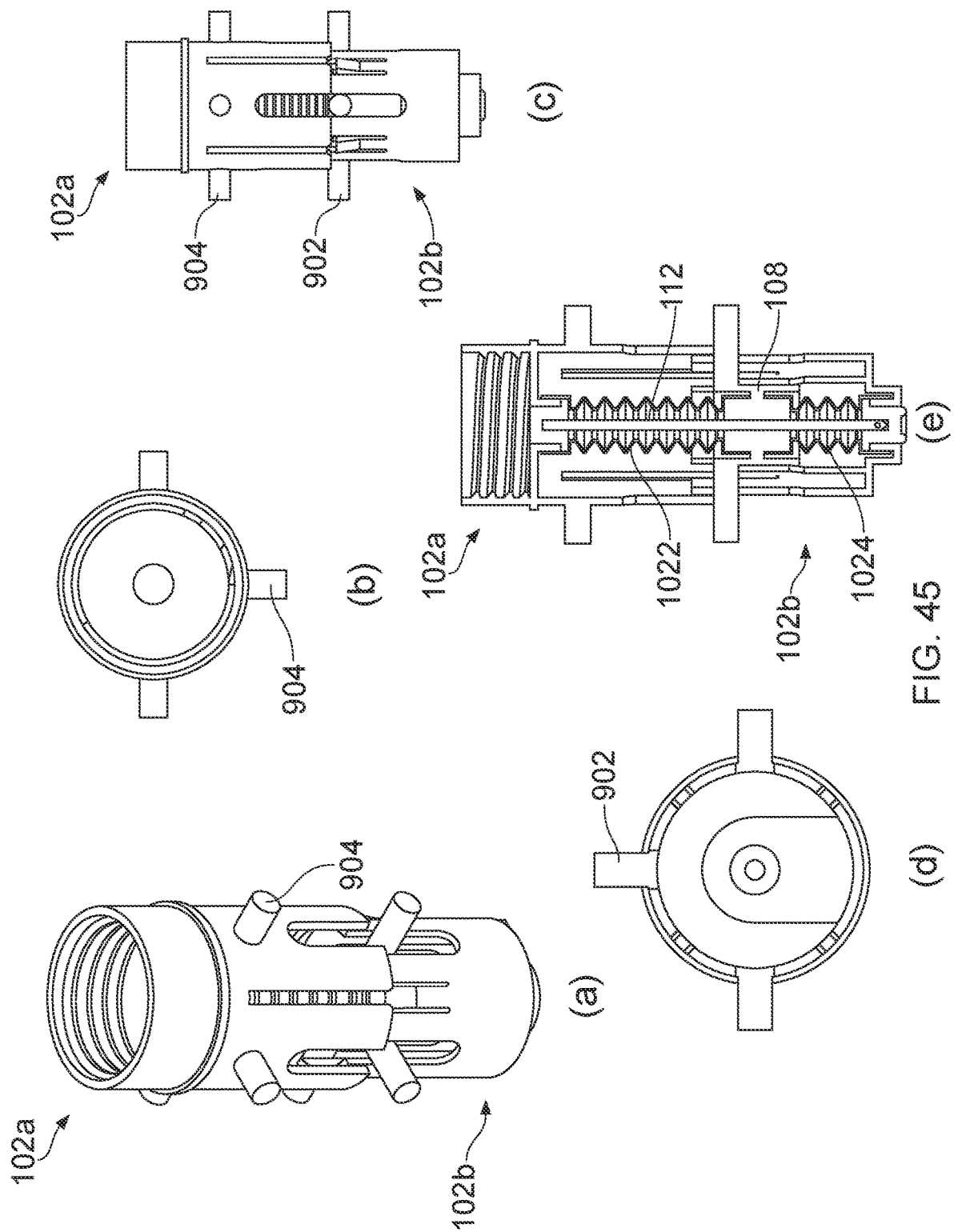
FIG. 45 illustrates (a) a perspective view, (b) a top view, (c) a side view, (d) a bottom view, and (e) a cross-sectional view of the inner components of the connector of FIG. 36.
Figure 47:
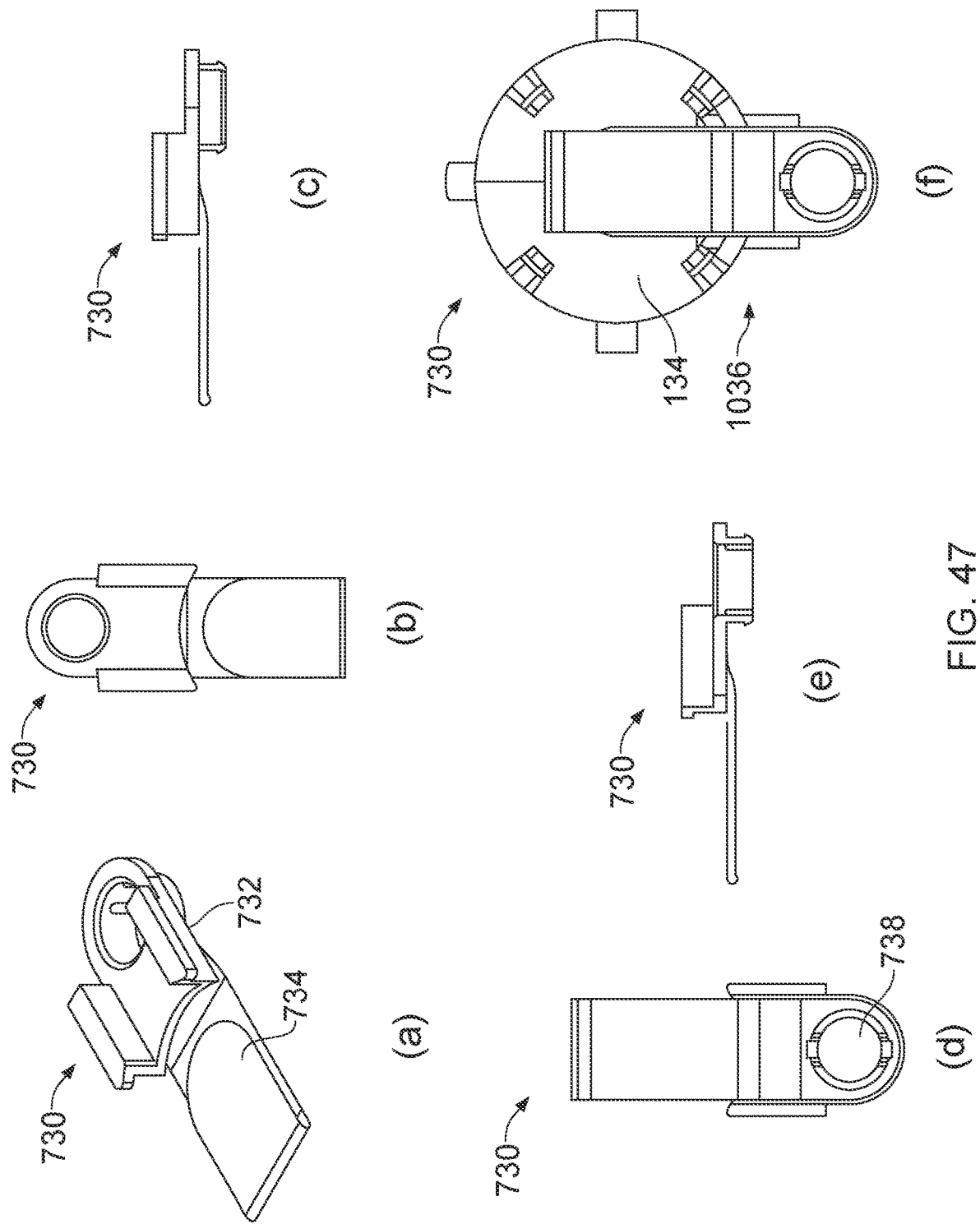
FIG. 47 illustrates (a) a perspective view, (b) a top view, (c) a side view, (d) a bottom view, and (e) a cross-sectional view of an aseptic seal system for use with the connector of FIG. 36, and (f) a bottom view of the aseptic seal system connected to the connector of FIG. 36.
Figure 48:
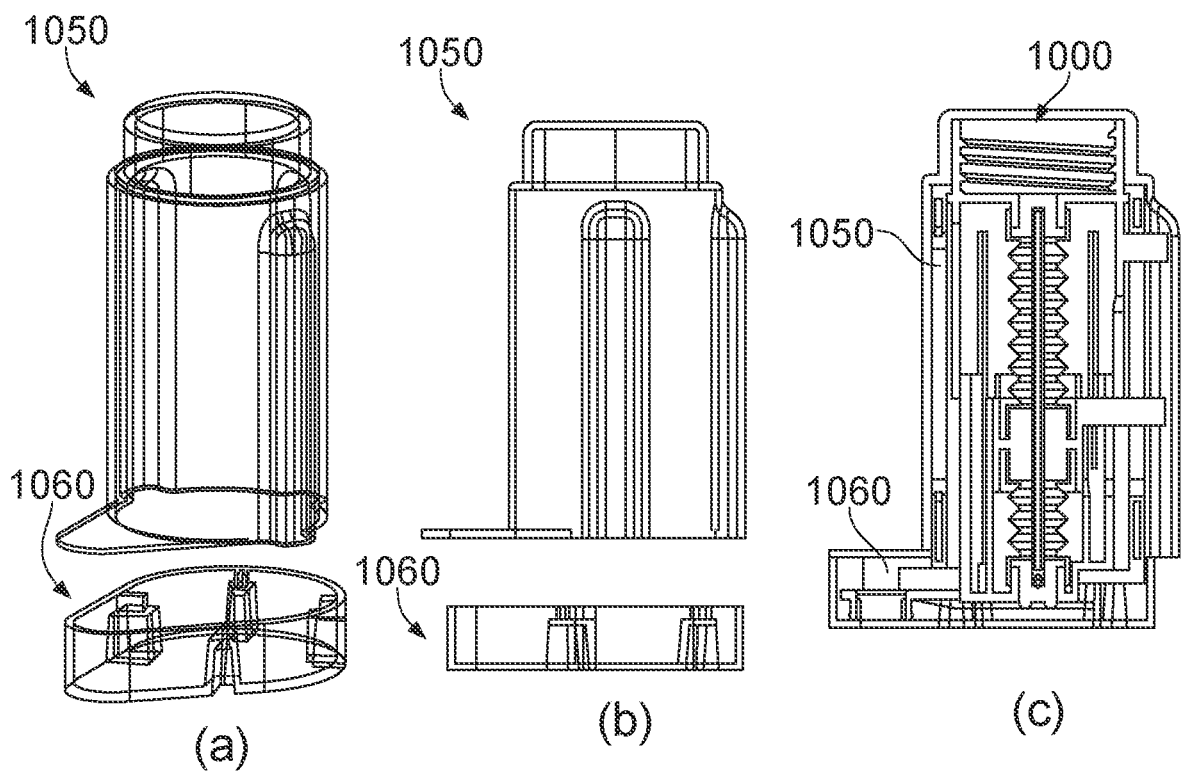
FIG. 48 illustrates (a) a perspective view of a transit cover and a transit cap, (b) a side view of a transit cover and a transit cap, and (c) a cross-sectional view of the connector of FIG. 36 having the transit cover and transit cap attached thereto.
Figure 49:
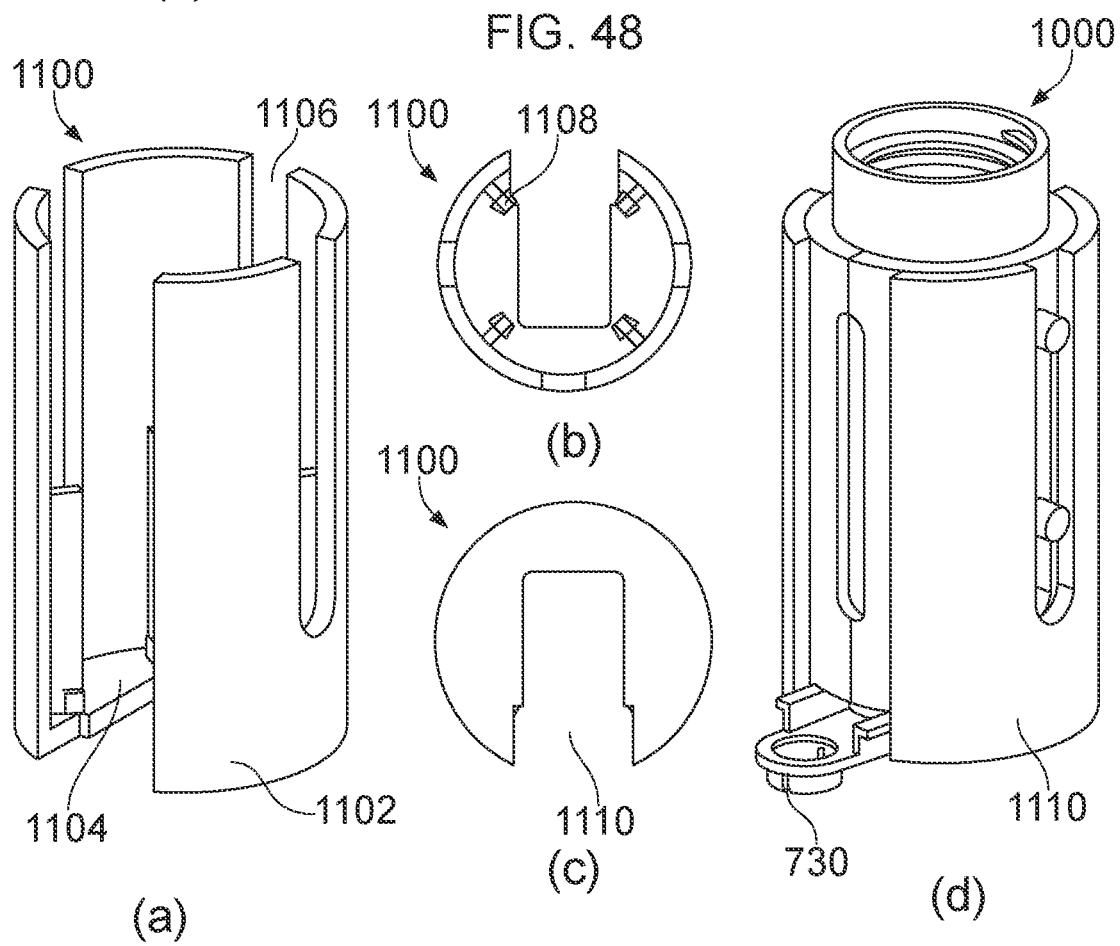
FIG. 49 illustrates (a) a perspective view of a holding mechanism, (b) a top view of a holding mechanism, (c) a bottom view of a holding mechanism, and (d) a perspective view of the holding mechanism having the connector of FIG. 36 therein.
Figure 50:
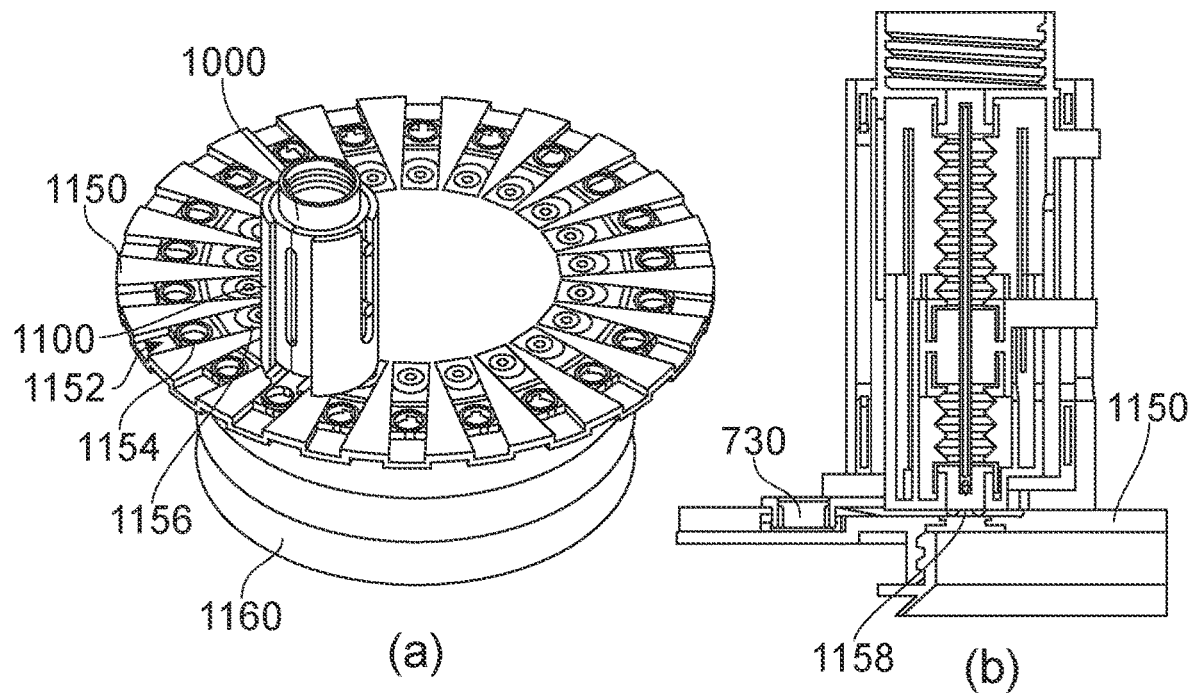
FIG. 50 illustrates (a) a perspective view of a holding mechanism, an interface plate, a bioreactor and the connector of FIG. 36, in use, and (b) a cross-sectional view of the holding mechanism, interface plate and connector of FIG. 36, in use.
Figure 51:
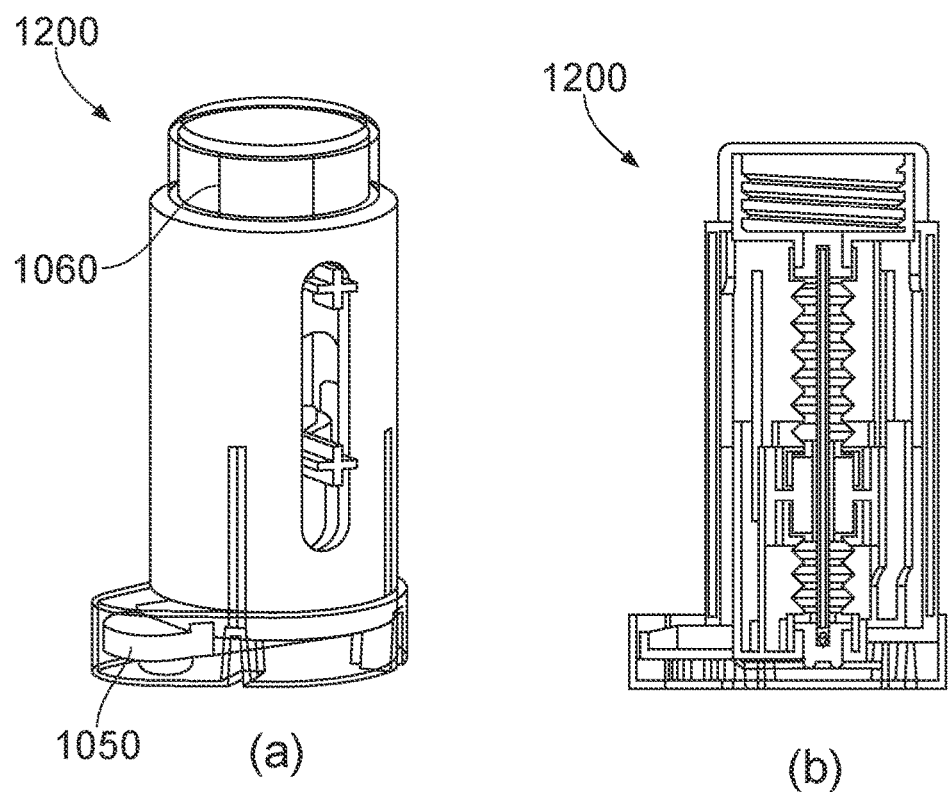
FIG. 51 illustrates (a) a perspective view, and (b) a cross-sectional view of a connector according to another embodiment of the present disclosure.
Figure 54:
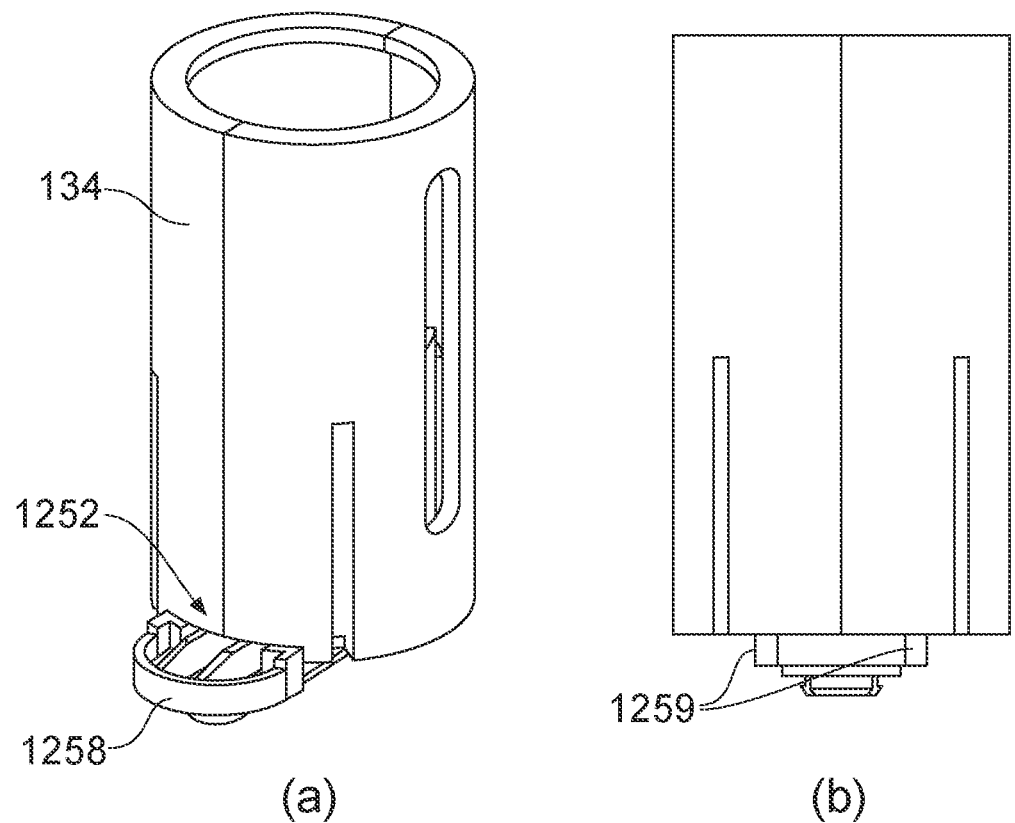
FIG. 54 illustrates (a) a perspective view, and (b) a side view of the outer sleeve of FIG. 52 having the aseptic seal system of FIG. 53 attached thereto.
Figure 55:
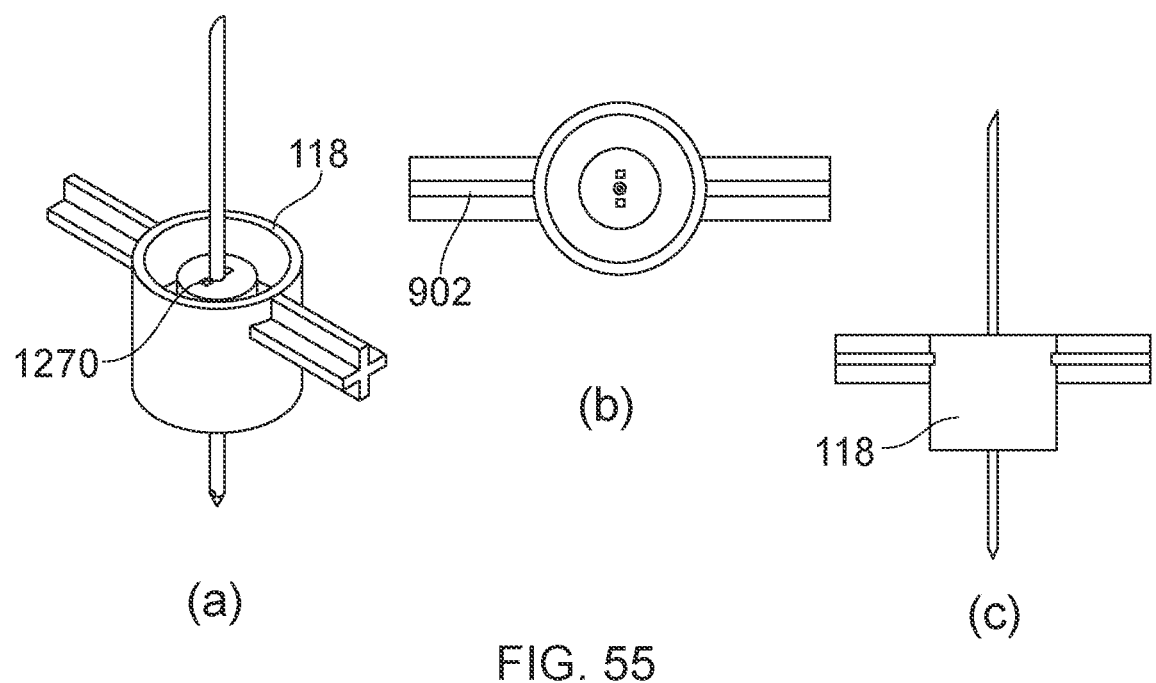
FIG. 55 illustrates (a) a perspective view, (b) a top view, and (c) a side view of the collar of the connector of FIG. 51.
Figure 56:
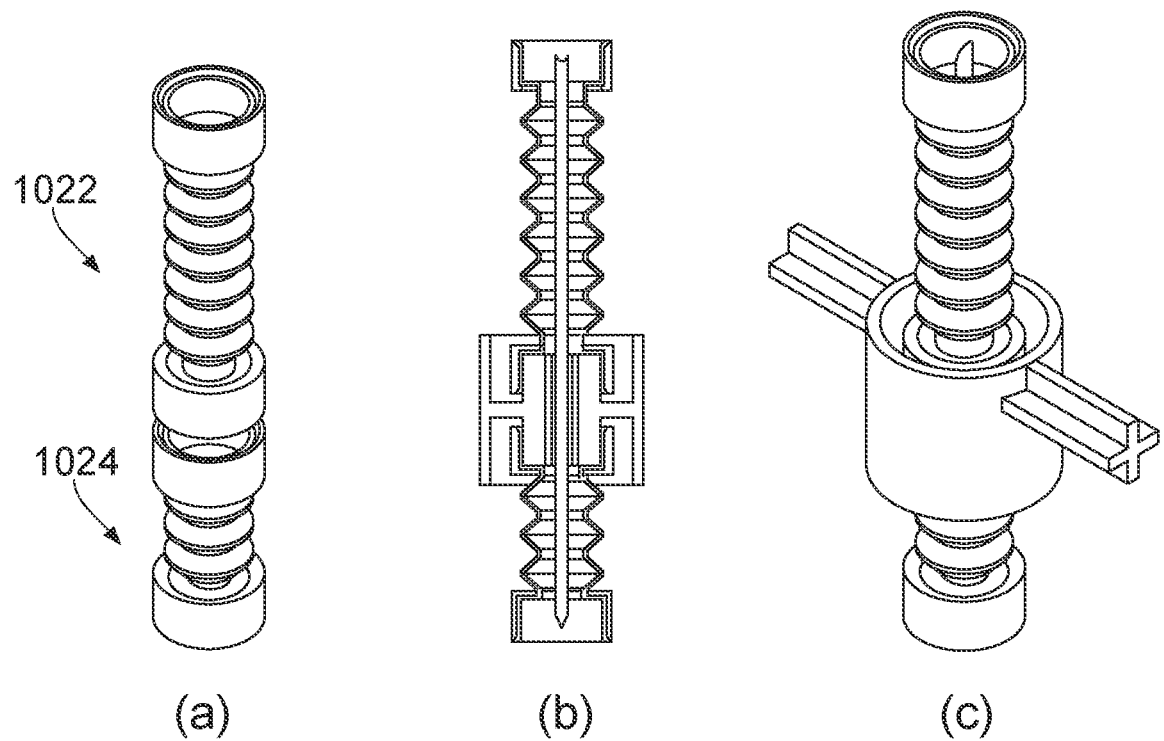
FIG. 56 illustrates (a) a perspective view of gaiters for use in the connector of FIG. 51, (b) a cross-sectional view, and (c) a perspective view of the gaiters and collar of the connector of FIG. 51.
Figure 57:
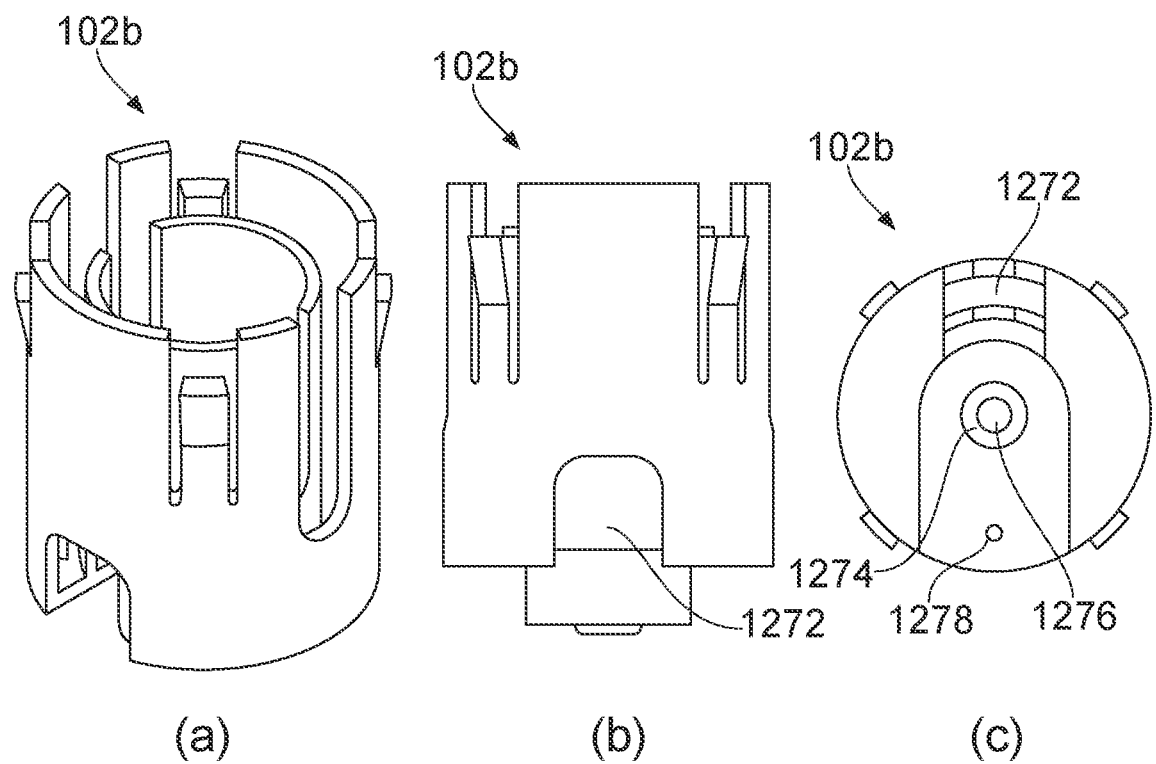
FIG. 57 illustrates (a) a perspective view, (b) a side view, and (c) a bottom view of the lower housing portion of the connector of FIG. 51.
Figure 58:
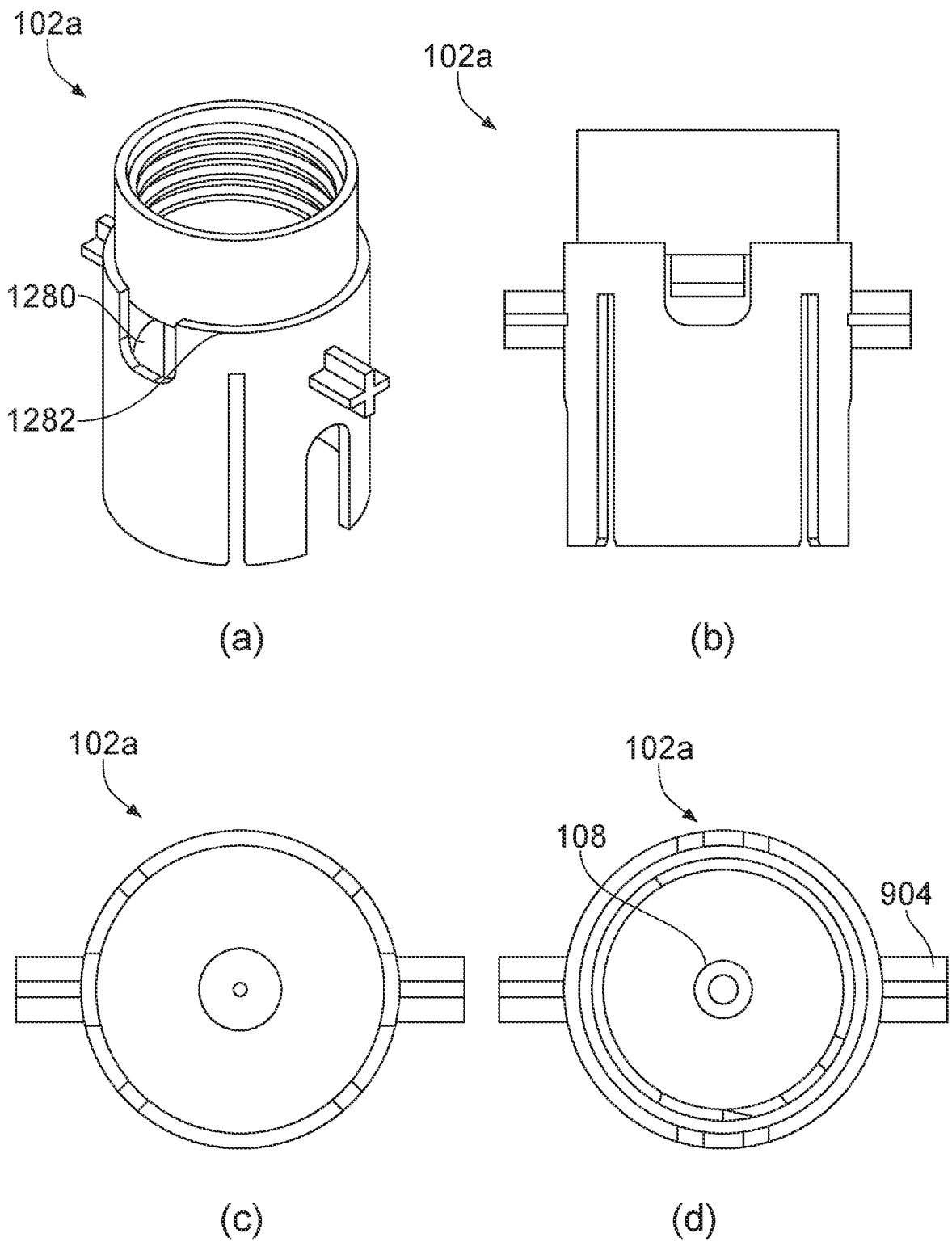
FIG. 58 illustrates (a) a perspective view, (b) a side view, (c) a bottom view, and (d) a top view of the upper housing portion of the connector of FIG. 51.

As best shown in FIGS. 36 to 38, the connector 1000 is similar in construction to the connector 900, except in that the actuatable lugs 902 of the collar 118, operably coupled to the hollow needle 112, and the actuatable lugs 904 of the upper housing portion 102a are aligned, and thus are each axially movable within the same longitudinal slot 1002 of the outer sleeve 134 of the connector 1000. Further, there are three actuatable lugs 902 of the collar 118, the first actuatable lug being offset from the second actuatable lug by 90°, the second actuatable lug being offset from the third actuatable lug by 90°, and the third actuatable lug being offset from the first actuatable lug by 180°. The same applies to the actuatable lugs 904 of the upper housing portion 102a, and the longitudinal slots 1002. Thus, the actuatable lugs 902, 904 generally form a T-shaped arrangement.

The lower housing portion 102b of the connector 1000 is shown in more detail in FIGS. 40(a) to 40(e). In particular, as also described elsewhere, the lower housing portion 102b includes an outer substantially cylindrical body 1004 and an inner substantially cylindrical body 1006. The outer body 1004 and the inner body 1006 are substantially concentric, spaced apart by an annular space 1008. The upper housing portion 102a, as described below, is arranged to be axially translatable over the outer body 1004. The inner body 1006 serves to hold the collar 118, and thus the hollow needle 112. The outer body 1004 is provided with a plurality of slots 1010 configured to allow the actuatable lugs 902 of the collar 118 (see FIG. 36), and the actuatable lugs 904 of the upper housing portion 102a (see FIG. 36), to protrude therethrough in use. Similarly, the inner body 1006 is provided with a plurality of slots 1012 configured to allow the actuatable lugs 902 of the collar 118 (see FIG. 36) to protrude therethrough in use.

The upper housing portion 102a of the connector 1000 is shown in more detail in FIGS. 41(a) to 41(e). In particular, as described above, the upper housing portion 102a includes a plurality of actuatable lugs 904 extending radially outwardly from the body of the upper housing portion 102a. Further, the upper housing portion 102a is provided with a plurality of slots 1014 configured to allow the actuatable lugs 902 of the collar 118 (see FIG. 36) to protrude therethrough in use. The upper housing portion 102a further includes a circumferentially protruding flange separating the threaded portion 107 from the remainder of the upper housing portion 102a.

The collar 118 of the connector 1000 is shown in more detail in FIGS. 42(a) to 42(e). The collar 118 is provided, as described above, with a plurality of actuatable lugs 902 protruding radially outwardly from the collar 118. As described above in relation to other embodiments, the collar 118 includes a substantially cylindrical outer body 1016, from which the actuatable lugs 902 protrude, and a substantially cylindrical inner body 1018, configured and arranged to operably engage the hollow needle 112, for example through a friction-fit, or the like. There is provided an annular recess 1020 between the inner and outer bodies 1016, 1018 configured to receive a spring in those embodiments in which a spring is utilized. As can be seen in FIGS. 42(a) to 42(e), the collar 118 is positioned off-center of the hollow needle 112, so that the collar 118 is positioned closer, i.e., more proximal or toward, the second end 116 of the hollow needle 112, or the collar 118 is positioned further away, i.e., more distal or away from, the first end 114 of the hollow needle 112.

Referring further to FIGS. 37 and 43(a) to 43(e), the hollow needle 112 is aseptically enclosed by first and second gaiters 1022, 1024. The first gaiter 1022 encloses an upper portion of the hollow needle 112, extending from the collar 118 to the first end 114 thereof. The second gaiter 1024 encloses a lower portion of the hollow needle 112, extending from the collar 118 to the second end 116 thereof. Thus, the gaiters 1022, 1024 ensure an aseptic environment for the hollow needle 112, and also serve to prevent accidental needle-stick injuries. The gaiters 1022, 1024 generally assume a concertina or bellows shape, that is they have a plurality of Z-folds, and may be composed of a flexible material, or resiliently deformable material, to allow for the gaiters 1022, 1024 to collapse during use. In some examples, the gaiters 1022, 1024 may be, independently, composed of low density polyethylene (LDPE), a thermoplastic elastomer, or the like. The first gaiter 1022 is secured at one end to the upper housing portion 102a and at its other end to the collar 118, through any suitable means such as a gaiter clip 1026, preferably composed of high density polyethylene (HDPE), an adhesive, heat welding or the like. The second gaiter 1024 is similarly secured at one end to the lower housing portion 102b and at its other end to the collar 118, through any suitable means such as a gaiter clip 1026, preferably composed of high density polyethylene (HDPE), an adhesive, heat welding or the like.

The outer sleeve 134 of the connector 1000 is shown in more detail in FIGS. 44(a) to 44(f). As shown in FIGS. 44(a) and 44(b), the outer sleeve 134 includes two generally half-pipe portions 134a, 134b that are substantially mirror images of one another. Each half-pipe portion 134a, 134b of the outer sleeve 134 includes a side wall 1032 terminating in a base 1034. The side wall 1032 includes a plurality of longitudinal slots 1030, at least a portion of such slots being configured and arranged to allow the actuatable lugs 902, 904 to protrude therethrough in use, extending axially within the side wall 1032. The base 1034 further includes an aseptic seal system receiving region 1036, configured and arranged to receive an aseptic seal system, such as an aseptic seal system 730 as described above in relation to FIGS. 19, 20 and 24(a) to 24(e) and shown in FIGS. 36 and 37. The receiving region 1036 is shaped in a complementary manner to the aseptic seal system 730. The receiving region 1036 may include one or more cooperating features, such as a rail guide, that cooperate with one or more features of the aseptic seal system, such as a rail. The receiving region 1036 may expose a portion, or all of, the second septum seal (not shown) in use. The side wall 1032 includes one or more longitudinal grooves 1038 terminating in respective aperture(s) 1040 in the base 1034. The longitudinal grooves 1038 and apertures 1040 are configured and arranged to allow one or more pins of an actuating mechanism (not shown) to activate the needle-safe features, i.e., the tongues, of the lower housing portion. Further, the longitudinal grooves 1038 and apertures 1040 may cooperate with a retention feature, formed as part of an instrument, housing, holding mechanism or incubator, to limit movement of the connector.

FIGS. 45(a) to 45(e) illustrate the upper housing portion 102a, the lower housing portion 102b, the hollow needle 112, the collar 118 and the gaiters 1022, 1024 once assembled. As can be seen, the actuatable lugs 902, 904 of the collar 118 and the upper housing portion 102a respectively protrude outwardly through various slots as described above.

FIGS. 46(a) to 46(d) illustrate the assembled components of FIGS. 45(a) to 45(e), further including the outer sleeve 134 of FIGS. 44(a) to 44(f) assembled thereto. As can be seen, the second septum seal 110, prior to assembly of an aseptic seal system, is exposed within the receiving region 1036 in the base 1034 of the outer sleeve 134. In this particular embodiment, the second septum seal 110 is formed as a co-molded material to the lower body portion having an annular raised region defining a flat piercing region therein.

FIGS. 47(a) to 47(f) illustrate an aseptic seal system 730, similar to that described above, for use with the connector 1000. FIG. 47(f) illustrates the aseptic seal system 730 received within the receiving region 1036 of the outer sleeve 134.

FIGS. 48(a) to 48(c) illustrate a transit cover 1050 and a transit cap 1060 for use with the connector 1000. The transit cover 1050 includes a hollow body that is sized and shaped to be complementary to the connector 1000, so as to receive the connector 1000 within the hollow body. The transit cap 1060 is sized and shaped to be complementary with the proximal end 106 of the connector 1000, and is specifically shaped and sized to account for the shape and size of the aseptic seal system 730.

FIGS. 49(a) to 49(d), 50(a) and 50(b) illustrate a holding mechanism 1100, optionally formed as part of an instrument, housing or incubator, for holding the connector 1000, in use. As best shown in FIGS. 49(a) to 49(d), the holding mechanism 1100 includes a generally cylindrical side wall 1102 terminating in a base 1104. The side wall 1102 includes a plurality of slots 1106 configured and arranged to receive, or otherwise allow to protrude, the protruding actuatable lugs 902, 904 of the connector therethrough. The base 1104 is configured to allow the connector 1000 to be held within the cavity formed by the base 1104 and the side wall 1102. The base 1104 includes a plurality of notches 1108, or pins or the like, upstanding therefrom and parallel to the side wall 1102, configured and arranged to engage with, and protrude through, the longitudinal grooves 1038 and apertures 1040 formed in the outer sleeve 134 of the connector 1000. In this way, the connector 1000 can be easily located in the correct position. The notches 1108 each include an enlarged head complementary in size and shape to the apertures 1040 of the outer sleeve 134 to prevent movement of the connector 1000 within the holding mechanism 1100, in use. Further, the notches 1108 engage with the tongues 708 (see FIGS. 21(a) to 21(e)) via the slots 724 (see FIGS. 22(a) to 22(e)) in use, so as to activate the tongues 708 and allow for needle-safe activation of the upper housing portion 102a and the lower housing portion 102b. The base 1104 further includes a cut-out region 1110 configured to receive the aseptic seal system 730 of the connector 1000.

FIGS. 50(a) and 50(b) illustrate the connector 1000 and the holding mechanism 1100 in use with an interface plate 1150 and a bioreactor 1160. The interface plate 1150 is formed as a lid for the bellows-based bioreactor 1160. The interface plate 1150 is formed with a plurality of aseptic seal systems 1152 that are complementary to the aseptic seal system 730. In particular, each aseptic seal system 1152 includes a protruding portion 1154, configured and arranged to couple with a portion of the clip portion 732 of the aseptic seal system 730, such as the aperture 738 (see also FIGS. 47(a) to 47(f)). Further, each aseptic seal system includes an aseptic membrane 1156, configured to couple to an aseptic membrane 734 of the aseptic seal system 730 (see also FIG. 47(a)). The coupling of the membranes 734, 1156 may be by virtue of an adhesive, heat welding, or the like. Once coupled, an actuation device (not shown) may remove the coupled aseptic seal systems 730, 1152, thereby exposing the second septum seal 110 to a septum seal 1158 of the interface plate 1150.

As shown in FIGS. 51 to 62, there is provided another embodiment of a connector 1200 for connecting two volumes of fluid. The connector 1200 is the same construction as connector 1000, described in relation FIGS. 36 to 50, except for the details listed below. Like reference numerals denote like features.

The connector 1200 includes a pair of actuatable lugs 902, protruding from the collar 118, rather than three actuatable lugs as shown in the connector 1000. The pair of actuatable lugs 902 extends in opposing directions, 180° apart, with respect to one another. In other words, the actuatable lugs 902 extend radially outwardly and are diametrically opposed to one another. Similarly, the connector 1200 includes a pair of actuatable lugs 904, protruding from the upper housing portion 102a, rather than three actuatable lugs as shown in connector 1000. The pair of actuatable lugs 904 extends in opposing directions, 180° apart, with respect to one another. In other words, the actuatable lugs 904 extend radially outwardly and are diametrically opposed to one another. Further, both pairs of actuatable lugs 902, 904 include a substantially cross-shaped, or crucifix-shaped, cross-section. These features allow for ease of automation of the actuation mechanism.

The connector 1200 in FIG. 51(a) is shown with a transit cover 1050 and a transit cap 1060, which are complementary to respective ends of the connector 1200. Notably, the transit cover 1050 serves to cover the proximal end of the connector 1200 only, and the transit cap 1060 serves to cover the distal end of the connector 1200 only. A portion of the connector 1200 therefore remains uncovered. In some examples, not shown, the transit cover 1050 and cap 1060 may be integrally formed so as to provide a sterile package for the connector 1200, which would be packaged within the transit cover 1050 and cap 1060 in a manner substantially as illustrated in FIG. 51(a).

FIGS. 52(a) and 52(b) illustrate the outer sleeve 134 of the connector 1200. As can be seen, the outer sleeve 134 only includes a pair of opposing longitudinal slots 1030 arranged in the side wall 1032 of the outer sleeve 134. As described above, such slots 1030 are arranged to allow the actuatable lugs 902, 904 to extend, or otherwise protrude, therethrough. The outer sleeve 134 may include two half-pipe portions, as described above, or may be formed as an integral component. The feature 134c indicates a seam, weld or the like between adjacent portions. The outer sleeve 134 may be composed of polycarbonate, acrylonitrile butadiene styrene (ABS), high impact polystyrene sheet (HIPS), or another appropriate material.

FIGS. 53(a) to 53(c) illustrate another embodiment of an aseptic seal system 1250 of the connector 1200. The aseptic seal system 1250 includes a clip portion 1252 and an aseptic membrane 1254. Similar to the aseptic seal system 730 shown in FIGS. 19, 20, 24(a) to 24(e), the clip portion 1252 is preferably composed of high density polyethylene (HDPE), and is configured and arranged to clip to the outer sleeve 134 of the connector 1200 in use. In this particular example, the clip portion 1252 includes a pair of substantially parallel lateral rails 1256 connected to a semi-circumferential wall 1258, and having a shoulder 1259. The clip portion 1252 also includes a protrusion 1260, protruding from a base 1262 of the clip portion 1252, configured to engage and retain the aseptic membrane 1254. To this end, the protrusion 1260 may include one or more clips. The lateral rails 1256 are arranged to cooperate with a corresponding rail receiving portion of the outer sleeve 134 (see FIG. 52(a)). The clip portion 1252 is also provide with a plurality of strengthening ribs 1263, extending parallel to the rails 1256.

The aseptic membrane 1254 may be formed as an aseptic paper seal, a polyethylene film, or the like, and is generally coupled to the clip portion 1252 by virtue of an aperture coupled to the protrusion 1260 and retained in place by one or more clips. There is also provided an affixing position 1265 for affixing the aseptic membrane 1254 to the connector 1200 in use. The affixing position 1265 may cooperate with a corresponding feature of the connector 1200, or may serve as a guide to properly position the aseptic membrane 1254 for heat welding, adhering or the like, in use.

Referring further to FIGS. 54(a) and 54(b), the clip portion 1252 is slidably arranged within the rail receiving portion of the outer sleeve 134. The semi-circumferential wall 1258 forms the outermost portion of the clip portion 1252. The shoulders 1259 are arranged and configured to be engaged by a pushing portion of an actuation mechanism, so as to slidably remove the clip portion 1252, and thus remove the aseptic membrane 1254 from the second septum seal 110, in use.

FIGS. 55(a) to 55(c) illustrate a collar 118 of the connector 1200. The collar 118 is as substantially described above, and further includes a pair of apertures 1270 to allow the passage of air between an upper portion of the collar 118 and a lower portion of the collar 118. In this way, a smooth axial translation of the collar 118 in use is achieved. It may be preferable for the collar 118 to be composed of acrylonitrile butadiene styrene (ABS), high impact polystyrene sheet (HIPS), polycarbonate, or a like material. It may be preferable for the hollow needle 112 to be composed of stainless steel.

FIGS. 56(a) to 56(c) illustrate first and second gaiters 1022, 1024, which are substantially as described in relation to FIGS. 37 and 43(a) to 43(e). The gaiters may be composed of low density polyethylene (LDPE), a thermoplastic elastomer (TPE), silicon, or a like material. The gaiter clips, as described above, may be composed of high density polyethylene (HDPE).

FIGS. 57(a) to 57(c) illustrate the lower housing portion 102b of the connector 1200. The lower housing portion 102b further includes an access slot 1272 to enable a user to access the second gaiter 1024, in use (see FIG. 60(b)). Further, the second septum seal 110 is provided with a raised annular region 1274, enclosing a flat portion 1276 therein for piercing, in use. There is also provided a fixing point 1278 for fixing an aseptic membrane (not shown) to the lower housing portion 102b, specifically over the second septum seal 110. The lower housing portion 102b may be composed of polycarbonate, acrylonitrile butadiene styrene (ABS), high impact polystyrene sheet (HIPS), or a like material. The second septum seal 110 may be composed of a thermoplastic elastomer (TPE), silicon, or the like.

FIGS. 58(a) to 58(d) illustrate the upper housing portion 102a of the connector 1200. The upper housing portion 102a further includes an access slot 1280 to enable a user to access the first gaiter 1022, in use (see FIG. 60(b)). Further, the protruding circumferential flange of the previous embodiment of the upper housing portion 102a has been replaced by a step 1282. The upper housing portion 102a may be composed of polycarbonate, acrylonitrile butadiene styrene (ABS), high impact polystyrene sheet (HIPS) or a like material. The first septum seal 108 may be composed of a thermoplastic elastomer (TPE), silicon, or the like.

Figure 59:
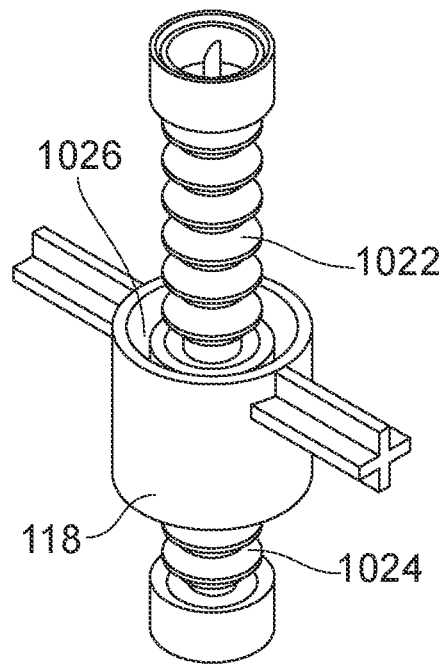
FIG. 59 illustrates a perspective view of the first step of the assembly of the connector of FIG. 51.
Figure 60:
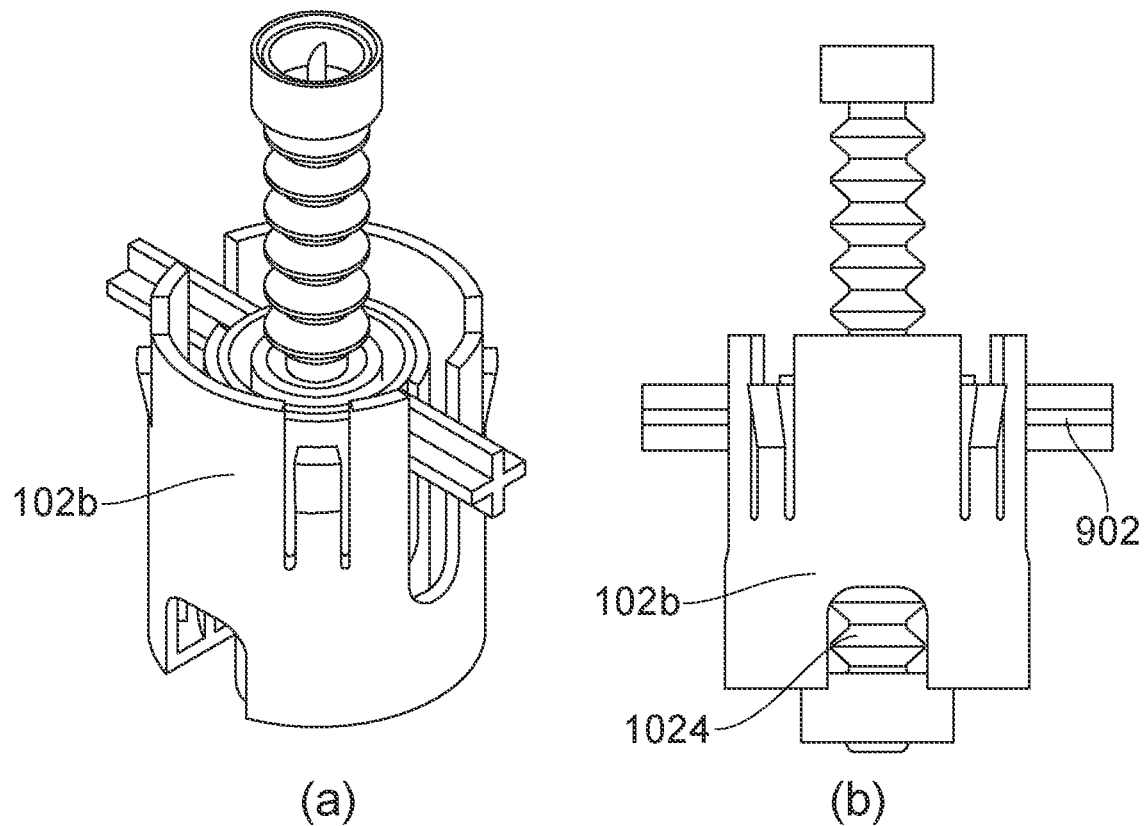
FIG. 60 illustrates (a) a perspective view, and (b) a side view of the second step of the assembly of the connector of FIG. 51.
Figure 61:
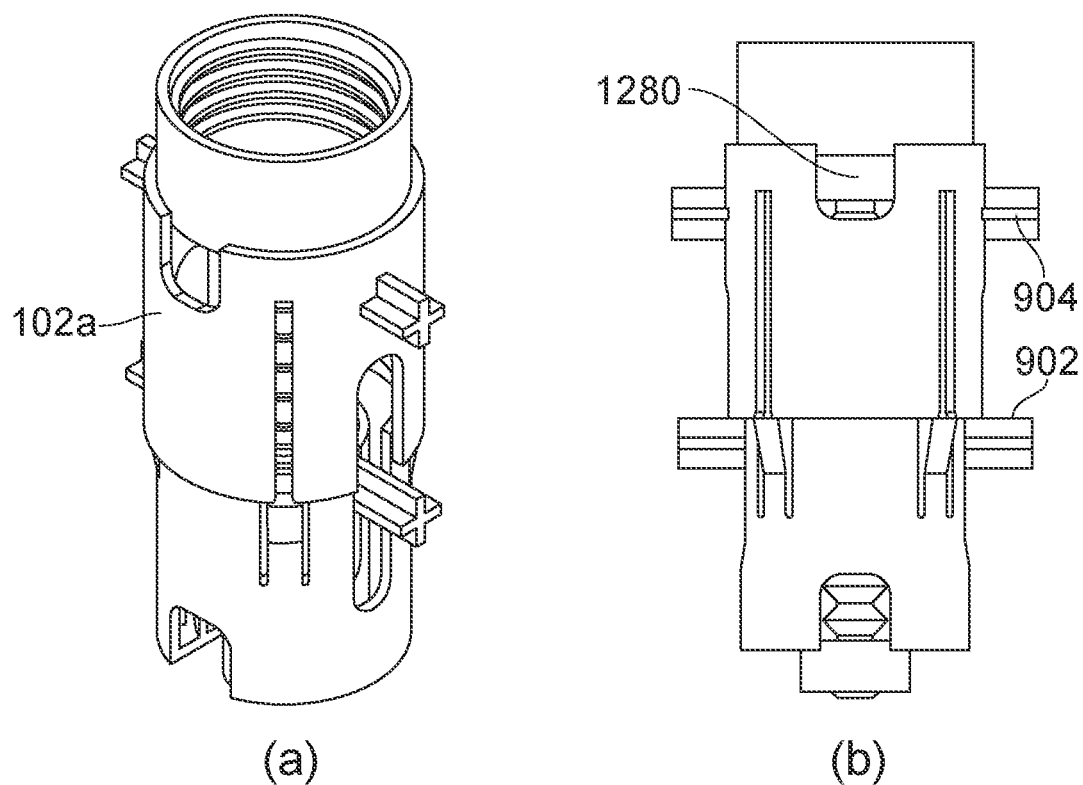
FIG. 61 illustrates (a) a perspective view, and (b) a side view of the third step of the assembly of the connector of FIG. 51.
Figure 62:
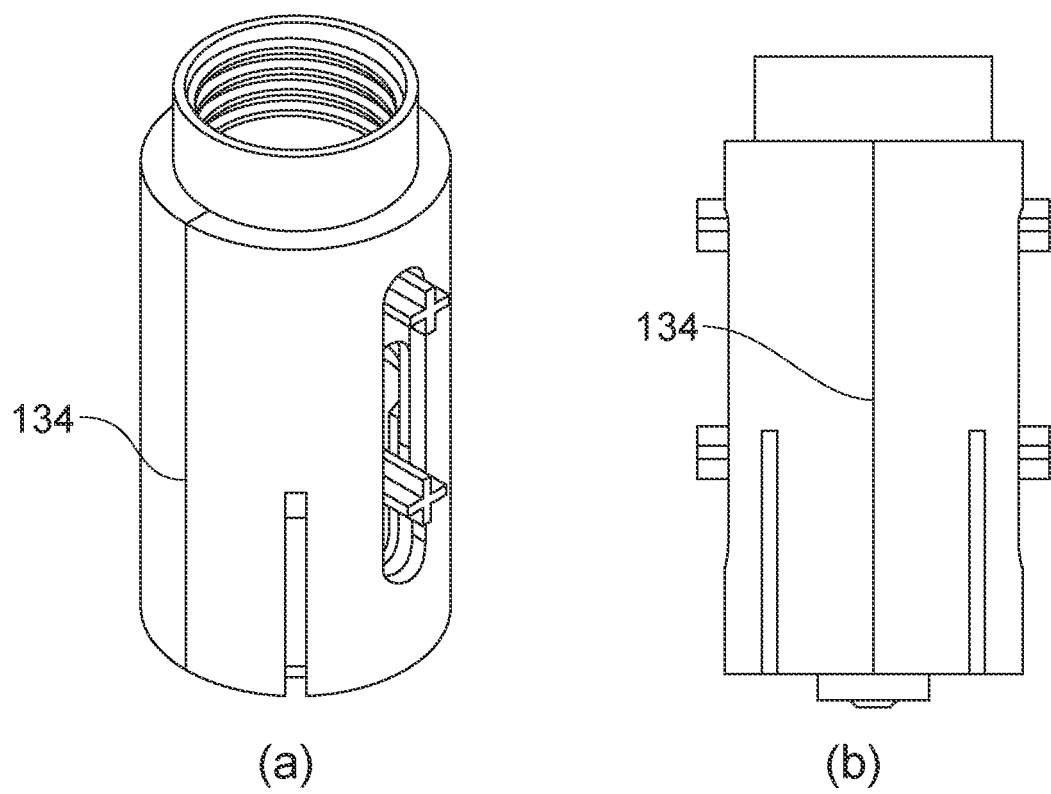
FIG. 62 illustrates (a) a perspective view, and (b) a side view of the fourth step of the assembly of the connector of FIG. 51.
Figure 63:
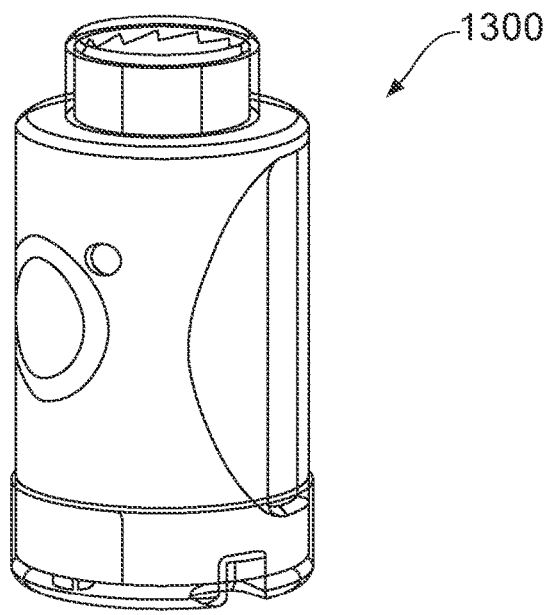
FIG. 63 illustrates a connector according to another embodiment of the present disclosure.
Figure 64:
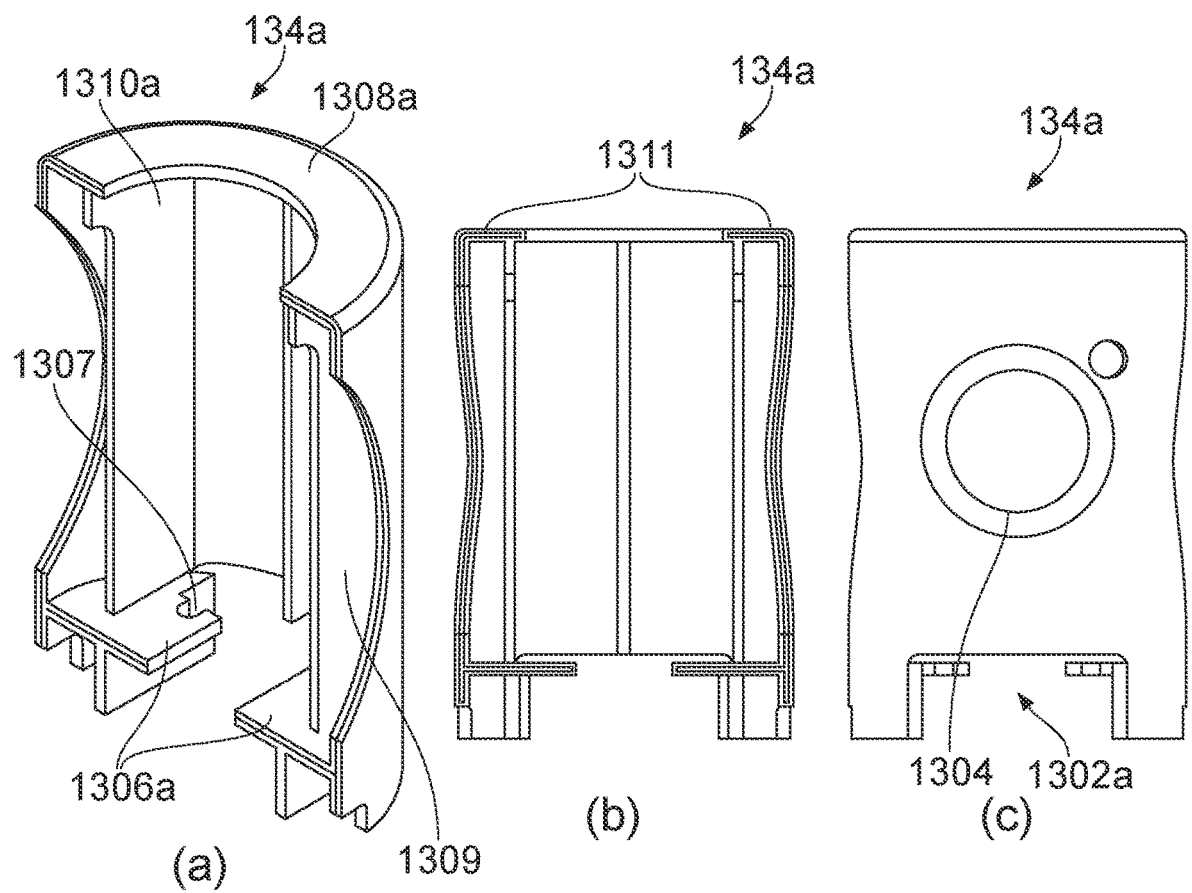
FIG. 64 illustrates (a) a perspective view, (b) a rear view, and (c) a front view of one portion of the outer sleeve of the connector of FIG. 63.
Figure 65:
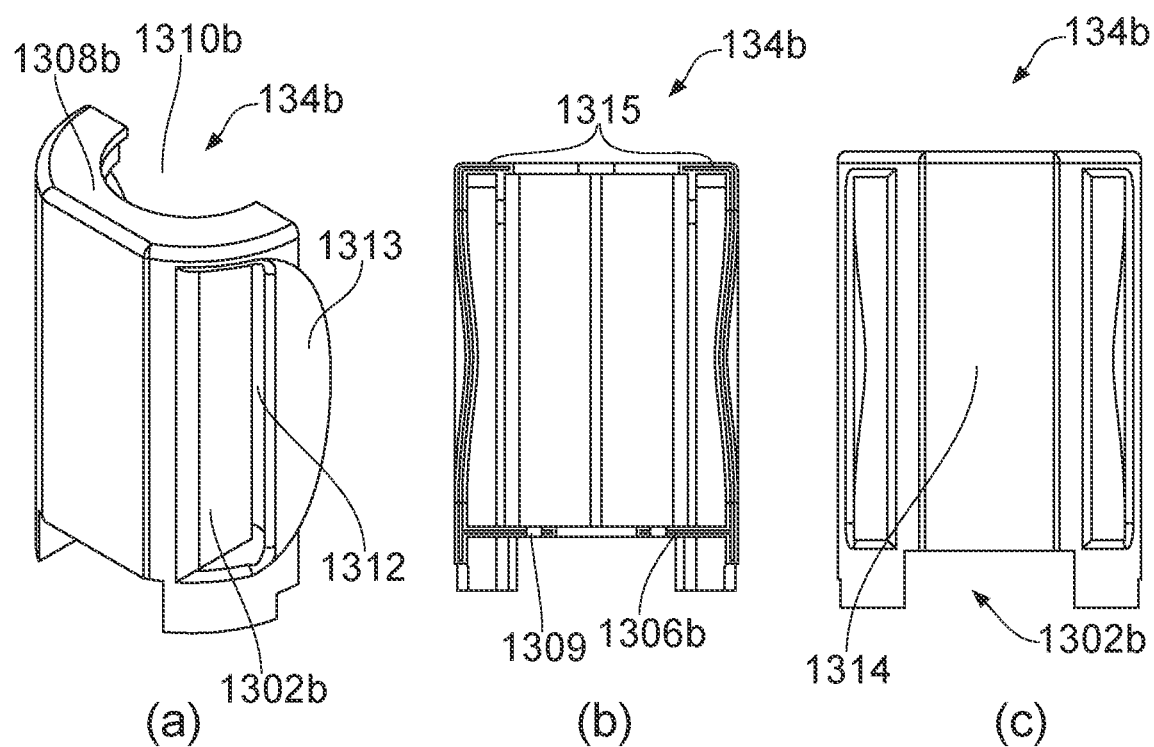
FIG. 65 illustrates (a) a perspective view, (b) a rear view, and (c) a front view of another portion of the outer sleeve of the connector of FIG. 63.
Figure 66:
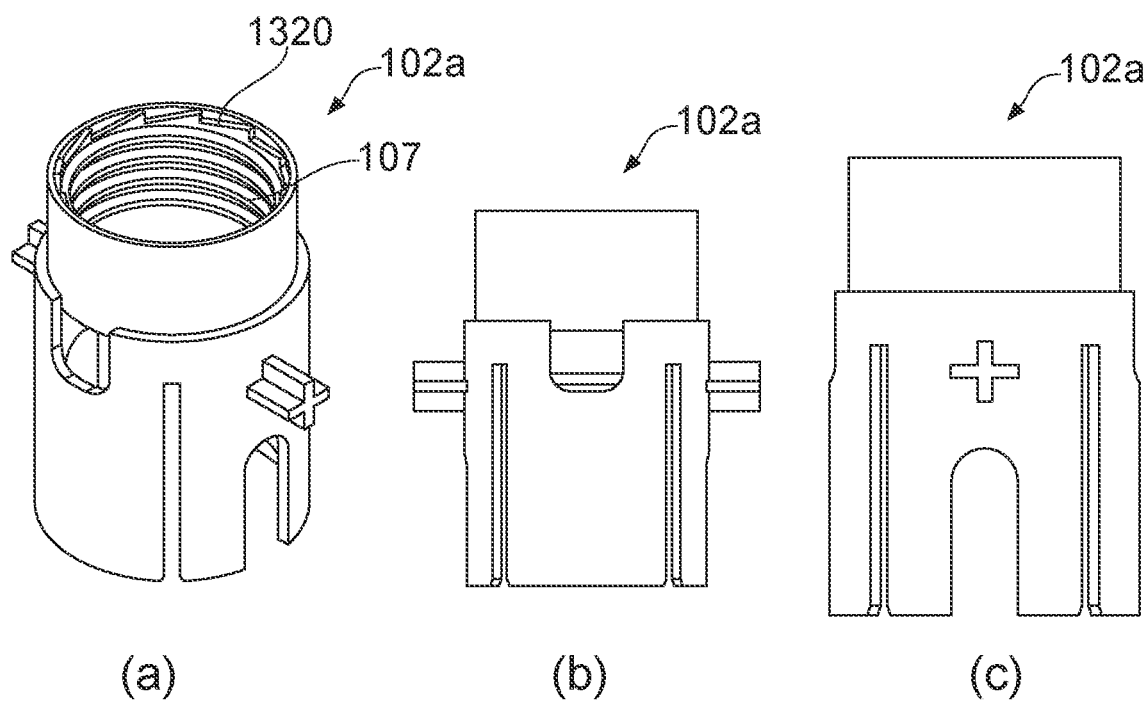
FIG. 66 illustrates (a) a perspective view, (b) a side view, and (c) another side view of the upper housing portion of the connector of FIG. 63.
Figure 67:
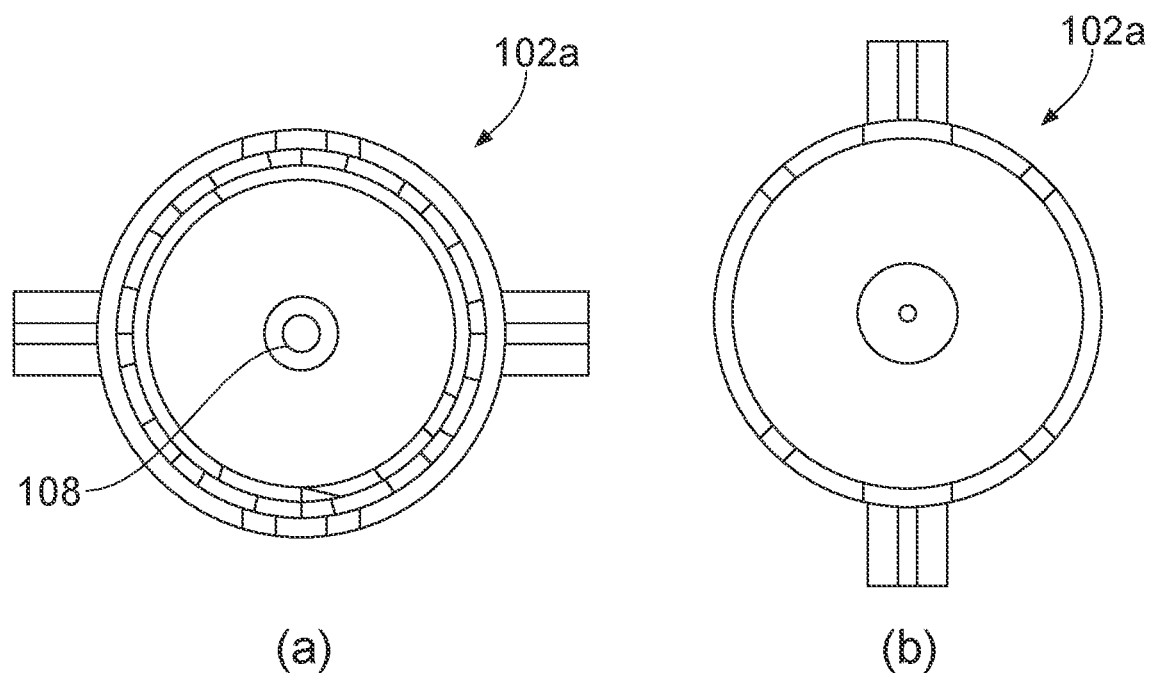
FIG. 67 illustrates (a) a top view, and (b) a bottom view of the upper housing portion of the connector of FIG. 63.
Figure 68:
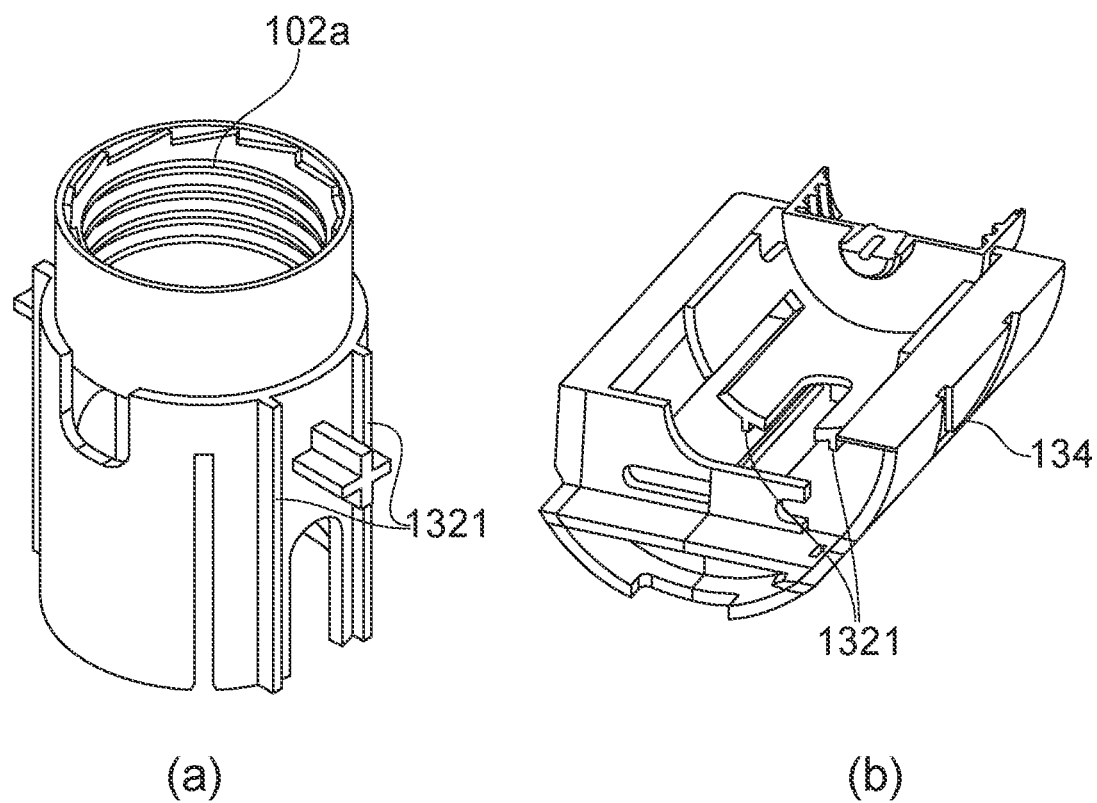
FIG. 68 illustrates a perspective view of (a) another embodiment of the upper housing portion of the connector of FIG. 63, and (b) the upper housing portion of (a) assembled to an outer sleeve.
Figure 69:
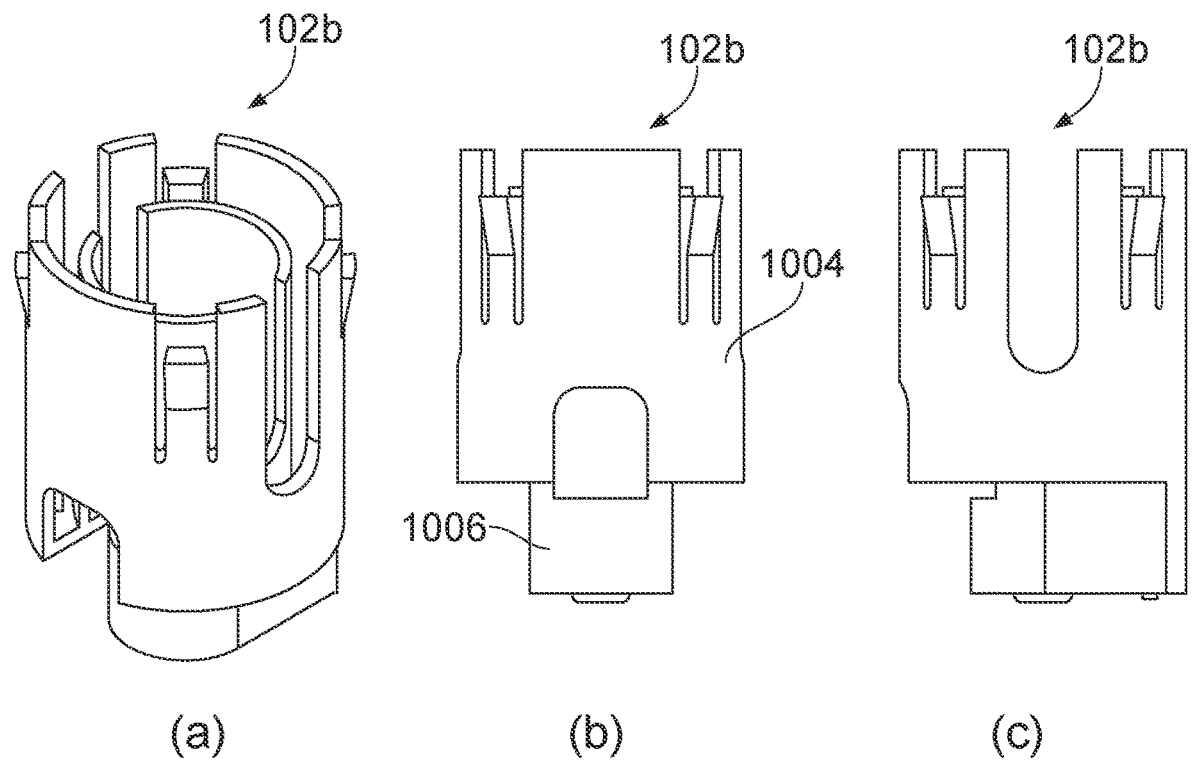
FIG. 69 illustrates (a) a perspective view, (b) a front view, and (c) a side view of the lower housing portion of the connector of FIG. 63.
Figure 70:
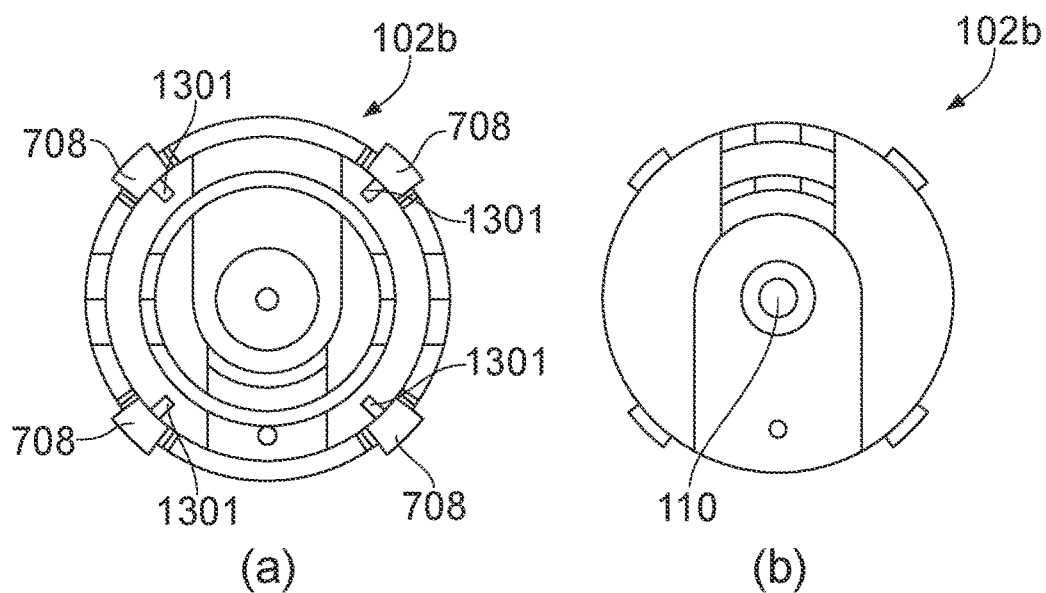
FIG. 70 illustrates (a) a top view, and (b) a bottom view of the lower housing portion of the connector of FIG. 63.
Figure 71:
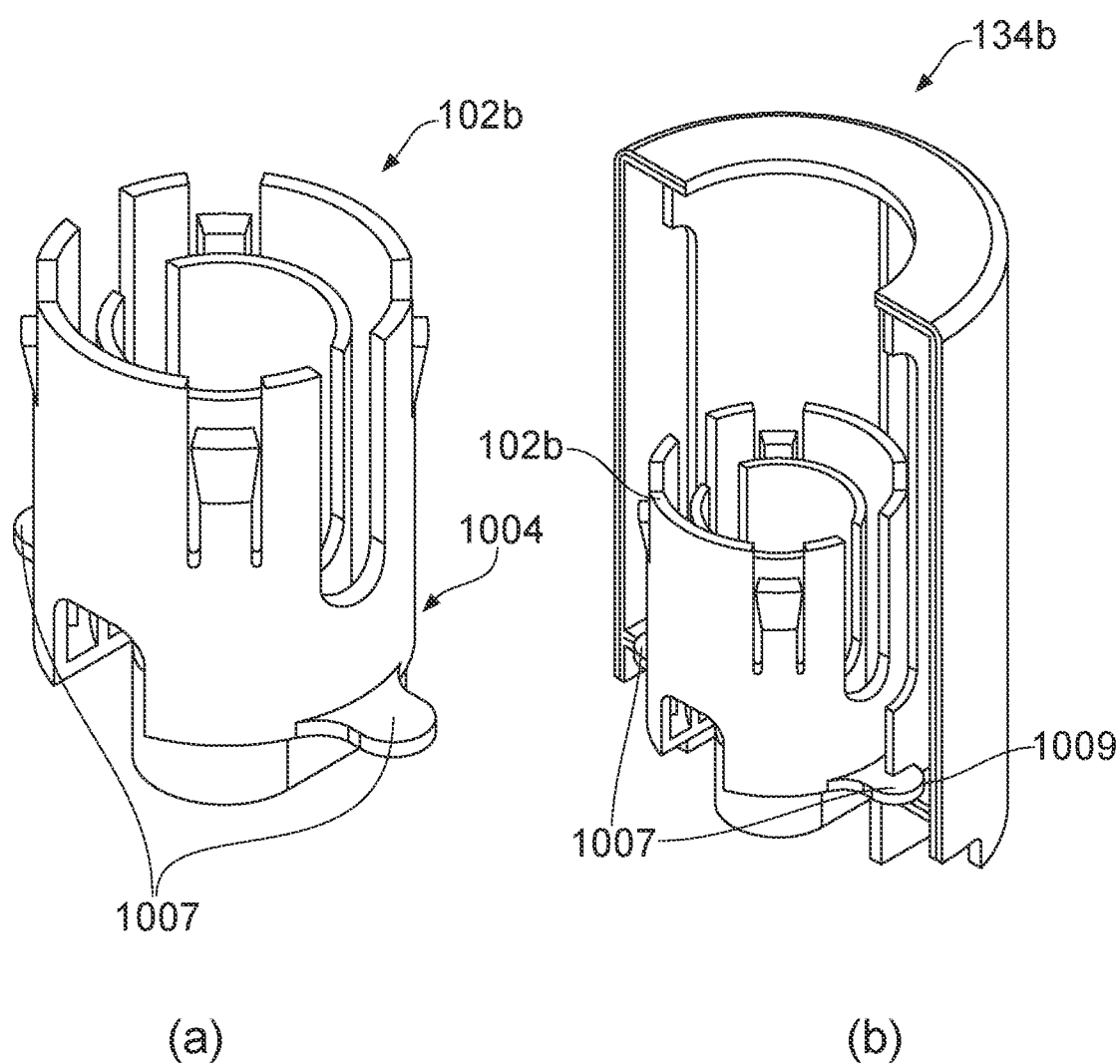
FIG. 71 illustrates a perspective view of (a) another embodiment of the lower housing portion of the connector of FIG. 63, and (b) the lower housing portion of (b) assembled to an outer sleeve.
Figure 72:
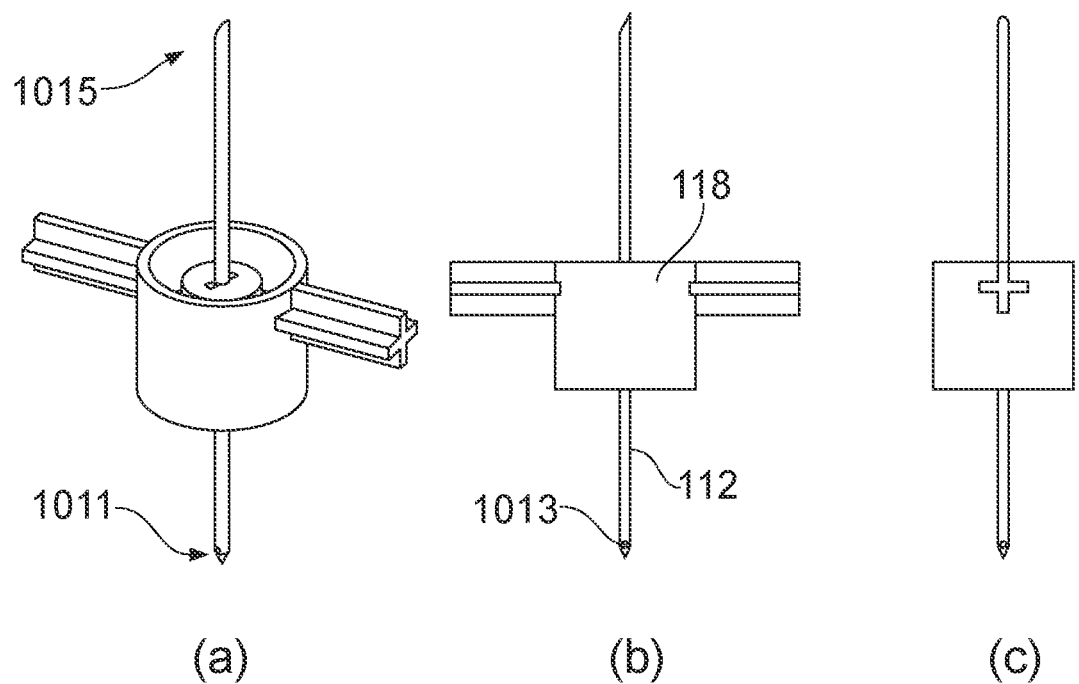
FIG. 72 illustrates (a) a perspective view, (b) a side view, and (c) another side view of the collar of the connector of FIG. 63.
Figure 73:
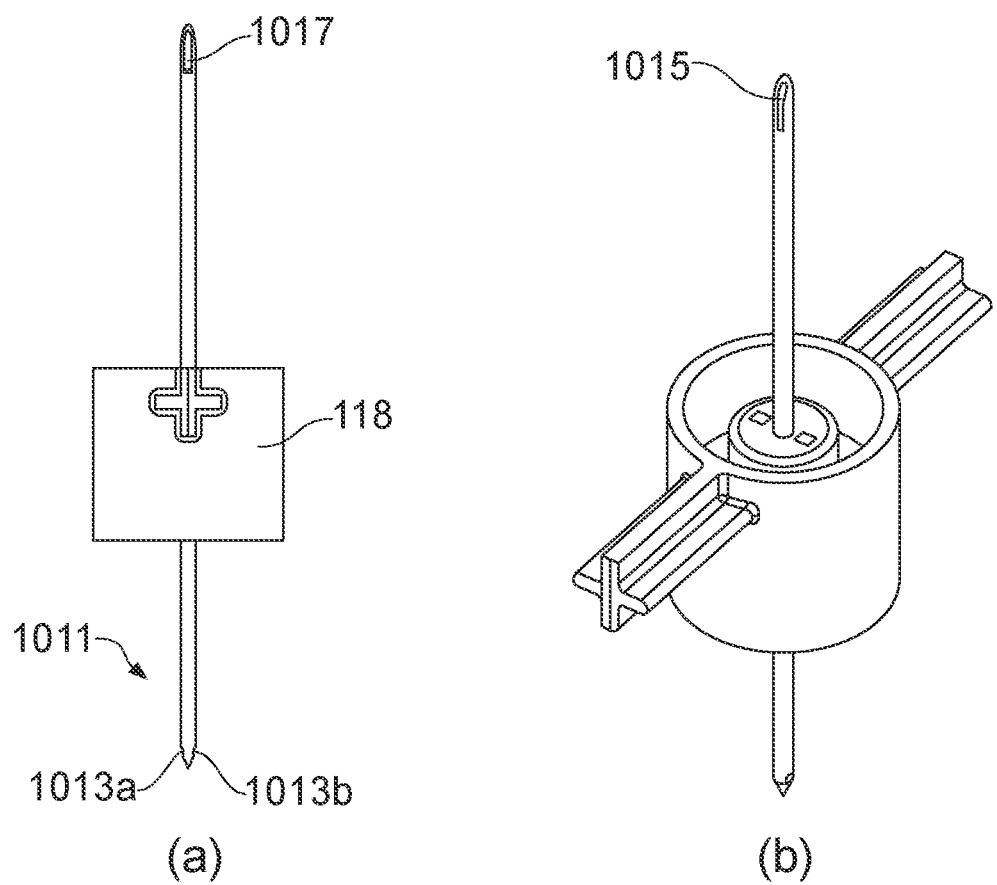
FIG. 73 illustrates (a) a side view, and (b) a perspective view of another embodiment of the hollow needle and collar of the connector of FIG. 63.
Figure 74:
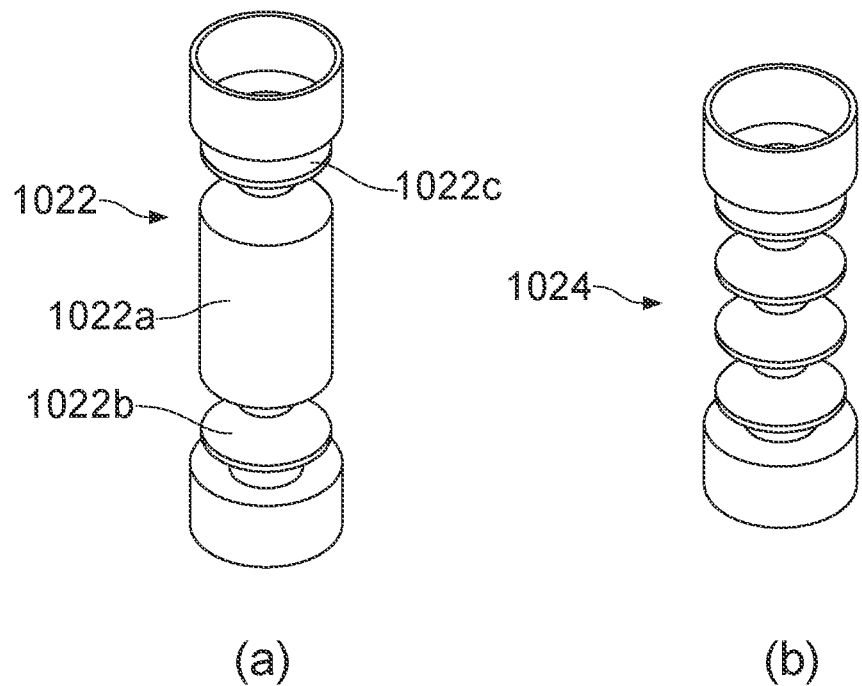
FIG. 74 illustrates (a) a perspective view of a first gaiter, and (b) a perspective view of a second gaiter of the connector of FIG. 63.
Figure 75:
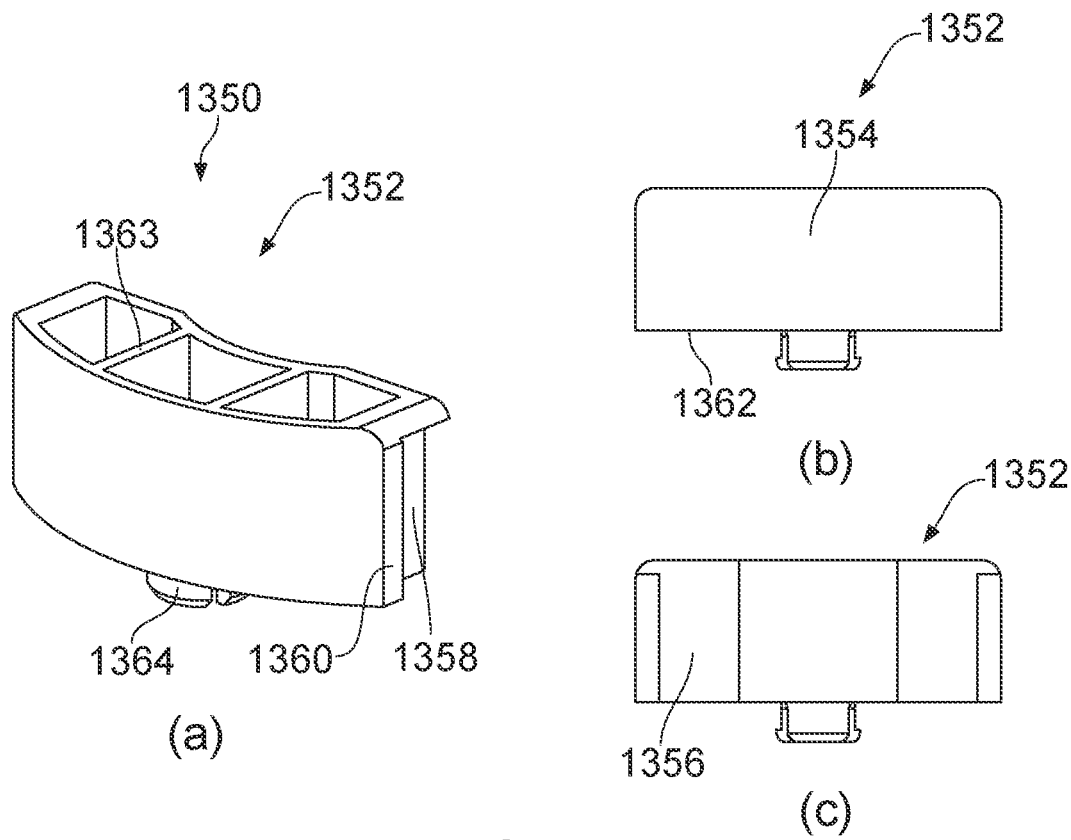
FIG. 75 illustrates (a) a perspective view, (b) a front view, and (c) a rear view of a clip portion of an aseptic seal system for use in the connector of FIG. 63.
Figure 76:
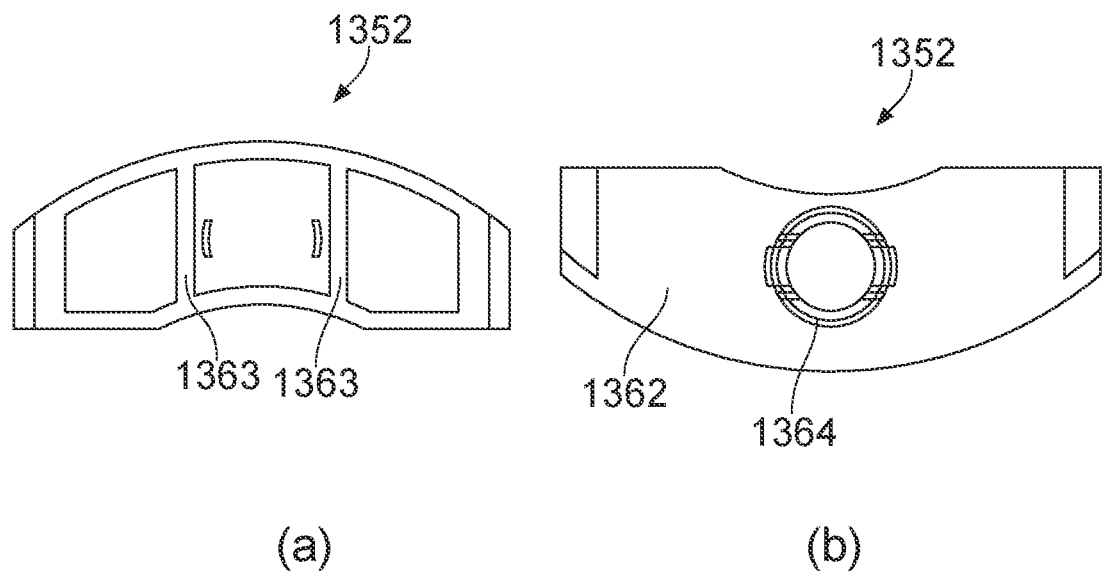
FIG. 76 illustrates (a) a top view, and (b) a bottom view of the clip portion of FIG. 75.

FIGS. 59 to 62 illustrate the assembly of the connector 1200. Firstly, the gaiters 1022, 1024 are clipped, for example via clip 1026 or otherwise coupled, to the collar 118 (FIG. 59). Secondly, the collar 118 and coupled gaiters 1022, 1024 are assembled into the lower housing portion 102b (FIGS. 60(a) and 60(b)). The actuatable lugs 902 are also shown as protruding outwardly through the lower housing portion 102b. Thirdly, the upper housing portion 102a is arranged over the lower housing portion 102b (FIGS. 61(a) and 61(b)). The actuatable lugs 902, 904 are shown as protruding outwardly, configured to be received within a corresponding slot of the outer sleeve. Fourthly, the outer sleeve 134 is arranged over the upper and lower housing portions 102a, 102b, and secured in place, for example, by welding or clipping (FIGS. 62(a) and 62(b)) to provide the assembled connector 1200.

As shown in FIGS. 63 to 75, there is provided another embodiment of a connector 1300 for connecting two volumes of fluid. The connector 1300 is the same construction as connector 1000, described in relation FIGS. 51 to 62, except for the details listed below. Like reference numerals denote like features.

FIGS. 64(a) to 64(c) illustrate a first portion 134a, formed as a front portion, of the outer sleeve 134. The first portion 134a includes an aseptic seal system access slot 1302a in a side wall 1032 of the first portion 134a. There is also provided a recess for indicia 1304 on the outer surface of the side wall 1032. There is also provided a shelf 1306a extending laterally from the inner surface of the side wall 1032a, arranged to hold and retain the inner components of the connector 1300, as described further below. The shelf 1306a also includes a rail receiving portion for receiving an aseptic seal system. Further, the shelf 1306a includes one or more apertures 1307, two apertures in the present embodiment, configured and arranged to allow one or more pins of an actuation mechanism (not shown) to protrude therethrough to activate the tongues 708 (see FIG. 69(a) as discussed below) to provide a needle-safe activation of the upper housing portion 102a and the lower housing portion 102b, in a similar manner to that described in relation to FIGS. 21(a) to 21(e), 22(a) to 22(e) and 44(a) to 44(f). The top wall 1308a of the first portion 134a includes an aperture 1310a to allow for the upper housing portion 102a (see below) to protrude therethrough. The first portion 134a also includes a recess 1311 adjoining the side wall 1032a to the top wall 1308a to allow for the two portions to be welded together, in use. The side wall 1032a further includes an arcuate slot 1309 for receiving a portion of the second portion 134b as described below.

FIGS. 65(a) to 65(c) illustrate a second portion 134b, formed as a rear portion, of the outer sleeve 134. There is also provided a shelf 1306b extending laterally from the inner surface of the side wall 1032b, arranged to hold and retain the inner components of the connector 1300, as described further below. The shelf 1306b includes one or more slots 1309, two slots in the present embodiment, configured and arranged to allow one or more pins of an actuation mechanism (not shown) to protrude therethrough to activate tongues 708 (see FIG. 69(a) as discussed below) to provide a needle-safe activation of the upper housing portion 102a and the lower housing portion 102b, in the same manner described above in relation to apertures 1307 of FIGS. 64(a) and 64(b).

The second portion 134b includes a pair of longitudinal slots 1312 formed in its side wall 1032b to allow an actuation system to actuate the upper housing portion 102a and/or the collar 118, in use. The longitudinal slots 1312 are formed so as to prevent, or at least mitigate, user intervention with the actuatable lugs. The second portion 134b also includes an aperture 1310b formed in the top wall 1308b to allow the upper housing portion 102a (see below) to protrude therethrough, and also includes a flat rear wall 1314 having a slot 1302b. The second portion 134b also includes a raised rib 1315 adjoining the side wall 1032b to the top wall 1308b that is received within the recess 1311 (see above) to allow for the two portions to be welded together, in use. Finally, the side wall 1032b includes a protective wall 1313, formed as a gripping region for a user, arranged to be received with the arcuate slot 1309 (see above). The protective wall 1313 overlays the longitudinal slot 1312 so as to enclose the same and aid in mitigating user access within the longitudinal slot 1312.

It is noted that the first portion 134a and the second portion 134b may be formed separately or integrally. If the portions 134a, 134b are formed separately, any appropriate means to couple the portions 134a, 134b together is envisaged, including welding, adhering, clipping or the like.

FIGS. 66(a) to 66(c), 67(a) and 67(b) illustrate the upper housing portion 102a of the connector 1300. The upper housing portion 102a is provided with an anti-rotation feature 1320, formed in this example as a plurality of angled notches, adjacent, or as part of, the threaded portion 107 of the connector 1300. The anti-rotational features 1320 may cooperate with corresponding anti-rotation features, such as complementary notches or rips, on a receptacle to be connected. As best shown in FIG. 67(a), the first septum seal 108 is co-molded with the upper housing portion 102a and is formed by a raised annular portion enclosing a flat portion for piercing, in use.

FIGS. 68(a) and 68(b) illustrate another embodiment of the upper housing portion 102a of the connector 1300. The upper housing portion 102a is as described in FIGS. 66(a) to 66(c), 67(a) and 67(b), and further includes a pair of elongate ribs 1321 extending longitudinal either side of the actuatable lugs 804a, 804b. The elongate ribs 1321 generally span the majority of the length of the upper housing portion 102a. In use, the elongate ribs 1321 are caused to frictionally engage with a recess (not shown) or the inner surface of the outer sleeve 134.

FIGS. 69(a) to 69(c), 70(a) and 70(b) illustrate the lower housing portion 102b of the connector 1300. As can be seen, the lower housing portion 102b includes an inner body 1006 that extends beyond the bottom edge of the outer body 1004. In this way, a better engagement with a component to be coupled may be achieved. Further, the lower housing portion 102b includes a co-molded septum seal 110 as described substantially above.

The lower housing portion 102b further includes a plurality of strengthening ribs 1301, each being connected to one of the tongues 708. Each rib 1301 extends longitudinally, or axially, and parallel to, the tongues 708 to impart a stiffness, or increased strength, thereto. As described above in relation to FIGS. 21(a) to 21(e) and 22(a) to 22(e), the tongues 708 serve as needle-safe features.

FIGS. 71(a) and 71(b) illustrate another embodiment of the lower housing portion 102b of the connector 1300. As can be seen, the lower housing portion 102b is as described in FIGS. 69(a) to 69(c), 70(a) and 70(b), and further includes a pair of flanges 1007 extending outwardly from an outer surface of the outer body 1004. The pair of flanges 1007 diametrically opposes one another, i.e., they are displaced by an angle of 180 degrees. In use, the pair of flanges 1007 is received within corresponding slots 1009 of the outer sleeve 134, as shown in FIG. 71(b), so as to resist movement of the lower housing portion 102b during use.

FIGS. 72(a) to 72(c) illustrate a hollow needle 112 and a collar 118 of the connector 1300. The hollow needle 112 is as described above, and, in particular, includes a pencil-point closed end 1011, i.e., a pointed closed end, including a port, or an aperture, 1013 adjacent the pencil-point closed end 1011 and extending perpendicularly with respect to the shaft of the hollow needle 112. The hollow needle further includes an open end 1015, which is beveled in the depicted embodiment.

FIGS. 73(a) and 73(b) illustrate a further embodiment of a hollow needle 112 and a collar 118 of the connector 1300. As can be seen, the hollow needle 112 is as described in FIGS. 72(a) to 72(c), but the port 1013 extends through the hollow needle 112 so as to form a pair of diametrically opposed openings 1013a, 1013b. This allows fluid to drain out of each of the openings, so as to mitigate blockage of the hollow needle 112 during use. The hollow needle further includes a longitudinally extending slot 1017 extending from the open end 1015 toward the collar 118. This allows the fluid to more easily drain from a connected container into the bore of the hollow needle 112.

FIGS. 74(a) and 74(b) illustrate first and second gaiters 1022, 1024. The first gaiter 1022 includes a central portion 1022a flanked by two end portions 1022b, 1022c. The central portion 1022a has a larger length than the two end portions 1022b, 1022c. This arrangement aids the appropriate collapsing of the first gaiter 1022 during use. That is, the central portion 1022a of the bellows forms an extended cylindrical region having no Z-folds. The extended cylindrical region adjoins the two end portions 1022b, 1022c. The volume of the central portion 1022a may be generally larger than the volume of the end portions 1022b, 1022c.

FIGS. 75(a) to 75(c), 76(a) and 76(b) illustrate a portion of an aseptic seal system 1350, including a clip portion 1352. The clip portion 1352 is formed as a generally drawer-like feature. The clip portion 1352 includes a front wall 1354, a rear wall 1356, and two side walls 1358 adjoining the front and rear walls 1354, 1356. The side walls 1358 are each formed with a shoulder 1360. A base wall 1362 is provided having a circular protrusion 1364 extending therefrom. The front wall 1354, rear wall 1356, side walls 1358 and base wall 1362 generally define a hollow body. A plurality of strengthening ribs 1363 are provide within the hollow body, extending parallel to the side walls 1358 and perpendicularly to the front and rear walls 1354, 1356. In some examples, a top wall (not shown) may also be provided.

The clip portion 1352 is arranged so as to couple to an aseptic membrane (not shown) by virtue of the protrusion 1364. To this end, the protrusion 1364 may include one or more retaining clips. Further, the shoulders 1360 are arranged to be engaged by an actuation mechanism, so as to be able to push the clip portion 1352 from the outer sleeve 134 once slidably received therein. Thus, an automated system may be more easily achieved. The clip portion 1352 may be composed of high density polyethylene (HDPE), low density polyethylene (LDPE), or a like material.

Figure 77:
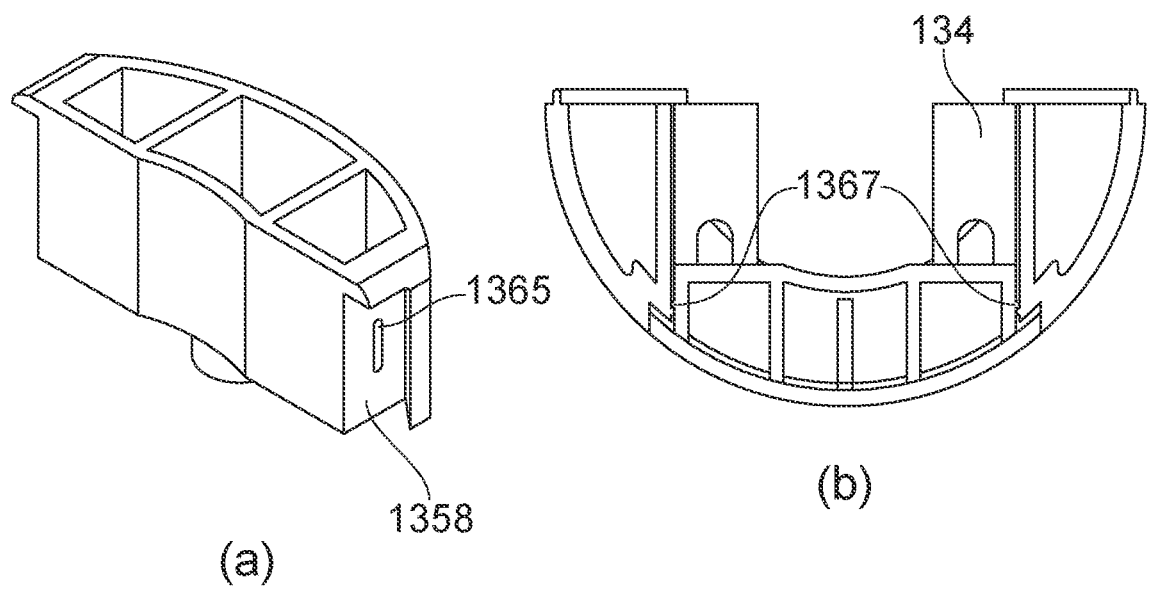
FIG. 77 illustrates (a) a perspective view of another embodiment of the clip portion of FIG. 75, and (b) a bottom view of the clip portion of (a) assembled to the outer sleeve.

FIGS. 77(a) and 77(b) illustrate another embodiment of the clip portion 1352 of the connector 1300. As can be seen, the clip portion 1352 is as described in FIGS. 75(a) to 75(c), 76(a) and 76(b), and further includes a locating element, formed as a longitudinal extending rib 1365 formed on each of the side walls 1358 of the clip portion 1352. The ribs 1365 cooperate with corresponding ribs 1367, or alternatively corresponding recesses, formed as part of the bottom portion of the outer sleeve 134.

FIGS. 78(a) to 78(c) illustrates a transit cover 1370 for covering the bottom, i.e., proximal, end of the connector 1300 during transportation and storage. The transit cover 1370 is complementary in shape and size to the proximal end 106 of the connector 1300. In particular, the transit cover 1370 includes a pair of protruding blocks 1372 configured to engage with corresponding spaces of the connector 1300 and engage portions of the connector 1300 by a friction-fit in use.

FIGS. 79(a) through 79(j) illustrate a method of assembling the connector 1300. Firstly, the gaiters 1022, 1024 are assembled (FIG. 79(a)). Secondly, the gaiters 1022, 1024 are assembled to the collar 118 so as to enclose the hollow needle 112 (FIG. 79(b)). The gaiters 1022, 1024 may be secured in place by any appropriate means, such as clips, adhesive, welding or the like. Thirdly, the lower housing portion 102b is assembled to the collar 118 (FIG. 79(c)). Fourthly, the upper housing portion 102a is assembled to the lower housing portion 102b (FIG. 79(d)). Fifthly, the second portion 134*b* of the outer sleeve 134 is assembled to the pre-assembled components of FIG. 79(*d*) (FIG. 79(*e*)). Sixthly, the first portion 134*a* of the outer sleeve 134 is assembled to the second portion 134*b* of the outer sleeve 134 (FIG. 79(*f*)). The first portion 134*a* and the second portion 134*b* may be adhered, welded, clipped or the like to one another. Seventhly, an aseptic seal system 1350 is provided. The aseptic seal system 1350 includes an aseptic membrane 1351 and a clip portion 1352 as described above. The aseptic membrane 1351 is affixed to the lower housing portion 102*b* so as to aseptically seal the second septum seal 110. The clip portion 1352 is slidably engaged with the outer sleeve 134. The connector 1300 is then provided with the aseptic seal system 1350 (FIG. 79(*g*)). Eighthly, a transit cover 1370, optionally composed of polypropylene (PP) or low density polyethylene (LDPE), is provided over the proximal end 106 of the connector 1300 (FIG. 79(*h*)). Ninthly, a transit cap 1390, optionally composed of polypropylene (PP) or low density polyethylene (LDPE), is provided over the distal end 104 of the connector 1300 (FIG. 79(*i*)). Tenthly, indicia 1392 is added to a recessed region 1394 of the outer sleeve 134 (FIG. 79(*j*)).

Figure 80:
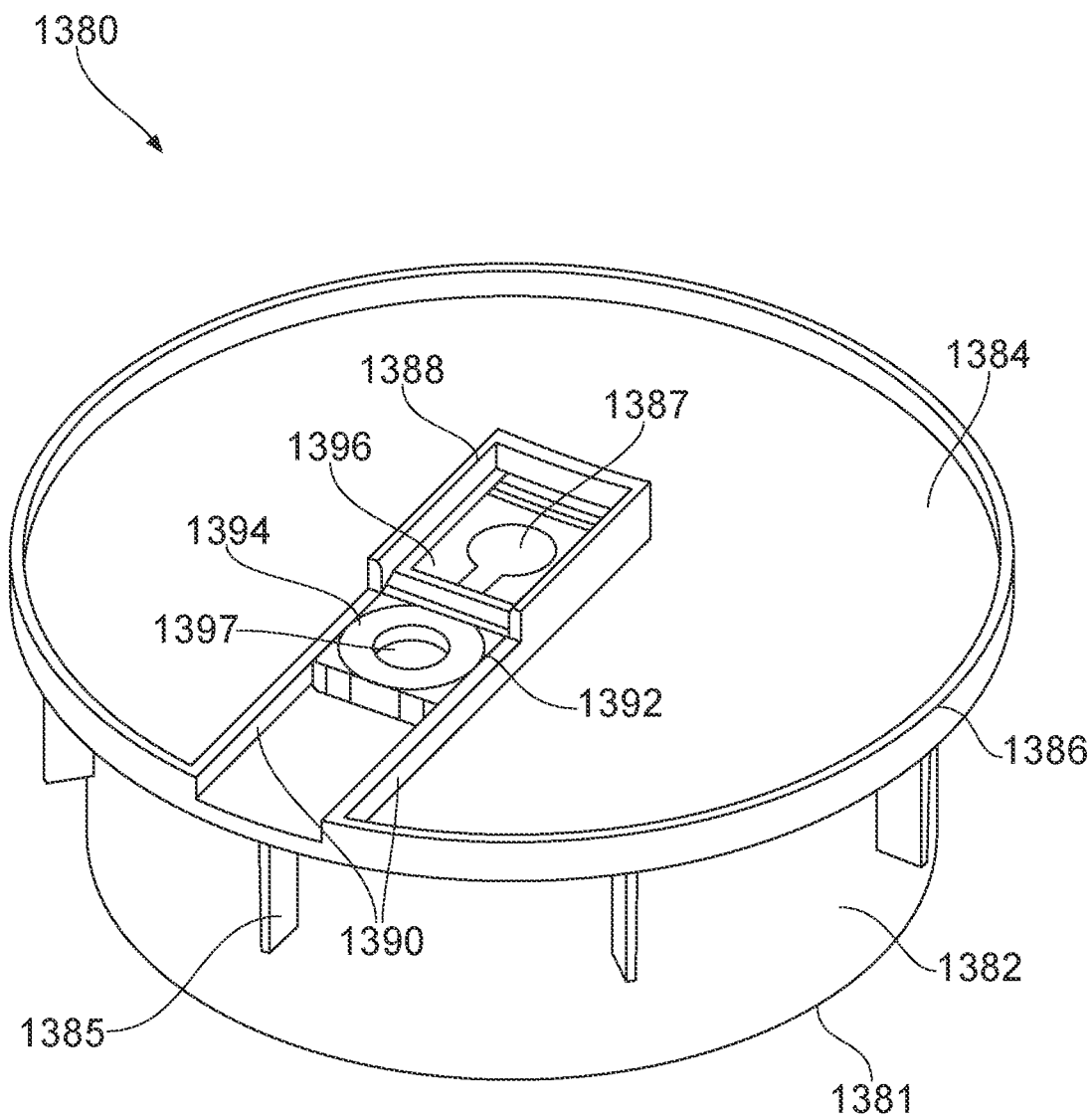
FIG. 80 illustrates a perspective view of an embodiment of an interface plate arranged to be aseptically connected to the connector of FIG. 63.

FIG. 80 illustrates an embodiment of an interface plate, or a container lid, 1380 for use with any of the connectors as described herein. The interface plate 1380 is substantially similar to the interface plate 1150, and its associated operation mechanism, as described in relation to FIGS. 50(*a*) and 50(*b*).

The interface plate 1380 includes a base 1381 having a side wall 1382 upstanding therefrom to a top wall 1384. The top wall 1384 generally overhangs the side wall 1382, and a number of strengthening ribs 1385 are provided connecting the side wall 1382 to an underside surface of the top wall 1384. The base 1381 includes a connection element, such as a screw thread or a clip, to allow connection of the interface plate 1380 to a container, a receptacle or the like. The top wall 1384 is provided with an outer circular rim 1386, and a centrally disposed septum seal 1387 enclosed by a U-shaped upstanding locating wall 1388. The septum seal 1387 is a generally planar septum seal, i.e., generally flat, recessed into the surface of the top wall 1384. A rail 1390 is provided, extending radially outwardly from the open end of the U-shaped locating wall 1388. There is further provided an aseptic seal system 1392, including a clip portion 1394 and an aseptic membrane 1396 attached to the clip portion 1394. The aseptic membrane 1396 is disposed over the septum seal 1387 so as to aseptically seal the same, and the clip portion 1394 is received within the rail 1390 so as to be slidably movable therein.

The interface plate 1380 will now be described in use, with reference to the connector 1300 as shown in FIGS. 63 to 77, although any other connector described herein may also be used. Firstly, the connector 1300 is located, held or otherwise retained above the top wall 1384 of the interface plate 1380. The connector 1300, specifically the aseptic seal system 1350 thereof, is caused to engage with the aseptic seal system 1392 of the interface plate 1380. In particular, a protrusion 1364 of the aseptic seal system 1350 of the connector 1300 is caused to engage with the clip portion 1394 of the aseptic seal system 1392, specifically an aperture 1397 within the clip portion 1394. Secondly, and simultaneously, a face of an aseptic membrane (not shown) of the aseptic seal system 1350 of the connector 1300 is caused to engage a face of the aseptic membrane 1396 of the interface plate 1380. For example, the aseptic membranes may each be folded to form an aseptic face, each aseptic face disposed over their respective septum seals 110, 1387, and a connecting face, for connecting to a corresponding connecting face of the other aseptic seal system. The respective connecting faces may be caused to engage and connect, or couple, by any appropriate means, such as adherence or the like. The upstanding wall 1388 aids the positioning of the aseptic membrane of the connector 1300 onto the aseptic membrane 1396 of the interface plate 1380.

Once the respective clip portions 1352, 1394, and respective aseptic membranes are coupled, an actuation system (not shown) may engage the aseptic seal system 1392, and/or the aseptic seal system 1350 of the connector 1300, so as to slide the respective clip portions 1352, 1394 along a radial axis. Generally, the respective clip portions 1352, 1394 are slid along an axis extending from the septum seal 1387 and generally defined by the rail 1390, which extends radially from a central position of the top wall 1384. In this way, as each clip portion 1352, 1394 is slid away from the respective septum seal 110, 1387, the respective aseptic membrane is caused to pull, peel or the otherwise remove in a direction that is distal to the respective septum seal 110, 1387. The specific removal steps are dictated by the folding geometries of the aseptic membranes in embodiments in which they are folded. Thus, by removing each aseptic membrane, each septum seal 110, 1387, i.e., of the connector 1300 and of the interface plate 1380, are allowed to engage one another in a face-to-face and aseptic, or sterile, arrangement. The connector 1300 may then be operated as described above to provide a fluid passageway through the respective septum seals 110, 1387, specifically by piercing the septum seals 110, 1387 with a hollow needle 112, thereby fluidly connecting one fluid volume, such as one connected to an end of the connector 1300, to another fluid volume, such as one connected to an end of the interface plate 1380.

Although several embodiments are described herein, persons skilled in the art will recognize that aspects of each embodiment are disclosed in combination with any other embodiment. For example, any of the upper housing portions, lower housing portions, outer sleeves, collars, hollow needles, actuation mechanisms, aseptic seal systems or the like may be selected from the above disclosure.

As will be appreciated by persons skilled in the art, the components of the connectors, receptacles, interface place and the like may be composed of any suitable material. For example: the outer sleeve may be composed of polycarbonate, acrylonitrile butadiene styrene (ABS), high impact polystyrene sheet (HIPS); the aseptic seal system may include a clip portion composed of high density polyethylene (HDPE) and/or an aseptic membrane composed of polyethylene (PE); the collar may be composed of polycarbonate, acrylonitrile butadiene styrene (ABS), high impact polystyrene sheet (HIPS); the hollow needle may be composed of stainless steel or another appropriate biocompatible material or metal; the gaiters may be composed of low density polyethylene (LDPE), a thermoplastic elastomer (TPE), a silicon or the like; the gaiter clips may be composed of high density polyethylene (HDPE); the lower housing portion may be composed of polycarbonate, acrylonitrile butadiene styrene (ABS), high impact polystyrene sheet (HIPS); the pierceable hermetic seal of the lower housing portion may be composed of a thermoplastic elastomer, or a silicon and/or may be co-molded with the lower housing portion; the upper housing portion may be composed of polycarbonate, acrylonitrile butadiene styrene (ABS), high impact polystyrene sheet (HIPS); the pierceable hermetic seal of the upper housing portion may be composed of a thermoplastic elastomer (TPE), or a silicon and/or may be co-molded with the upper housing portion; and the transit cover and/or the transit cap may be composed of polypropylene (PP), low density polyethylene (LDPE), or a combination thereof. Any combination of materials is also envisaged as discussed above. Such materials provide multiple manufacturing and processing advantages, in addition to being suitable for cell and/or gene therapy manufacture.

Generally, it will be appreciated by persons skilled in the art that the above embodiments have been described by way of an example only and not in any limitative sense, and that various alternations and modifications are possible without departing from the scope of the disclosure as defined by the accompanying claims. Various modifications to the detailed designs as described above are possible; for example, variations may exist in shape, size, arrangement, assembly, sequence or the like.

What is claimed is:

1. A connector, for introducing or extracting a material to or from at least one receptacle, comprising:
   a housing extending between a distal end and a proximal end, the housing comprising a pierceable seal at both the proximal end and the distal end;
   a double-ended hollow needle mounted within the housing between the distal end and the proximal end of the housing, a first end of the double-ended hollow needle facing the pierceable seal at the proximal end of the housing, and a second end of the double-ended hollow needle facing the pierceable seal at the distal end of the housing; and
   an actuating mechanism configured to enable the double-ended hollow needle to pierce the pierceable seals at both the proximal end and the distal end of the housing, thereby forming a communication through each pierceable seal, such that material is able to transfer through the connector,
   wherein the actuating mechanism comprises the housing, which is a collapsible housing, comprising an upper housing portion and a lower housing portion, the upper housing portion being axially movable along a central longitudinal axis with respect to the lower housing portion, so as to collapse with respect to the lower housing portion to enable the double-ended hollow needle to pierce the pierceable seal at the distal end of the housing, the upper housing portion comprising at least one actuatable lug configured to move the upper housing portion along the central longitudinal axis; and
   wherein the actuating mechanism further comprises a collar operably coupled to the double-ended hollow needle, the collar comprising at least one actuatable lug configured to move the collar along the central longitudinal axis to enable the double-ended hollow needle to pierce the pierceable seal at the proximal end of the housing.

2. The connector according to claim 1, wherein, in use, the first end of the double-ended hollow needle is fluidly connectable to a first receptacle, and wherein, in use, the actuating mechanism enables the double-ended hollow needle to pierce the pierceable seal at the distal end of the housing to fluidly connect the second end of the double-ended hollow needle to a second receptacle.

3. The connector according to claim 1, wherein:
   an outer sleeve encloses the upper housing portion and the lower housing portion and comprises a side wall having a first slot and a second slot, the second slot being diametrically opposed to the first slot;
   the upper housing portion comprises a first actuatable lug extending from a body of the upper housing portion, and a second actuatable lug extending from the body of the upper housing portion, the first and second actuatable lugs being diametrically opposed; and
   the collar comprises a first actuatable lug extending from an outer wall of the collar, and a second actuatable lug extending from the outer wall of the collar, the first and second actuatable lugs being diametrically opposed; and
   the first actuatable lug of the upper housing portion and the first actuatable lug of the collar protrude at least partially through the first slot of the outer sleeve, and the second actuatable lug of the upper housing portion and the second actuatable lug of the collar protrude at least partially through the second slot of the outer sleeve.

4. The connector according to claim 3, wherein the double-ended hollow needle is biasedly mounted in a direction toward the proximal end of the housing by a first spring.

5. The connector according to claim 4, wherein the double-ended hollow needle is biasedly mounted in a direction toward the distal end of the housing by a second spring.

6. The connector according to claim 5, wherein the first spring provides a first biasing force, and the second spring provides a second biasing force, the first biasing force and the second biasing force being approximately equal.

7. The connector according to claim 5, wherein the first spring provides a first biasing force, and the second spring provides a second biasing force, the first biasing force being greater than the second biasing force.

8. The connector according to claim 1, wherein the connector further comprises an aseptic seal system including an aseptic membrane and a clip portion, the aseptic membrane being disposed over the pierceable seal at one or each end of the housing of the connector and being operably coupled to the clip portion.

9. The connector according to claim 8, wherein the clip portion is slidably operably connected to the connector such that the clip portion is slidable between a first configuration, in which the aseptic membrane is disposed over at least one of the pierceable seals, and a second configuration, in which the aseptic membrane is removed from at least one of the pierceable seals.

10. The connector according to claim 1, wherein a second receptacle is connected, or connectable, to the housing of the connector.

11. The connector according to claim 1, wherein the communication through the pierceable seal at both the proximal end and the distal end of the housing comprises a communication between a connected, or connectable, first receptacle and a connected, or connectable, second receptacle, such that material is able to transfer through the connector between the first receptacle and the second receptacle.

12. A system, comprising:
   a connector, for introducing or extracting a material to or from at least one receptacle, comprising:
      a housing extending between a distal end and a proximal end, the housing comprising a pierceable seal at both the proximal end and the distal end;
      a double-ended hollow needle mounted within the housing between the distal end and the proximal end of the housing, a first end of the double-ended hollow needle facing the pierceable seal at the proximal end of the housing, and a second end of the double-ended hollow needle facing the pierceable seal at the distal end of the housing; and an actuating mechanism configured to enable the double-ended hollow needle to pierce the pierceable seals at both the proximal end and the distal end of the housing, thereby forming a communication through each pierceable seal, such that material is able to transfer through the connector, wherein the actuating mechanism comprises the housing, which is a collapsible housing, comprising an upper housing portion and a lower housing portion, the upper housing portion being axially movable along a central longitudinal axis with respect to the lower housing portion, so as to collapse with respect to the lower housing portion to enable the double-ended hollow needle to pierce the pierceable seal at the distal end of the housing, the upper housing portion comprising at least one actuatable lug configured to move the upper housing portion along the central longitudinal axis; and wherein the actuating mechanism further comprises a collar operably coupled to the double-ended hollow needle, the collar comprising at least one actuatable lug configured to move the collar along the central longitudinal axis to enable the double-ended hollow needle to pierce the pierceable seal at the proximal end of the housing; and a first receptacle detachably coupled to one end of the connector and wherein the first receptacle is connected to the first end of the double-ended hollow needle; and a second receptacle detachably coupled to one end of the connector and wherein the second receptacle is connected to the second end of the double-ended hollow needle.

13. A method of connecting two receptacles, comprising the steps of:

providing a connector for introducing or extracting a material to or from at least one receptacle, the connector comprising:

a housing extending between a distal end and a proximal end, the housing comprising a pierceable seal at both the proximal end and the distal end;

a double-ended hollow needle mounted within the housing between the distal end and the proximal end of the housing, a first end of the double-ended hollow needle facing the pierceable seal at the proximal end of the housing, and a second end of the double-ended hollow needle facing the pierceable seal at the distal end of the housing; and an actuating mechanism configured to enable the double-ended hollow needle to pierce the pierceable seals at both the proximal end and the distal end of the housing, thereby forming a communication through each pierceable seal, such that material is able to transfer through the connector, wherein the actuating mechanism comprises the housing, which is a collapsible housing, comprising an upper housing portion and a lower housing portion, the upper housing portion being axially movable along a central longitudinal axis with respect to the lower housing portion, so as to collapse with respect to the lower housing portion to enable the double-ended hollow needle to pierce the pierceable seal at the distal end of the housing, the upper housing portion comprising at least one actuatable lug configured to move the upper housing portion along the central longitudinal axis; and wherein the actuating mechanism further comprises a collar operably coupled to the double-ended hollow needle, the collar comprising at least one actuatable lug configured to move the collar along the central longitudinal axis to enable the double-ended hollow needle to pierce the pierceable seal at the proximal end of the housing;

connecting the distal end of the housing of the connector to a first receptacle comprising a pierceable seal, such that the pierceable seal at the distal end of the housing of the connector is coaxially aligned with the pierceable seal of the first receptacle;

detachably connecting the proximal end of the housing of the connector to a second receptacle comprising a pierceable seal, such that the pierceable seal at the proximal end of the housing of the connector is coaxially aligned with the pierceable seal of the second receptacle; and actuating the double-ended hollow needle to pierce the pierceable seals at each end of the housing of the connector and through the pierceable seals of the first receptacle and the second receptacle, thereby connecting the first receptacle and the second receptacle.

* * * * *